US012662515B2

(12) United States Patent
Jon et al.

(10) Patent No.: US 12,662,515 B2
(45) Date of Patent: Jun. 23, 2026

(54) FUSION PROTEIN COMPRISING BP26 AND ANTIGENIC POLYPEPTIDE

(71) Applicant: KOREA ADVANCED INSTITUTE OF SCIENCE AND TECHNOLOGY, Daejeon (KR)

(72) Inventors: Sangyong Jon, Daejeon (KR); Sukmo Kang, Chungcheongbuk-do (KR); Yujin Kim, Daejeon (KR); Ji-Joon Song, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 414 days.

(21) Appl. No.: 18/139,003

(22) Filed: Apr. 25, 2023

(65) Prior Publication Data

US 2023/0257426 A1 Aug. 17, 2023

Related U.S. Application Data

(63) Continuation of application No. PCT/KR2021/015113, filed on Oct. 26, 2021.

(30) Foreign Application Priority Data

Oct. 26, 2020 (KR) ........................ 10-2020-0139699

(51) Int. Cl.
| | |
|---|---|
| *C07K 14/23* | (2006.01) |
| *A61K 39/02* | (2006.01) |
| *A61K 39/10* | (2006.01) |
| *A61K 39/145* | (2006.01) |
| *A61P 37/04* | (2006.01) |
| *C07K 14/11* | (2006.01) |
| *C12N 15/63* | (2006.01) |

(52) U.S. Cl.
CPC .............. *C07K 14/23* (2013.01); *A61K 39/02* (2013.01); *A61K 39/145* (2013.01); *A61P 37/04* (2018.01); *C07K 14/11* (2013.01); *C12N 15/63* (2013.01); *A61K 2039/10* (2013.01)

(58) Field of Classification Search
None
See application file for complete search history.

(56) References Cited

U.S. PATENT DOCUMENTS

| | | | | |
|---|---|---|---|---|
| 5,268,276 A | * | 12/1993 | Holmgren .............. | C12N 15/74 |
| | | | | 435/69.7 |
| 2003/0082170 A1 | * | 5/2003 | Lindler .............. | A61K 47/6811 |
| | | | | 424/130.1 |

FOREIGN PATENT DOCUMENTS

| | | |
|---|---|---|
| CN | 105906717 A | 8/2016 |
| CN | 109486846 A | 3/2019 |
| EP | 2575876 A1 | 4/2013 |
| KR | 10-2014-0131802 A | 11/2014 |

OTHER PUBLICATIONS

Xin et al. Clinical and Vaccine Immunology, vol. 20 No. 9, p. 1410-1417, 2013.*
Liu et al. North American Journal of Medical Sciences, vol. 4, issue 12, p. 651-655, 2012.*
26 kDa periplasmic immunogenic protein [*Brucella abortus* 2308] GenBank: KFJ52515.1 Aug. 19, 2014.*
International Search Report from corresponding PCT Application No. PCT/KR2021/015113, dated Feb. 14, 2022.
Zhu, L., et al.; "Comparison of Immune Effects Between *Brucella* Recombinant Omp10-Omp28-L7/L12 Proteins Expressed in Eukaryotic and Prokaryotic Systems", Frontiers in veterinary Science, Sep. 18, 2020, vol. 7, thesis No. 576, pp. 1-12.
NCBI, GenBank Accession No. WP_00269580.1, Multispecies outer membrane protein BP26/OMP 28 [Brucella] Jan. 6, 2020.
Zykova, A. A., et al.; "Highly Immunogenic Nanparticles Based on a Fusion Protein Comprising the M2e of Influenza A Virus and a Lipopopeptide", Viruses, Oct. 6, 2020, vol. 12, thesis No. 1133, pp. 1-11.
Kang, S. et al.; "Antigen-Presenting, Self-Assembled Protein Nanobarrels as an Adjuvant-Free Vaccine Platform against Influenze Virus", ACS Nano, Jun. 11, 2021, vol. 15, pp. 10722-10732.
Kim Daegeun et al: "BrucellaImmunogenic BP26 Forms a Channel-like tructure",Journal of Molecular Biology, Academic Press, United Kingdom,vol. 425, No. 7, Jan. 23, 2013 (Jan. 23, 2013), pp. 1119-1126, XP028997888,ISSN: 0022-2836, DOI: 10.1016/J.JMB.2013.01.015.
Schotsaert M et al: "Universal M2 ectodomain-based influenza A vaccines:Preclinical and clinical developments",Expert Review of Vaccines, Future Drugs, London, GB, vol. 8, No. 4, Jan. 1, 2009 (Jan. 1, 2009 ), pp. 499-508, XP009127026,ISSN: 1476-0584, DOI: 10.1586/ERV.09.6.
EESR for EP Patent Application No. 21886763.8, dated Sep. 11, 2024.
Notice of Allowance for KR Patent Application No. 10-2021-0144034, dated Dec. 18, 2024.
Office Action from corresponding Korean Patent Application No. 10-2021-0144034, dated Apr. 25, 2024.
GenBank JF918758.1 *Brucella melitensis* Omp28 gene (May 25, 2011).

* cited by examiner

*Primary Examiner* — Oluwatosin A Ogunbiyi
(74) *Attorney, Agent, or Firm* — Harness, Dickey & Pierce, PLC

(57) ABSTRACT

The present disclosure relates to a fusion protein comprising BP26 and an antigenic polypeptide, and to a nanoarchitecture comprising same. A vaccine composition comprising the fusion protein, nanoarchitecture, or combination thereof of the present disclosure can be used to effectively prevent or treat pathogens or cancer, and thus can be used as a multi-purpose vaccine platform.

12 Claims, 33 Drawing Sheets

Specification includes a Sequence Listing.

| | Monomer | Multimer |
|---|---|---|
| BP26-WT | 28.1 kDa | 464 kDa |
| BP26-M2e(×4) | 39.6 kDa | 630 kDa |
| BP26-M2e(×8) | 51.3 kDa | 820 kDa |

A

B

| Virus strain | Subtype | M2e amino acid sequence | |
|---|---|---|---|
| A/PR/8 | H1N1 | S L L T E V E T P I R N E W G C R C N D S S D | (SEQ ID NO:4) |
| A/CA/04/09 | H1N1 | S L L T E V E T P I R N G W E C K C S D S S D | (SEQ ID NO:5) |
| A/Aquatic bird/Korea | H5N2 | S L L T E V E T P I R S E W E C R C S D S S D | (SEQ ID NO:6) |
| M2e amino acid sequence in BP26 | | S L L T E V E T P I R N E W G S R S N D S S D | (SEQ ID NO:3) |

A/CA/04/09 challenge

1: Marker
2: BP26-LQ-M30(×10)

B16-F10 (s.c.)        Immunization

D0        D4    D8    D12

B16-F10

---- Control
---- BP26-WT + M30 + CpG
---- BP26-LQ-M30(× 10)
---- BP26-LQ-M30(× 10) + CpG

1

FUSION PROTEIN COMPRISING BP26 AND ANTIGENIC POLYPEPTIDE

CROSS-REFERENCE TO RELATED APPLICATIONS

This application is a continuation application of PCT Application No. PCT/KR2021/015113, filed on Oct. 26, 2021, which claims benefit of Korean Patent Application No. 10-2020-0139699, filed on Oct. 26, 2020. The entire disclosures of the applications identified in this paragraph are incorporated herein by references.

SEQUENCE LISTING

This application contains references to amino acid sequences and/or nucleic acid sequences which have been submitted concurrently herewith as the sequence listing text file entitled "000385usnp_2ndSequenceListing.xml", file size 24,457 bytes, created on 26 Sep. 2025. The aforementioned sequence listing is hereby incorporated by reference in its entirety pursuant to 37 C.F.R. § 1.52 (e) (5).

FIELD

The present disclosure has been made with the support of the ministry of Science and ICT under Project ID. No. 1711074336, and sub-project No. 2018R1A3B1052661, which was conducted by the "Korea Advanced Institute of Science and Technology" in the research program named "Center for Tumor Microenvironment-Targeting Precision Bio-nanomedicine" as a branch of the research project titled "Fundamental Research Project" under the research management of the National Research Foundation of Korea, from Jun. 1, 2018 to Feb. 28, 2027.

Also, the present disclosure has been made with the support of the ministry of Science and ICT under Project ID. No. 1711070719, and sub-project No. 2018M3A9B5023527, which was conducted by the "Korea Advanced Institute of Science and Technology" in the research program named "Development of Tumor Microenvironment-Targeting and Responsive Drug Delivery Platform Technology" as a branch of the research project titled "Original Technology Development Project" under the research management of the National Research Foundation of Korea, from Apr. 1, 2018 to Dec. 31, 2020.

This application claims priority to and the benefit of Korean Application Number 10-2020-0139699, filed in the Korean Intellectual Property Office on Oct. 26, 2020, the entire content of which is incorporated herein by reference.

The present disclosure relates to a fusion protein comprising BP26 and an antigenic polypeptide.

BACKGROUND

Various nanomaterials can be used as antigen delivery carriers to induce humoral or cellular immunity for the development of anticancer and antiviral vaccines. In particular, naturally occurring self-assembled protein nano-architectures such as ferritin and heat shock proteins can harbor or display antigens and can be used as antigen delivery carriers. Nanoarchitectures having such antigen display, self-assembly, symmetrical structure, and nano size can mimic a virus-like architecture, but are not effective in eliciting antigen-specific immune responses without additional use of an adjuvant that activates immunity. However, preexisting adjuvants may cause various side effects, such as inflammation and edema at the injection site, and systemic immunotoxicity.

SUMMARY

Technical Problem

Leading to the present disclosure, intensive and thorough research conducted by the present inventors into the development of a self-assembled protein nanoarchitecture that serves as an adjuvant and a carrier resulted in the finding that BP26, the outer membrane protein of *Brucella*, formed nanoarchitectures through self-assembly and the nanoarchitectures can effectively deliver antigens.

Accordingly, an aspect of the present disclosure is to provide a fusion protein comprising BP26 and an antigenic polypeptide.

Another aspect of the present disclosure is to provide a nanoarchitecture comprising the fusion protein.

A further aspect of the present disclosure is to provide a vaccine composition comprising the fusion protein, the nanoarchitecture, or a combination thereof.

Solution to Problem

According to one aspect thereof, the present disclosure provides a fusion protein comprising BP26 and an antigenic polypeptide.

As used herein, the term "BP26" refers to an outer membrane protein of *Brucella*, also referred to as BP26/OMP28. With the property of self-assembly, BP26, which is a major immunodominant antigen, exhibits antigen carrier and adjuvant effects.

In an embodiment of the present disclosure, BP26 includes the amino acid sequence of SEQ ID NO: 1, but is not limited thereto.

As used herein, the term "amino acid" refers to the most basic structural unit of a protein molecule. In the structural unit, one carbon atom possesses, as substituents, an amino group (—NH2), a carboxyl group (—COOH), and a side chain represented by R.

In an embodiment of the present disclosure, the BP26 includes a variant of the amino acid sequence of SEQ ID NO: 1.

For example, a change may be imparted to the amino acid sequence of the polypeptide of BP26 in order to improve the biological properties thereof. Such changes include, for example, deletions, insertions, and/or substitutions of amino acid sequence residues of the polypeptide.

The variant has "substantial similarity" to the original polypeptide. As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity.

Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein.

Such amino acid variations are made based on the relative similarity of amino acid side chain substituents, e.g., hydrophobicity, hydrophilicity, charge, size, and the like. According to the analysis of the size, shape and type of amino acid side chain substituents, arginine, lysine and histidine are all positively charged residues; alanine, glycine and serine have similar sizes; It can be seen that phenylalanine, tryptophan and tyrosine have similar shapes. Therefore, based on these considerations, arginine, lysine and histidine; alanine, glycine and serine; and phenylalanine, tryptophan and tyrosine are regarded to be biologically functional equivalents.

For introducing mutations, the hydrophobicity indexes of amino acids may be considered. Each amino acid is assigned a hydrophobicity index according to its hydrophobicity and charge: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. It is known that certain amino acids may be substituted for other amino acids having a similar hydrophobicity index or score and still retain a similar biological activity. In making changes based upon the hydrophobicity index, the substitution of amino acids whose hydropathic indices are within ±2 is preferred, those which are within ±1 are particularly preferred, and those within ±0.5 are even more particularly preferred.

It is also understood in the art that that substitution between amino acids having similar hydrophilicity values results in proteins having equivalent biological activity. As disclosed in U.S. Pat. No. 4,554,101, the following hydrophilicity values are assigned to each amino acid residue: arginine (+3.0); lysine (+3.0); Aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

When the mutation is introduced with reference to the hydrophilicity value, the substitution is preferably made between amino acids exhibiting a difference in the hydrophilicity value within ±2, more preferably within ±1, and even more preferably within ±0.5.

Amino acid exchanges in proteins that do not entirely alter the activity of the molecule are known in the art (H. Neurath, R. L. Hill, The Proteins, Academic Press, New York, 1979). The most common exchanges occur between amino acid residues Ala/Ser, Val/Ile, Asp/Glu, Thr/Ser, Ala/Gly, Ala/Thr, Ser/Asn, Ala/Val, Ser/Gly, Thy/Phe, Ala/It is an exchange between Pro, Lys/Arg, Asp/Asn, Leu/Ile, Leu/Val, Ala/Glu, Asp/Gly.

In an embodiment of the present disclosure, the BP26 polypeptide of the present disclosure has at least 90% sequence homology with the amino acid sequence of SEQ ID NO: 1 (e.g., 90%, 91%, 92%, 93%, 94%, 95%, 96%, 97, 98%, or 99%). All integers between 90% and 100% (both inclusive), and decimals existing therebetween, are included within the scope of the present disclosure with respect to % homology.

In an embodiment of the present disclosure, the antigen included in the fusion protein is a pathogen-derived antigen, a tumor-derived antigen, or other cellular immunity activating peptide.

In an embodiment of the present disclosure, the fusion protein includes one or more antigen-derived antigenic polypeptides from the pathogen- or tumor-derived antigen. In the Example section, for example, the fusion protein of the present disclosure included 4 or 8 M2e polypeptides derived from influenza virus, or 6 M30 polypeptides, which are tumor-derived MHC class II neoantigens from mouse melanoma cell line B16-F10.

More specifically, the fusion protein may include 1 to 20, 1 to 18, 1 to 16, 1 to 14, 1 to 12, 1 to 10, 1 to 8, 1 to 6, 1 to 4, 1 to 2, 2 to 20, 2 to 18, 2 to 16, 2 to 14, 2 to 12, 2 to 10, 2 to 8, 2 to 6, 2 to 4, 4 to 20, 4 to 18, 4 to 16, 4 to 14, 4 to 12, 4 to 10, 4 to 8, or 4 to 6 pathogen-derived antigenic polypeptides or tumor-derived antigenic polypeptides, but with no limitations thereto, and it will be apparent to those skilled in the art that selection may be made of a sufficient number to cause an immune response.

As used herein, the term "pathogen" refers to a microorganism that parasitizes a host and causes disease, and examples thereof include viruses, Rickettsia, bacteria, fungi, protozoa, and the like.

The terms "polypeptide" and "protein", as used herein, are used interchangeably herein to refer to a polymer of amino acid residues. Polypeptides and proteins also apply to analogs or mimetics of the naturally occurring amino acid polymer as well as amino acid polymers in which one or more amino acid residues are the corresponding naturally occurring amino acids. Polypeptides and proteins may also include polymers of amino acids that have been modified or phosphorylated to form glycoproteins, for example, by addition of carbohydrate moieties.

The polypeptide or protein of the present disclosure can be synthesized by a synthetic method known in the art, for example, by transforming an expression vector comprising a nucleic acid molecule expressing the protein into a host cell to synthesize the recombinant protein, or by solid-phase synthesis technology (solid-phase synthesis). synthesis techniques) (Merrifield, J. Amer. Chem. Soc. 85:2149-54 (1963); Stewart, et al., Solid Phase Peptide Synthesis, 2nd. ed., Pierce Chem. Co.: Rockford, 111 (1984)).

The antigenic polypeptide derived from a pathogen of the present disclosure can serve as an antigen for antibody production, and as long as it is an antigenic polypeptide derived from a pathogen, various selections are possible regardless of its type.

In an embodiment of the present disclosure, the pathogen is selected from the group consisting of viruses, bacteria, Rickettsia, fungi, and protozoa, but is not limited thereto.

In an embodiment of the present disclosure, the virus may be Human papillomavirus (HPV), hepatitis B virus (HBV), hepatitis C virus (HCV), human immunodeficiency virus (HIV), MERS-COV, SARS-COV-2, Zika virus, HPV, norovirus, rotavirus, influenza virus, parvo virus, adenovirus, herpes simplex virus (HSV), porcine reproductive and respiratory syndrome virus (PRRSV), swine fever virus, porcine circovirus (PCV), porcine epidemic diarrhea virus (PEDV), foot-and-mouth disease virus, Newcastle virus, birnavirus, or viral hemorrhagic septicemia virus (VHSV), but is not limited thereto.

In an embodiment of the present disclosure, the bacteria may be Escherichia coli, Clostridium perfringens, Campylobacter fetus jejuni, Mycobacterium paratuberculosis, Mycobacterium bovis, Clostridium tetani, Salmonella gallinarum, Staphylococcus aureus, Mycoplasma gallisepticum, Haemophilus gallisepticum parasuis, Lawsonia intracellularis, Bordetella bronchiseptica, Pasteurella multocida, or Rhodococcus equi, but are not limited thereto.

In an embodiment of the present disclosure, the *Rickettsia* is *Rickettsia rickettsia, Orientia tsutsugamushi, Coxiella burnetii, Rickettsia prowazekii,* or *Rickettsia rickettsia,* but is not limited thereto.

In an embodiment of the present disclosure, the fungus is *Candida* spp., *Mucor* spp., *Rhizopus* spp., or *Aspergillus* spp., but is limited thereto not.

The protozoa is *Cryptosporidium, Eimeria, trypanosoma, Plasmodium,* or *Toxoplasma,* but is not limited thereto.

In an embodiment of the present disclosure, the pathogen-derived antigenic polypeptide is, in the case of birds, VP2, VP3, VP4 protein of Infectious bursal disease virus (IBDV), or a combination thereof; glycoprotein B, glycoprotein I, glycoprotein D, glycoprotein E, glycoprotein C, or a combination thereof of Infectious laryngotracheitis virus (ILTV); fusion protein of Newcastle disease virus (NDV-F); avian influenza virus HA (hemagglutinin), NA (neuraminidase), M2e protein, or a combination thereof; S1, S2 protein of Infectious bronchitis virus (IBV), or a combination thereof; OMP (outer membrane protein) of poultry typhus (*Salmonella gallinarum*); Net-B, PFO protein of *Clostridium perfringens*; or a combination thereof, but with no limitations thereto.

In an embodiment of the present disclosure, the pathogen-derived antigenic polypeptide is, in the case of pigs, VP2, VP4, or VP6 protein of rotavirus, or a combination thereof; VP1, VP2, VP3, or VP4 protein of P1 protein of foot and mouth disease virus (FMDV), or a combination thereof; VP2 protein of parvovirus; protein E, ORF3, or protein M of porcine reproductive and respiratory syndrome virus (PRRSV) or a combination thereof; E1 or E2, classical swine fever virus (CSFV) or a combination thereof; capsid protein of circovirus type 2 (PCV2); k88, k99, or 987p protein *Escherichia coli,* or a combination thereof; OMP H (outer membrane protein H) of *Pasteurella multocida*; and the like, but is not limited thereto.

In an embodiment of the present disclosure, the pathogen-derived antigenic polypeptide is, in the case of dogs: glycoprotein G, nucleoprotein N, phosphoprotein P, matrix protein M, or RNA polymerization of rabies virus. enzyme L, or a combination thereof; HA protein or F protein of canine distemper virus, or a combination thereof; and the like, but with no limitations thereto.

In an embodiment of the present disclosure, the pathogen-derived antigenic polypeptide is a receptor binding domain (RBD) of the spike protein displayed on SARS-CoV 2.

In an embodiment of the present disclosure, the pathogen-derived antigenic polypeptide is M2e.

M2e refers to the matrix protein 2 ectodomain found in most influenza viruses. Since M2e is an evolutionarily conserved protein in influenza viruses, it is a promising candidate for constructing a universal vaccine against most influenza viruses.

In an embodiment of the present disclosure, the M2e includes the amino acid sequence of SEQ ID NO: 3, 4, 5, or 6.

In an embodiment of the present disclosure, the tumor-derived antigen includes a tumor-associated antigen (TAA) and a tumor-specific antigen (TSA).

The tumor-associated antigen (TAA) is a self-antigen that is abnormally overexpressed in tumors. The self-antigens can be eliminated by T cells that recognize them through central tolerance and peripheral tolerance mechanisms.

The tumor-specific antigen (TSA) includes a neoantigen that is caused by a mutation or genetic alteration that changes the amino acid of a protein and an oncoviral antigen of a virus. The neoantigen may be divided into a shared neoantigen and a private neoantigen that differs from one person to another.

More specifically, the tumor-derived antigen may be selected from the group consisting of M30, MAGE-1, MAGE-2, MAGE-3, MAGE-12, BAGE, GAGE, NY-ESO-1, tyrosinase, TRP-1, TRP-2, gp100, MART-1, MCIR, Ig idiotype, CDK4, Caspase-B, beta-catenin, CLA, BCR/ABL, mutated p21/ras, mutated p53, proteinase 3, WT1, MUC-1, Her2/neu, PAP, PSA, PSMA, G250, HPV E6/E7, EBV LMP2a, CEA, alpha-Fetoprotein, 5T4, and onco-trophoblast glycoprotein, but with no limitations thereto. It should be understood to a person skilled in the art that various antigens capable of being applied to cancer vaccines in the field are available.

In an embodiment of the present disclosure, the M30 may include the amino acid sequence of SEQ ID NO: 8 (i.e. PSKPSFQEFVDWENVSPELNSTDQPFL) or SEQ ID NO: 16 (i.e. VDWENVSPELNSTDQ). The M30 may also be encoded by a nucleic acid molecule including the nucleotide sequence of any one of SEQ ID NOS: 9 to 14, but are not limited to.

In an embodiment of the present disclosure, the tumor (or cancer) may include breast cancer, head and neck cancer, bladder cancer, stomach cancer, rectal/colon cancer, pancreatic cancer, lung cancer, melanoma, prostate cancer, kidney cancer, liver cancer, biliary tract cancer, cervical cancer, thyroid cancer, and the like, but are not limited thereto.

In an embodiment of the present disclosure, the BP26 and the antigenic polypeptide are linked or indirectly through a linker (e.g., an amino acid linker) to each other.

As used herein, the term "linker" refers to a peptide inserted between a protein and a protein so that, when a fusion protein is made by linking two proteins, the structural flexibility of these proteins or the activity of each protein can be enhanced. No limitations are imparted to the linker as long as it does not inhibit the activity of each protein to be fused and does not cause an unnecessary immune response. Specifically, the linker may be a peptide linker consisting of 1 to 20 amino acids, and more specifically 1 to 6 amino acids.

A person skilled in the art could conceive that a linker may be used between functional moieties to be usually fused in the production of a fusion protein and would understand that there are different kinds of linkers having different characteristics, for example, a flexible amino acid linker, a non-flexible linker, and a cleavable amino acid linker. The linkers have been used for the purpose of increasing expression levels, improving biological activity, and enabling targeting, or modifying pharmacokinetics of the fusion protein, or in order to increase stability and improve folding property of the fusion protein.

Accordingly, according to a concrete embodiment of the present disclosure, the fusion protein may include at least one linker, for example, at least one linker selected from a flexible amino acid linker, a non-flexible linker and a cleavable amino acid linker.

The linker may consist of an amino acid sequence represented by the general formula (GnSm)p or (SmGn)p, SEQ ID NOs: 17-19:

wherein, n is an integer of 1 to 7;

m is an integer of 0 to 7;

wherein the sum of n and m is 8 or less; and p is an integer of 1 to 7.

In another embodiment of the present disclosure, the linker is n=1 to 5, and m=0 to 5. In another embodiment, the linker is GGGGS, SEQ ID NO: 17. In another concrete embodiment, the linker is GGGG, SEQ ID NO: 18, GGGSG, SEQ ID NO: 19.

In another embodiment of the present disclosure, the linker is Cathepsin-cleavable liker LQ (Leucine-Glycine).

In another embodiment of the present disclosure, the linker may be VDGS or ASGS, but is not limited thereto.

In an embodiment of the present disclosure, the polypeptides are continuously or discontinuously linked in the fusion protein.

In the present disclosure, the number of antigenic polypeptides in the fusion protein can be controlled to regulate the immune response. According to an embodiment of the present disclosure, a fusion protein in which eight M2e polypeptides or six M30 polypeptides are linked shows an excellent immune-inducing effect.

As used herein, the term "tandem repeat structure" refers to a configuration in which two or more antigenic polypeptides included in the fusion protein of the present disclosure are connected in series continuously or non-continuously by a linker.

According to an embodiment of the present disclosure, BP26 of the present disclosure may be in the form of a fusion protein having four or eight M2e monomers linked by a linker, wherein the fusion protein can self-assemble to form a nanoarchitecture.

Provided according to another aspect of the present disclosure is a nucleic acid molecule including a nucleotide sequence encoding for the fusion protein.

As used herein, the term "nucleic acid" is intended to comprehensively encompass DNA (gDNA and cDNA) and RNA molecules, and nucleotides as basic constituent units in the nucleic acid molecules include naturally occurring nucleotides, and analogues with modified sugars or bases (Scheit, Nucleotide Analogs, John Wiley, New York (1980); and Uhlman & Peyman, Chemical Reviews, 90:543-584 (1990)). So long as it codes for the amino acid sequence accounting for the fusion protein, any nucleotide sequence may be employed in an embodiment of the present disclosure, and it would be obvious to a person skilled in the art that the nucleotide is not limited to a specific nucleotide sequence. This is because the variation in nucleotide sequences may not lead to change in protein sequences through expression. This is called codon degeneracy. Accordingly, the nucleotide sequence includes a nucleotide sequence including functionally equivalent codons, or codons encoding the same amino acid (for example, six codons encode arginine or serine due to codon degeneracy) or codons encoding a biologically equivalent amino acid.

Considering the above-described mutation having biologically equivalent activity, it should be construed that the nucleic acid molecules of the present disclosure encoding the amino acid sequences responsible for the constitution of the fusion protein also encompass sequences exhibiting substantial identity therewith. When the sequence of the present disclosure and any other sequence are correspondingly aligned as much as possible and the aligned sequence is analyzed using algorithms commonly used in the art, the sequences exhibiting substantial identity therewith refers to sequences showing an identity of:

at least 60% (e.g., 60%, 61%, 62%, 63%, 64%, 65%, 66%, 67%, 68%, or 69%), more preferably at least 70% (e.g., 70%, 71%, 72%, 73%, 74%, 75%, 76%, 77%, 78%, or 79%), even more preferably at least 80% (e.g., 80%, 81%, 82%, 83%, 84%, 85%, 86%, 87%, 88%, or 89%), and most preferably at least 90% (e.g., 90%, 91%, 92%, 93%, 94%, 95%, 96%, 97%, 98%, 99%, or 100%). All integers between 70% and 100% (both inclusive) and decimals therebetween are included within the scope of the present disclosure with respect to % identity.

Methods of alignment for sequence comparison are known in the art. Various methods and algorithms for alignment are disclosed in Smith and Waterman, Adv. Appl. Math. 2:482(1981); Needleman and Wunsch, J. Mol. Bio. 48:443(1970); Pearson and Lipman, Methods in Mol. Biol. 24:307-31(1988); Higgins and Sharp, Gene 73:237-44 (1988); Higgins and Sharp, CABIOS 5:151-3(1989); Corpet et al., Nuc. Acids Res. 16:10881-90(1988); Huang et al., Comp. Appl. BioSci. 8:155-65(1992) and Pearson et al., Meth. Mol. Biol. 24:307-31(1994), but with no limitations thereto.

The NCBI Basic Local Alignment Search Tool (BLAST) (Altschul et al., J. Mol. Biol. 215:403-10(1990)) is accessible from the NBCI (National Center for Biological Information) and may be used in connection with sequence analysis programs, such as blastp, blastn, blastx, tblastn, and tblastx, on the Internet. BLAST may be accessed through the BLAST webpage of the NCBI's website. The method for comparing sequence homology using such a program is available from the BLAST help page of the NCBI's website.

Another aspect of the present disclosure provides a recombinant vector comprising a nucleic acid molecule encoding for the fusion protein.

The term "vector", as used herein, refers to a means for expressing a gene of interest in a host cell. Examples of the vector available herein include plasmid vectors; cosmid vectors; and viral vectors such as bacteriophage vectors, adenovirus vectors, retrovirus vectors, and adeno-associated virus vectors.

In an embodiment of the present disclosure, the nucleic acid molecule encoding the fusion protein in the vector of the present disclosure is operatively linked to a promoter in the vector.

As used herein, the term "operatively linked" refers to a functional linkage between a nucleic acid expression regulation sequence (e.g., a promoter, a signal sequence, or an array of transcription regulation factor binding sites) and another nucleic acid sequence, whereby the control sequence controls the transcription and/or translation of the nucleic acid sequence.

The vector system of the present disclosure can be constructed by various methods known in the art, and specific methods thereof are disclosed in Sambrook, et al., Molecular Cloning, A Laboratory Manual, Cold Spring Harbor Laboratory Press (2001), the teachings of which are incorporated herein by reference.

The vector of the present disclosure can typically be constructed as a vector for gene cloning or a vector for protein expression. In addition, the vector of the present disclosure can be constructed, with a prokaryotic cell or a eukaryotic cell serving as a host.

By way of example, when the vector of the present disclosure is an expression vector, with an eukaryotic cell serving as a host cell, promoters derived from genomes of mammalian cells (e.g., metallothionein promoter, β-actin promoter, human hemoglobin promoter, and human muscle creatinine promoter) or promoters derived from mammalian viruses (e.g., adenovirus late promoter, vaccinia virus, 7.5K promoter, SV40 promoter, cytomegalovirus promoter, HSV tk promoter, mouse mammary tumor virus (MMTV) promoter, HIV LTR promoter, Moloney virus promoter, Epstein Barr Virus (EBV) promoter, Rous Sarcoma Virus (RSV)

promoter) may be available. Generally, the vectors include a polyadenylate sequence as a transcriptional termination sequence.

The vector of the present invention may be fused to another sequence to facilitate the purification of a polypeptide expressed therefrom. Examples of the sequence to be used for the fusion include glutathione S-transferase (Pharmacia, USA), maltose binding protein (NEB, USA), FLAG (IBI, USA), and 6× His (hexahistidine; Qiagen, USA).

The vector of the present disclosure includes, as a selective marker, an antibiotic-resistant gene that is ordinarily used in the art, and may include resistant genes against ampicillin, gentamycin, carbenicillin, chloramphenicol, streptomycin, kanamycin, geneticin, neomycin, and tetracycline.

Another aspect of the present disclosure provides a host cell comprising the vector.

So long as it is known in the art to stabilize the vector of the present disclosure and continually clone and express the vector, any host cell may be employed in the present disclosure.

Examples of the eukaryotic host cells suitable for the vector include monkey kidney cells 7 (COS7), NSO cells, SP2/0, Chinese hamster ovary (CHO) cells, W138, baby hamster kidney (BHK) cells, MDCK, myeloma cell lines, HuT 78 cells, and HEK-293 cells, but are not limited thereto.

As used herein, the term "transformed", "transduced", or "transfected" refers to pertaining to a process for delivering or introducing an exogenous nucleic acid into a host cell. A "transformed", "transduced", or "transfected" cell is one which has been transformed, transduced, or transfected with an exogenous nucleic acid. The cell includes the primary subject cell and its progenies resulting from passages.

Provided according to another aspect of the present disclosure is a nanoarchitecture including the fusion protein.

In an embodiment of the present disclosure, the nanoarchitecture includes two or more monomers of the fusion protein.

In an embodiment of the present disclosure, the nanoarchitecture may include 2 to 20 monomers of the fusion protein. More specifically, the nanoarchitecture includes 8 or 16 monomeric fusion protein.

In an embodiment of the present disclosure, the nanoarchitecture includes a hexadecamer formed by combining two octamers formed of the eight fusion proteins.

In an embodiment of the present disclosure, the nanoarchitecture includes a hollow structure. The term "hollow structure" refers to a structure having an empty inside. According to an embodiment of the present disclosure, the nanoarchitecture of the present disclosure represents a hollow barrel-type structure.

According to an embodiment of the present disclosure, the hollow structure of the nanoarchitecture has smaller pore sizes as the fusion protein included in the nanoarchitecture contains more antigenic polypeptides.

In an embodiment of the present disclosure, the nanoarchitecture is designed to display the antigen on the surface thereof. According to an embodiment of the present disclosure, the nanoarchitecture of the present disclosure displays the epitope of the M2e or M30 antigen on the surface thereof.

Since the fusion protein accounting for the nanoarchitecture is the same as the fusion protein including BP26 and the antigenic polypeptide, the overlapping common contents therebetween are omitted in order to avoid undue complexity of the specification.

Another aspect of the present disclosure provides a vaccine composition including the fusion protein, the nanoarchitecture, or a combination thereof.

In an embodiment of the present disclosure, the vaccine composition is a vaccine composition for prevention of a viral disease caused by at least one selected from the group consisting of HPV (human papillomavirus), HBV (hepatitis B virus), HCV (hepatitis C virus), HIV (human immunodeficiency virus), MERS-COV, SARS-COV-2, Zika virus, HPV, norovirus, rotavirus, influenza virus, herpes simplex virus (HSV), porcine reproductive and respiratory syndrome virus (PRRSV), porcine cholera virus, porcine circovirus (PCV), porcine epidemic diarrhea virus (PEDV), foot-and-mouth disease virus, Newcastle virus, and viral hemorrhagic septicemia virus (VHSV), but with no limitations thereto.

In an embodiment of the present disclosure, the vaccine composition is a vaccine composition for preventing infection from an infectious pathogen.

In a concrete embodiment of the present disclosure, the vaccine composition is a vaccine for prevention of a bacterial disease caused by at least one selected from the group consisting of *Escherichia coli, Clostridium perfringens, Campylobacter fetus jejuni, Mycobacterium paratuberculosis, Mycobacterium bovis, Clostridium tetani, Salmonella gallinarum, Staphylococcus aureus, Mycoplasma gallisepticum, Haemophilus parasuis, Lawsonia intracellularis, Bordetella bronchiseptica, Pasteurella multocida* and *Rhodococcus equi*, but with no limitations thereto.

In an embodiment of the present disclosure, the vaccine composition is a vaccine for prevention of a rickettsial disease caused by at least one selected from the group consisting of *Rickettsia rickettsia, Orientia tsutsugamushi, Coxiella burnetii, Rickettsia prowazekii*, and *Rickettsia typhi*, but with no limitations thereto.

In an embodiment of the present disclosure, the vaccine composition is a vaccine for prevention of a fungal disease caused by at least one selected from the group consisting of *Candida* spp., *Mucor* spp., *Rhizopus* spp., and *Aspergillus* spp., but with no limitations thereto.

In an embodiment of the present disclosure, the vaccine composition is a vaccine for prevention of a protozoal disease caused by at least one selected from the group consisting of *Cryptosporidium, Eimeria, Trypanosoma, Plasmodium*, and *Toxoplasma.*, but with no limitations thereto.

According to an embodiment of the present disclosure, the vaccine composition is a vaccine composition for prevention of influenza viral disease.

In an embodiment of the present disclosure, the vaccine composition is for a cancer vaccine.

The cancer vaccine of the present disclosure can be used to elicit an immune response against cancer or a tumor in a mammal or subject in need thereof. The induced immune response can prevent or treat cancer or tumor growth.

The induced immune response can prevent and/or reduce metastasis of cancer or tumor cells.

Depending on the antigen used in the vaccine, the cancer includes breast cancer, head and neck cancer, bladder cancer, stomach cancer, rectal/colon cancer, pancreatic cancer, lung cancer, melanoma, prostate cancer, kidney cancer, skin cancer, liver cancer, biliary tract cancer, cervical cancer, thyroid cancer, blood cancer (e.g., leukemia, lymphoma, myeloma), and the like, but is not limited thereto.

In an embodiment of the present disclosure, the administered vaccine can mediate the removal of tumor cells or inhibit their growth by increasing an inflammatory response through (1) blockage of the production of monocyte chemoattractant protein-1 (MCP-1) to delay bone marrow-derived suppressor cells (MDSC) and induction of humoral immunity via a B cell response inhibitory of tumor growth, (2) increasing of cytotoxic T lymphocytes such as CD8+ (CTL) that attack and kill tumor cells; (3) increasing of helper T cell responses; and (4) IFN-γ and TFN-α, and preferably through all of them.

In some embodiments, the immune response may result in a humoral immune response and/or an antigen-specific cytotoxic T lymphocyte (CTL) response that does not cause damage to or inflammation of various tissues or systems (e.g., the brain or nervous system, etc.) in a subject to whom the vaccine is administered.

In an embodiment of the present disclosure, the composition may additionally include an adjuvant.

As used herein, the term "adjuvant" refers to an additive to increase an immune response, which is generally used together with an antigen for antibody production and enhancement of immunity. Specifically, the adjuvant may be selected from the group consisting of alum, Freund's complete adjuvant, Freund's incomplete adjuvant, LPS, poly IC, poly AU, lysolecithin, pluronic polyol, polyanion, oil or hydrocarbon emulsion, keyhole limpet hemocyanin, and dinitrophenol, but with no limitations thereto.

In an embodiment of the present disclosure, the adjuvant is an immunostimulatory single- or double-stranded oligonucleotide, an immunostimulatory small molecule compound, or a combination thereof.

In an embodiment of the present disclosure, the immunostimulatory single-stranded or double-stranded oligonucleotide is known as a useful adjuvant (immunoadjuvant). The oligonucleotides often contain a CpG motif (a dinucleotide sequence including an unmethylated cytosine linked to a guanosine). Oligonucleotides including a TpG motif, a palindrome arrangement, a plurality of consecutive thymidine nucleotides (e.g., TTTT), a plurality of consecutive cytosine nucleotides (e.g., CCCC), or a poly(dG) arrangement are also known adjuvants like double-stranded RNA. Any of a variety of immunostimulatory oligonucleotides can be used in the present disclosure, without limitations.

The oligonucleotide is typically 10-100 nucleotides long, for example 15-50 nucleotides, 20-30 nucleotides, or 25-28 nucleotides long. It is typically a single chain.

The oligonucleotide may include only natural nucleotides, only non-natural nucleotides, or a mixture of both. For example, the oligonucleotide may contain one or more phosphorothioate linkages, and/or one or more 2'-O-methyl modifications.

In a specific embodiment of the present disclosure, the single- or double-stranded oligonucleotide is a CpG oligonucleotide, a STING active oligonucleotide, or a combination thereof.

As used herein, the term "stimulator of interferon genes" or "STING" refers to a factor that stimulates interferon genes, playing an important role in innate immunity. STING includes five putative transmembrane (TM) regions that reside predominantly in the endoplasmic reticulum (ER), induce type I IFG, and is able to activate NF-kB and IRF3 transcription pathways to induce type I IFN and to exert a potent anti-viral state following expression (see U.S. patent application Ser. No. 13/057,662 and PCT/US2009/052767). Loss of STING reduced the ability of polyIC to activate type I IFN and rendered murine embryonic fibroblasts lacking STING (−/− MEFs) generated by targeted homologous recombination, susceptible to vesicular stomatitis virus (VSV) infection. In the absence of STING, DNA-mediated type I IFN responses were inhibited, indicating that STING may play an important role in recognizing DNA from viruses, bacteria, and other pathogens which can infect cells. Yeast-two hybrid and co-immunoprecipitation studies indicated that STING interacts with RIG-I and with Ssr2/TRAPβ, a member of the translocon-associated protein (TRAP) complex required for protein translocation across the ER membrane following translation. RNAi ablation of TRAPβ inhibited STING function and impeded the production of type I IFN in response to polyIC. Further experiments showed that STING itself binds nucleic acids including single- and double-stranded DNA such as from pathogens and apoptotic DNA, and plays a central role in regulating proinflammatory gene expression in inflammatory conditions such as DNA-mediated arthritis and cancer. Various new methods of, and compositions for, upregulating STING expression or function are described herein along with further characterization of other cellular molecule which interact with STING. These discoveries allow for the design of new adjuvants, vaccines and therapies to regulate the immune system and other systems.

The STING-activating oligonucleotide may be a nucleic acid molecule that binds to STING to increase the STING function. The STING-binding nucleic acid molecule may be a single-stranded DNA between 40 and 150 base pairs in length or a double-stranded DNA between 40 and 150, 60 and 120, 80 and 100, or 85 and 95 base pairs in length or longer. The STING-binding nucleic acid molecule may be nuclease-resistant, e.g., made up of nuclease-resistant nucleotides. It may also be associated with a molecule that facilitates transmembrane transport. In these methods, the disease or disorder can be a DNA-dependent inflammatory disease. Also described herein is a method for treating cancer in a subject having a cancerous tumor infiltrated with inflammatory immune cells. This method may include a step of administering to the subject an amount of a pharmaceutical composition containing an agent which downregulates the function or expression of STING and a pharmaceutically acceptable carrier.

More specifically, the oligonucleotide is an antisense oligonucleotide, a CpG oligonucleotide, or a combination thereof.

As used herein, the term "CpG oligonucleotide" (CpG oligodeoxynucleotide, or CpG ODN) refers to a short single-stranded DNA molecule, known as an immunostimulant, including unmethylated cytosine triphosphate deoxynucleotide ("C") and guanine triphosphate deoxynucleotide ("G"). The CpG serves as an adjuvant that enhances the immune response of dendritic cells when included as a component of the nano-vaccine of the present disclosure.

The immunostimulatory low molecular weight compound is also called a small molecule adjuvant, and includes a synthetic low-molecular adjuvant and a natural low-molecular adjuvant. Examples of the immunostimulatory low molecular weight compound or low molecular weight adjuvant include monophosphoryl lipid A, Muramyl dipeptide, Bryostatin-1, Mannide monooleate (Montanide ISA 720), Squalene, QS21, Bis-(3',5')-cyclic dimeric guanosine monophosphate, PAM2CSK4, PAM3CSK4, Imiquimod, Resiquimod, Gardiquimod, cl075, cl097, Levamisole, 48/80, Bupivacaine, Isatoribine, Bestatin, Sm360320, and Loxoribine, but are not limited thereto. For small molecule adjuvants, reference may be made to Flower D R et al. (Expert Opin Drug Discov. 2012 September; 7(9):807-17.).

The vaccine composition of the present disclosure may further include a pharmaceutically acceptable carrier, excipient, or diluent.

As used herein, the term "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered. Suitable carriers for the vaccine are known to those skilled in the art and include, but are not limited to, proteins, sugars, and the like. Such carriers may be aqueous or non-aqueous solutions, suspensions, and emulsions. Non-aqueous carriers include propylene glycol, polyethylene glycol, edible oils such as olive oil, and injectable organic esters such as ethyl oleate. Aqueous carriers include water, alcohol/aqueous solutions, emulsions or suspensions, including saline and buffered media.

A suitable dosage of the vaccine composition of the present disclosure may vary depending on the species of the individual, the breed of the individual, the formulation method, the mode of administration, the age, weight, sex, vaccination history, food, administration time, route of administration, excretion rate and reaction sensitivity of the individual.

For example, the dosage of the vaccine composition of the present disclosure may be 0.1 ml to 10 ml. The dosage of the vaccine composition of the present disclosure may be 0.1 ml to 0.5 ml, more specifically 0.3 ml to 0.5 ml in avian species. The dosage of the vaccine composition of the present disclosure may be 0.2 ml to 3.0 ml, more specifically 0.3 ml to 2.0 ml, most specifically 0.5 ml to 1.0 ml in cat, dog and horse species. The dosage of the vaccine composition of the present disclosure may be 0.2 ml to 5.0 ml, more specifically 0.3 ml to 3.0 ml, more specifically 0.5 ml to 2.0 ml for bovine and porcine species.

In addition, the amount of antigen in the dosage of the vaccine composition may be 1 to 100 µg, 5 to 50 µg, 5 to 30 µg, 5 to 25 µg, 10 to 50 µg, 10 to 40 µg, 10 to 30 µg, or 10 to 25 µg. According to an embodiment of the present disclosure, the amount of antigen in the dosage of the vaccine composition dose is 10 to 30 µg.

The subject to which the present disclosure can be applied may be any animal, especially, mammals, such as humans, mice, rats, hamsters, guinea pigs, rabbits, cats, dogs, monkeys, cattle, horses, pigs; and livestock including birds, such as chickens, ducks, turkeys, and the like. Most preferred subjects are livestock or humans.

The vaccine composition may be freeze-dried or formulated as a liquid formulation according to any means suitable in the art. Non-limiting examples of formulations in liquid form include solutions, suspensions, syrups, slurries, and emulsions. Suitable liquid carriers include all suitable organic or inorganic solvents, for example, water, alcohol, saline, buffered saline, physiological saline, dextrose solution, water propylene glycol solution, and the like, preferably in a sterile form.

Vaccine compositions may be formulated in a neutral or salt form. Pharmaceutically acceptable salts include acid addition salts (formed with the free amino group of the active polypeptide), which are formed together with inorganic acids such as hydrochloric or phosphoric acid, or organic acids such as acetic acid, oxalic acid, tartaric acid, mandelic acid, and the like. In addition, salts formed from free carboxyl groups may be derived from inorganic bases such as sodium, potassium, ammonium, calcium or ferric hydroxide, and organic bases such as isopropylamine, triethylamine, 2-ethylamino ethanol, histidine, procaine, and the like.

The vaccine composition is preferably formulated for inoculation or injection into a subject. For injection, the vaccine composition of the present disclosure may be formulated in an aqueous solution, e.g., water or alcohol, or in a physiologically suitable buffer, e.g., Hanks' solution, Ringer's solution, or physiological saline buffer. The solution may contain a formulation agent such as a suspending agent, a preservative, a stabilizer, and/or a dispersant. Injectable formulations may also be prepared as solid form preparations which are converted shortly before use into liquid form preparations suitable for injection, for example, by reconstitution with a suitable vehicle such as sterile water, saline or alcohol prior to use.

The vaccine composition may also be formulated into sustained release vehicles or depot preparations. Such long-acting formulations can be administered by inoculation or implantation (for example subcutaneously or intramuscularly) or by injection. Thus, for example, the vaccine compositions can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers.

Administration of the vaccine compositions can be achieved by infusion or injection (e.g., intravenously, intramuscularly, intracutaneously, subcutaneously, intrathecal, intraduodenally, intraperitoneally, and the like). The vaccine compositions can also be administered intranasally, vaginally, rectally, orally, or transdermally. Additionally, vaccine compositions can be administered by "needle-free" delivery systems. Preferably, the compositions are administered by intradermal injection. Administration can be at the direction of a physician or physician assistant.

The injections can be split into multiple injections, with such split inoculations administered preferably substantially concurrently. When administered as a split inoculation, the dose of the immunogen is preferably, but not necessarily, proportioned equally in each separate injection. If an adjuvant is present in the vaccine composition, the dose of the adjuvant is preferably, but not necessarily, proportioned equally in each separate injection. The separate injections for the split inoculation are preferably administered substantially proximal to each other on the patient's body. In some preferred aspects, the injections are administered at least about 1 cm apart from each other on the body. In some preferred aspects, the injections are administered at least about 2.5 cm apart from each other on the body. In highly preferred aspects, the injections are administered at least about 5 cm apart from each other on the body. In some aspects, the injections are administered at least about 10 cm apart from each other on the body. In some aspects, the injections are administered more than 10 cm apart from each other on the body, for example, at least about 12.5. 15, 17.5, 20, or more cm apart from each other on the body. Primary immunization injections and booster injections can be administered as a split inoculation as described and exemplified herein.

Various alternative pharmaceutical delivery systems can be employed. Non-limiting examples of such systems include liposomes and emulsions. Certain organic solvents such as dimethylsulfoxide also can be employed. Additionally, the vaccine compositions can be delivered using a sustained-release system, such as semipermeable matrices of solid polymers containing the therapeutic agent. The various sustained-release materials available are well known by those skilled in the art. Sustained-release capsules can, depending on their chemical nature, release the vaccine compositions over a range of several days to several weeks to several months.

To prevent recurrence of cancer in a patient who is in cancer remission, a therapeutically effective amount of the vaccine composition is administered to the subject. A therapeutically effective amount will provide a clinically significant increase in the number of antigen-specific cytotoxic T-lymphocytes (CD8+) in the patient, as well as a clinically significant increase in the cytotoxic T-lymphocyte response to the antigen, as measured by any means suitable in the art. In the patient, on the whole, a therapeutically effective amount of the vaccine composition will destroy residual microscopic disease and significantly reduce or eliminate the risk of recurrence of cancer in the patient.

The effective amount of the vaccine composition can be dependent on any number of variables, including without limitation, the species, breed, size, height, weight, age, overall health of the patient, the type of formulation, the mode or manner or administration, or the presence or absence of risk factors that significantly increase the likelihood that the breast cancer will recur in the patient. Such risk factors include, but are not limited to the type of surgery, status of lymph nodes and the number positive, the size of the tumor, the histologic grade of the tumor, the presence/absence of hormone receptors (estrogen and progesterone receptors), HER2/neu expression, lymphovascular invasion, and genetic predisposition (BRCA 1 and 2). In some preferred aspects, the effective amount is dependent on whether the patient is lymph node positive of lymph node negative, and if the patient is lymph node positive, the number and extent of the positive nodes. In all cases, the appropriate effective amount can be routinely determined by those of skill in the art using routine optimization techniques and the skilled and informed judgment of the practitioner and other factors evident to those skilled in the art. Preferably, a therapeutically effective dose of the vaccine compositions described herein will provide the therapeutic preventive benefit without causing substantial toxicity to the subject.

Toxicity and therapeutic efficacy of the vaccine compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Vaccine compositions that exhibit large therapeutic indices are preferred. Data obtained from cell culture assays and animal studies can be used in formulating a range of dosage for use in patients. The dosage of such vaccine compositions lies preferably within a range of circulating concentrations that include the ED50 with little or no toxicity. The dosage can vary within this range depending upon the dosage form employed and the route of administration utilized.

Toxicity information can be used to more accurately determine useful doses in a specified subject such as a human. The treating physician can terminate, interrupt, or adjust administration due to toxicity, or to organ dysfunctions, and can adjust treatment as necessary if the clinical response is not adequate, to improve the response. The magnitude of an administrated dose in the prevention of recurrent breast cancer will vary with the severity of the patient's condition, relative risk for recurrence, or the route of administration, among other factors. The severity of the patient's condition can, for example, be evaluated, in part, by standard prognostic evaluation methods.

The vaccine compositions can be administered to a patient on any schedule appropriate to induce and/or sustain protective immunity against cancer relapse. For example, patients can be administered a vaccine composition as a primary immunization as described and exemplified herein, followed by administration of a booster to bolster and/or maintain the protective immunity. In some aspects, patients can be administered the vaccine compositions 1, 2, or more times per month.

The vaccine administration schedule, including primary immunization and booster administration, can continue as long as needed for the patient, for example, over the course of several years, to prolong the lifetime of the patient. In some aspects, the vaccine schedule includes more frequent administration at the beginning of the vaccine regimen, and includes less frequent administration (e.g., boosters) over time to maintain the protective immunity.

The vaccine can be administered at lower doses at the beginning of the vaccine regimen, with higher doses administered over time. The vaccines can also be administered at higher doses at the beginning of the vaccine regimen, with lower doses administered over time.

The frequency of primary vaccine and booster administration and dose of the antigen administered can be tailored and/or adjusted to meet the particular needs of individual patients, as determined by the administering physician according to any means suitable in the art.

The vaccine composition according to an aspect of the present disclosure is a composition comprising the above-described fusion protein or nanoarchitecture. Thus, the common contents are omitted in order to avoid undue complexity of the specification. Administration of the vaccine compositions can be achieved by infusion or injection (e.g., intravenously, intramuscularly, intracutaneously, subcutaneously, intrathecal, intraduodenally, intraperitoneally, and the like). The vaccine compositions can also be administered intranasally, vaginally, rectally, orally, or transdermally. Additionally, vaccine compositions can be administered by "needle-free" delivery systems. Preferably, the compositions are administered by intradermal injection. Administration can be at the direction of a physician or physician assistant.

The injections can be split into multiple injections, with such split inoculations administered preferably substantially concurrently. When administered as a split inoculation, the dose of the immunogen is preferably, but not necessarily, proportioned equally in each separate injection. If an adjuvant is present in the vaccine composition, the dose of the adjuvant is preferably, but not necessarily, proportioned equally in each separate injection. The separate injections for the split inoculation are preferably administered substantially proximal to each other on the patient's body. In some preferred aspects, the injections are administered at least about 1 cm apart from each other on the body. In some preferred aspects, the injections are administered at least about 2.5 cm apart from each other on the body. In highly preferred aspects, the injections are administered at least about 5 cm apart from each other on the body. In some aspects, the injections are administered at least about 10 cm apart from each other on the body. In some aspects, the injections are administered more than 10 cm apart from each other on the body, for example, at least about 12.5. 15, 17.5, 20, or more cm apart from each other on the body. Primary immunization injections and booster injections can be administered as a split inoculation as described and exemplified herein.

Various alternative pharmaceutical delivery systems can be employed. Non-limiting examples of such systems include liposomes and emulsions. Certain organic solvents such as dimethylsulfoxide also can be employed. Additionally, the vaccine compositions can be delivered using a sustained-release system, such as semipermeable matrices of solid polymers containing the therapeutic agent. The various sustained-release materials available are well known by those skilled in the art. Sustained-release capsules can, depending on their chemical nature, release the vaccine compositions over a range of several days to several weeks to several months.

To prevent recurrence of cancer in a patient who is in cancer remission, a therapeutically effective amount of the vaccine composition is administered to the subject. A therapeutically effective amount will provide a clinically significant increase in the number of antigen-specific cytotoxic T-lymphocytes (CD8+) in the patient, as well as a clinically significant increase in the cytotoxic T-lymphocyte response to the antigen, as measured by any means suitable in the art. In the patient, on the whole, a therapeutically effective amount of the vaccine composition will destroy residual microscopic disease and significantly reduce or eliminate the risk of recurrence of cancer in the patient.

The effective amount of the vaccine composition can be dependent on any number of variables, including without limitation, the species, breed, size, height, weight, age, overall health of the patient, the type of formulation, the mode or manner or administration, or the presence or absence of risk factors that significantly increase the likelihood that the breast cancer will recur in the patient. Such risk factors include, but are not limited to the type of surgery, status of lymph nodes and the number positive, the size of the tumor, the histologic grade of the tumor, the presence/absence of hormone receptors (estrogen and progesterone receptors), HER2/neu expression, lymphovascular invasion, and genetic predisposition (BRCA 1 and 2). In some preferred aspects, the effective amount is dependent on whether the patient is lymph node positive of lymph node negative, and if the patient is lymph node positive, the number and extent of the positive nodes. In all cases, the appropriate effective amount can be routinely determined by those of skill in the art using routine optimization techniques and the skilled and informed judgment of the practitioner and other factors evident to those skilled in the art. Preferably, a therapeutically effective dose of the vaccine compositions described herein will provide the therapeutic preventive benefit without causing substantial toxicity to the subject.

Toxicity and therapeutic efficacy of the vaccine compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Vaccine compositions that exhibit large therapeutic indices are preferred. Data obtained from cell culture assays and animal studies can be used in formulating a range of dosage for use in patients. The dosage of such vaccine compositions lies preferably within a range of circulating concentrations that include the ED50 with little or no toxicity. The dosage can vary within this range depending upon the dosage form employed and the route of administration utilized.

Toxicity information can be used to more accurately determine useful doses in a specified subject such as a human. The treating physician can terminate, interrupt, or adjust administration due to toxicity, or to organ dysfunctions, and can adjust treatment as necessary if the clinical response is not adequate, to improve the response. The magnitude of an administrated dose in the prevention of recurrent breast cancer will vary with the severity of the patient's condition, relative risk for recurrence, or the route of administration, among other factors. The severity of the patient's condition can, for example, be evaluated, in part, by standard prognostic evaluation methods.

The vaccine compositions can be administered to a patient on any schedule appropriate to induce and/or sustain protective immunity against cancer relapse. For example, patients can be administered a vaccine composition as a primary immunization as described and exemplified herein, followed by administration of a booster to bolster and/or maintain the protective immunity. In some aspects, patients can be administered the vaccine compositions 1, 2 or more times per month.

The vaccine administration schedule, including primary immunization and booster administration, can continue as long as needed for the patient, for example, over the course of several years, to over the lifetime of the patient. In some aspects, the vaccine schedule includes more frequent administration at the beginning of the vaccine regimen, and includes less frequent administration (e.g., boosters) over time to maintain the protective immunity.

The vaccine can be administered at lower doses at the beginning of the vaccine regimen, with higher doses administered over time. The vaccines can also be administered at higher doses at the beginning of the vaccine regimen, with lower doses administered over time.

The frequency of primary vaccine and booster administration and dose of the antigen administered can be tailored and/or adjusted to meet the particular needs of individual patients, as determined by the administering physician according to any means suitable in the art.

The vaccine composition according to an aspect of the present disclosure is a composition comprising the above-described fusion protein or nanoarchitecture. Thus, the common contents are omitted in order to avoid undue complexity of the specification.

In an embodiment of the present disclosure, the vaccine composition is for preventing or treating cancer. When the vaccine composition is to prevent or treat cancer, the antigen of the fusion protein or nanoarchitecture as the active ingredient in the vaccine composition is a tumor-derived antigen.

The term "prevent" refers to any success or indicia of success in the forestalling of cancer recurrence/relapse in patients in clinical remission, as measured by any objective or subjective parameter, including the results of a radiological or physical examination.

Since the fusion protein and nanoarchitecture included in the vaccine composition are the same as the above-described fusion protein and nanoarchitecture, the common contents are omitted to avoid undue complexity of the specification.

According to another aspect thereof, the present disclosure provides a method for preventing or treating an infectious disease or cancer, the method comprising a step of administering the vaccine composition to a subject.

The subject to which the present disclosure can be applied may be any animal, especially, mammals, such as humans, mice, rats, hamsters, guinea pigs, rabbits, cats, dogs, monkeys, cattle, horses, pigs; and livestock including birds, such as chickens, ducks, turkeys, and the like. Most preferred subjects are livestock or humans.

Since the method for preventing or treating an infectious disease or cancer according to an aspect of the present disclosure includes administering the above-described vaccine composition to a subject, the common contents therebetween are omitted in order to avoid undue complexity of the specification.

Advantageous Effects of Invention

The features and advantages of the present disclosure are summarized as follows:

(a) The present disclosure provides a fusion protein including BP26 and an antigenic polypeptide.

(b) The present disclosure provides a nanoarchitecture including the fusion protein.

(c) When a vaccine composition comprising the fusion protein of the present disclosure, the nanoarchitecture, or a combination thereof is used, it is possible to effectively prevent or treat a pathogen or cancer, so that the vaccine composition can be available as a multipurpose vaccine platform.

solid/solid, (weight/volume) % for solid/liquid, and (volume/volume) % for liquid/liquid throughout the specification.

Animals, Cells, and Viruses

Female Balb/c mice were purchased from Orient Bio (Korea) and housed under pathogen-free conditions. Animal care and experimental procedures were approved by the Animal Experimental Ethics Committees of the Korea Advanced Institute of Science and Technology (KAIST) (Accreditation No.: KA2020-56). MDCK cells were cultured 37° C. in MEM medium (Welgene, Gyeongsan, Korea) supplemented with 1% penicillin/streptomycin and 10% heat-inactivated fetal bovine serum (FBS; Welgene) under a 5% $CO2$ condition. The influenza A viruses A/PR/8, A/CA/04/09 and A/Aquatic bird/Korea were used.

Example 1: Cloning, Expression, and Purification of BP26-M2e Recombinant Proteins The BP26 sequence is as follows (Table 1).

TABLE 1

| category | Sequence | SEQ ID NO. |
|---|---|---|
| BP26 | QENQMTTQPARIAVTGEGMMTASPDMAILNLSVLRQA KTAREAMTANNEAMTKVLDAMKKAGIEDRDLQTGGIDI QPIYVYPDDKNNLKEPTITGYSVSTSLTVRVRELANVGK ILDESVTLGVNQGGDLNLVNDNPSAVINEARKRAVANAI AKAKTLADAAGVGLGRVVEISELSRPPMPMPIARGQFR TMLAAAPDNSVPIAAGENSYNVSVNVVFEIK | 1 |
| BP26 having His tag and TEV cleavage site inserted thereto (sequence used for cloning) | MGSSHHHHHHSSGLVPRGSHMASMTGGQQMGRGSE NLYFQGSQENQMTTQPARIAVTGEGMMTASPDMAILN LSVLRQAKTAREAMTANNEAMTKVLDAMKKAGIEDRD LQTGGIDIQPIYVYPDDKNNLKEPTITGYSVSTSLTVRV RELANVGKILDESVTLGVNQGGDLNLVNDNPSAVINEA RKRAVANAIAKAKTLADAAGVGLGRVVEISELSRPPMP MPIARGQFRTMLAAAPDNSVPIAAGENSYNVSVNVVFE IK | 2 |

Figure 17:
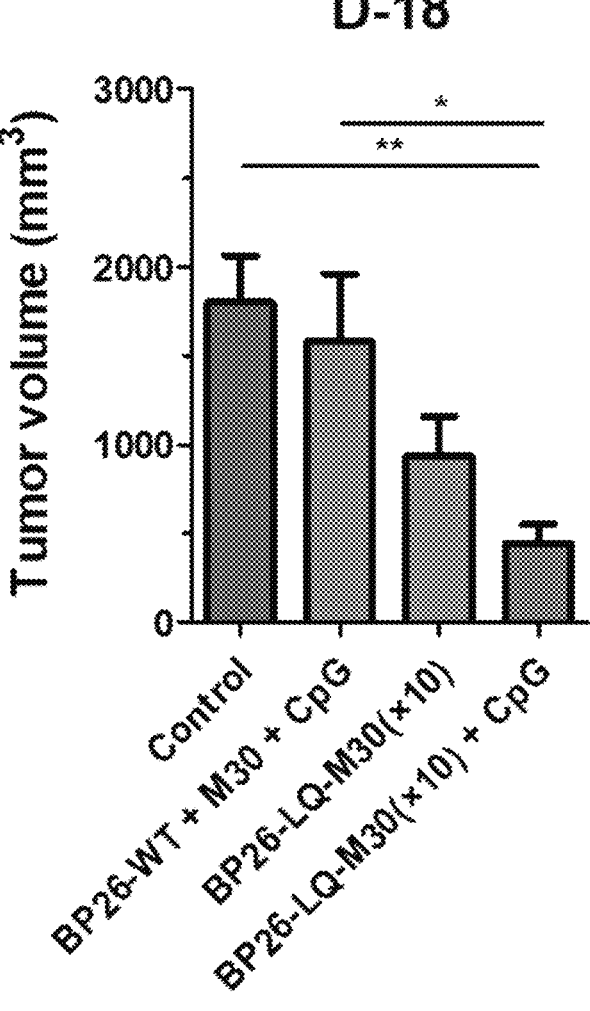

FIG. 17 shows the B16F10 tumor volume on the 18th day after tumor inoculation.

Figure 18:
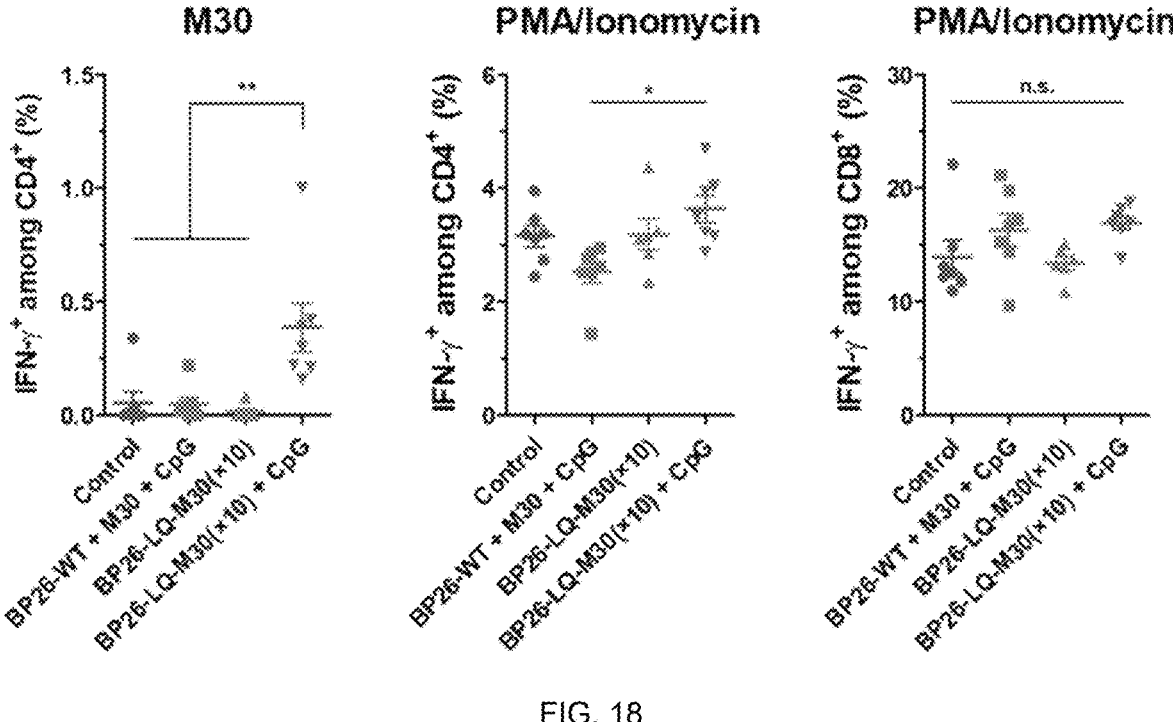

FIG. 18 shows the antigen-specific T cell immune response by inoculation with the BP26-LQ-M30 (×10) fusion protein.

Figure 19:
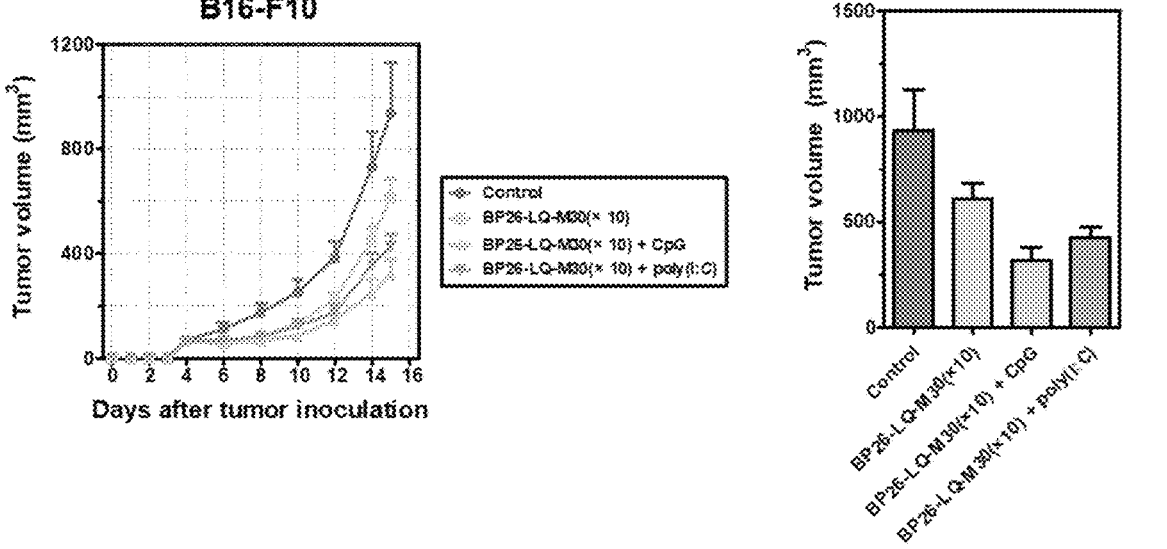

FIG. 19 shows that the adjuvant (e.g. CpG, poly(I:C)) improves the antitumor efficacy of the BP26-LQ-M30 (×10) fusion protein.

Figure 20:
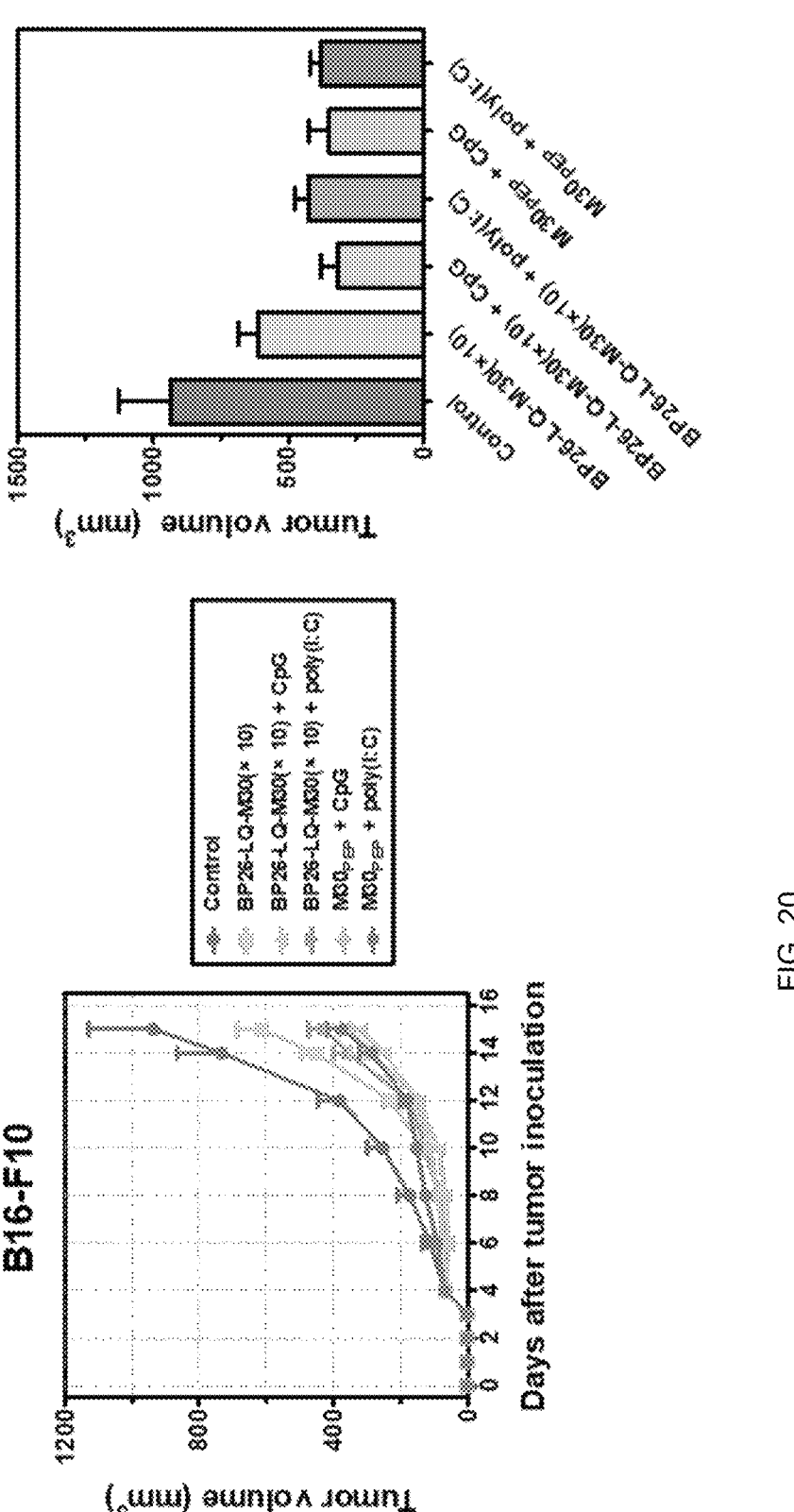

FIG. 20 shows the efficacy of administration of the BP26-LQ-M30 (×10) fusion protein compared to the positive control group.

Figure 21:
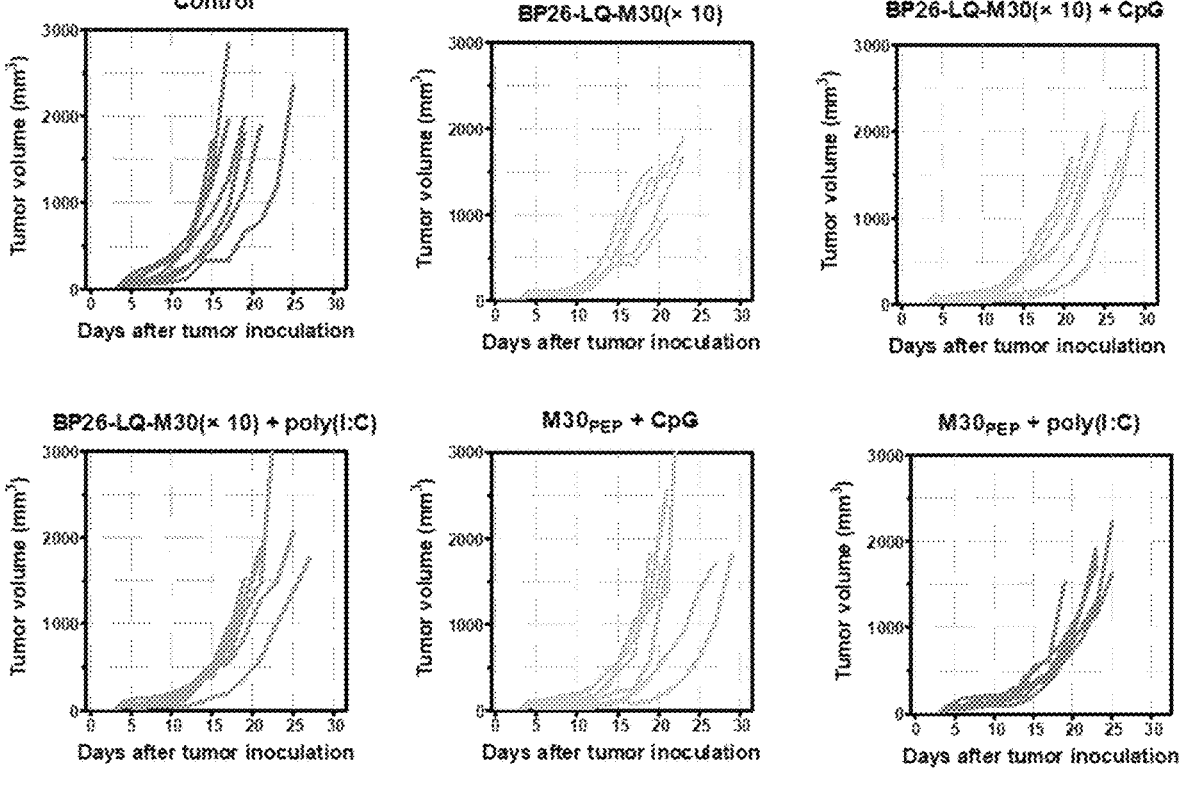

FIG. 21 shows the B16F10 individual tumor growth curve of each group shown in FIG. 20.

DETAILED DESCRIPTION

Hereinafter, the present disclosure will be described in more detail through examples. These examples are only for illustrating the present disclosure in more detail, and it will be apparent to those skilled in the art that the scope of the present disclosure is not limited by these examples according to the gist of the present disclosure.

EXAMPLES

Unless otherwise stated, "%" used to indicate the concentration of a specific substance is (weight/weight) % for Tandem repeats of the M2e (×4) sequence were synthesized using a gene synthesizer (Bioneer, Korea) and incorporated into the pUC vector. The four M2e repeats (SLLTE-VETPIRNEWGSRSNDSSD, SEQ ID NO: 3) in the sequence were separated by an amino acid linker consisting of GGGSG, SEQ ID NO: 19. The nucleotide sequence of M2e (×4) is as follows, and was codon-optimized to maximize expression in an *E. coli* system. BamHI and Xho I restriction sites were incorporated to the N- and C-termini, respectively.

```
Nucleic acid sequence of M2e (SEQ ID NO: 7):
AGCCTGCTGACCGAAGTCGAGACTCCGATCCGTAATGAATGGGGCT

CTCGTTCTAACGACTCGTCGGAT
```

The expression vector for BP26-M2e (×4) was constructed by subcloning into a modified pET28a vector containing an N-terminal His-tag and a tobacco etch virus (TEV)protease cleavage site after the His tag, and the expression vector for BP26-M2e (×8) was constructed using an in-fusion cloning kit (Takara, Japan) according to the manufacturer's protocols. Recombinant proteins were expressed in BL21 (DE3) RIPL *E. coli* for 16 hours at 18° C. after induction with 1 mM isopropyl β-D-1-thiogalacto-pyranoside (IPTG) and were purified by Ni-NTA affinity chromatography (Qiagen, Hilden, Germany). After cleavage of the N-terminal His-tag with TEV protease, proteins were further purified using Ni-NTA resin, a HiTrap Q-SP cation exchange column, and Superdex 200 26/60 size-exclusion chromatography (GE Healthcare, Illinois, USA).

Expression and purification of recombinant proteins were confirmed by SDS-PAGE.

Figure 1:
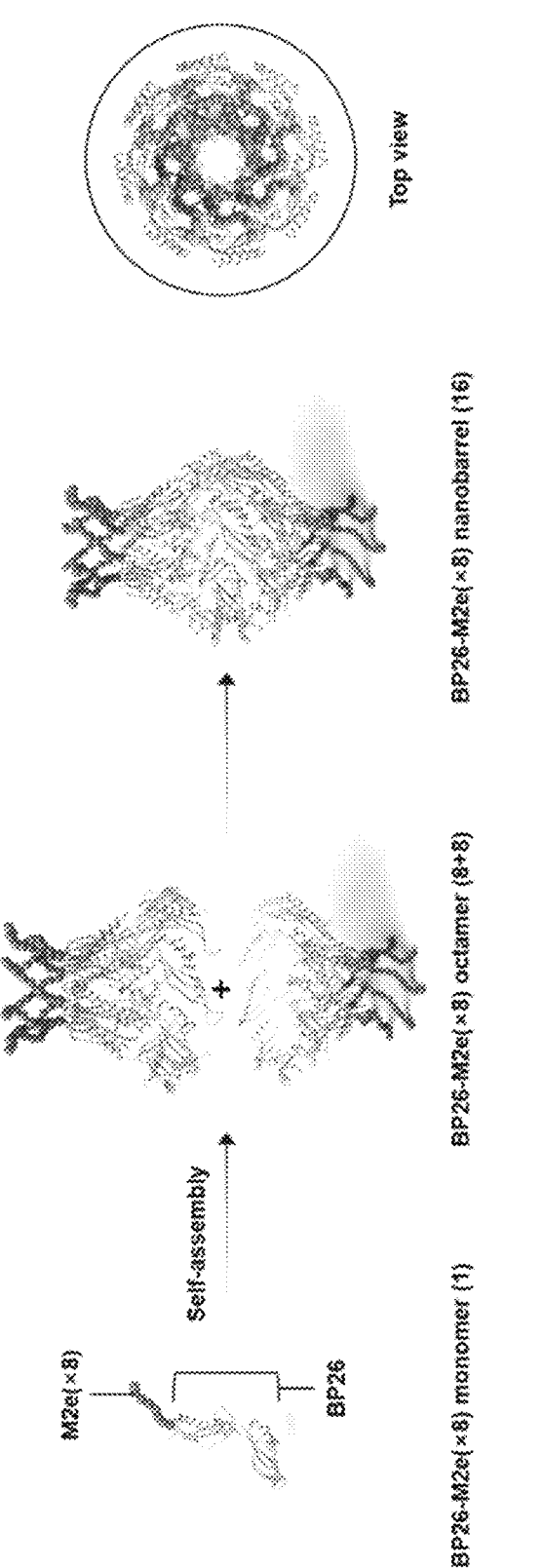
FIG. 1 shows a BP26-based nanoarchitecture displaying an influenza M2e epitope.

The main epitope of M2e was fused to monomeric BP26, which undergoes self-assembly into an octamer and then further assembles into a hexadecameric hollow barrel-like architecture, termed a nanobarrel, in which M2e antigens are displayed around the rim of the nanobarrel (FIG. 1).

Figure 2A:
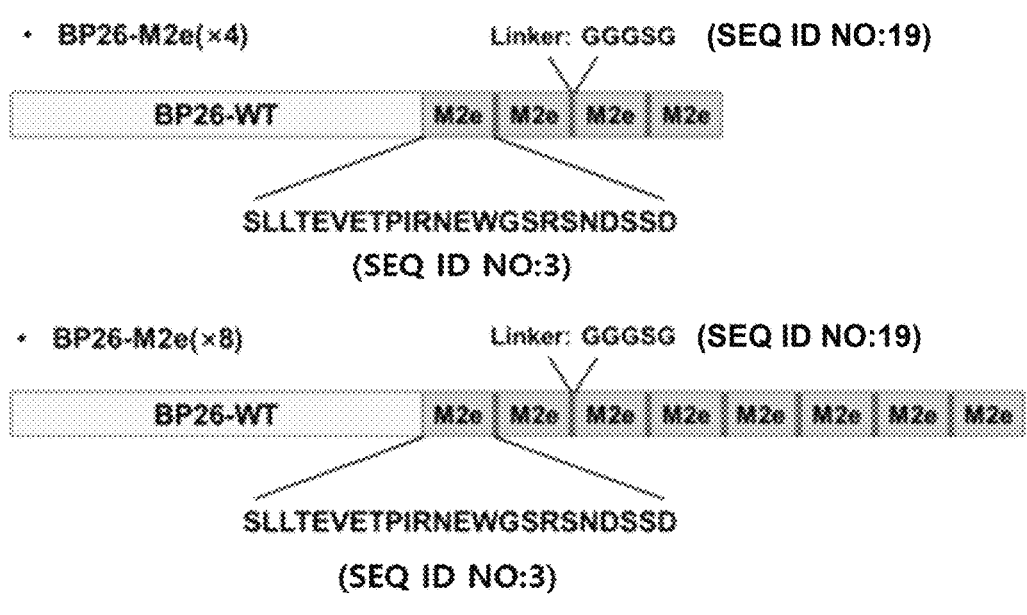
FIG. 2A shows a fusion protein including BP26 and M2e.
Figure 2B:
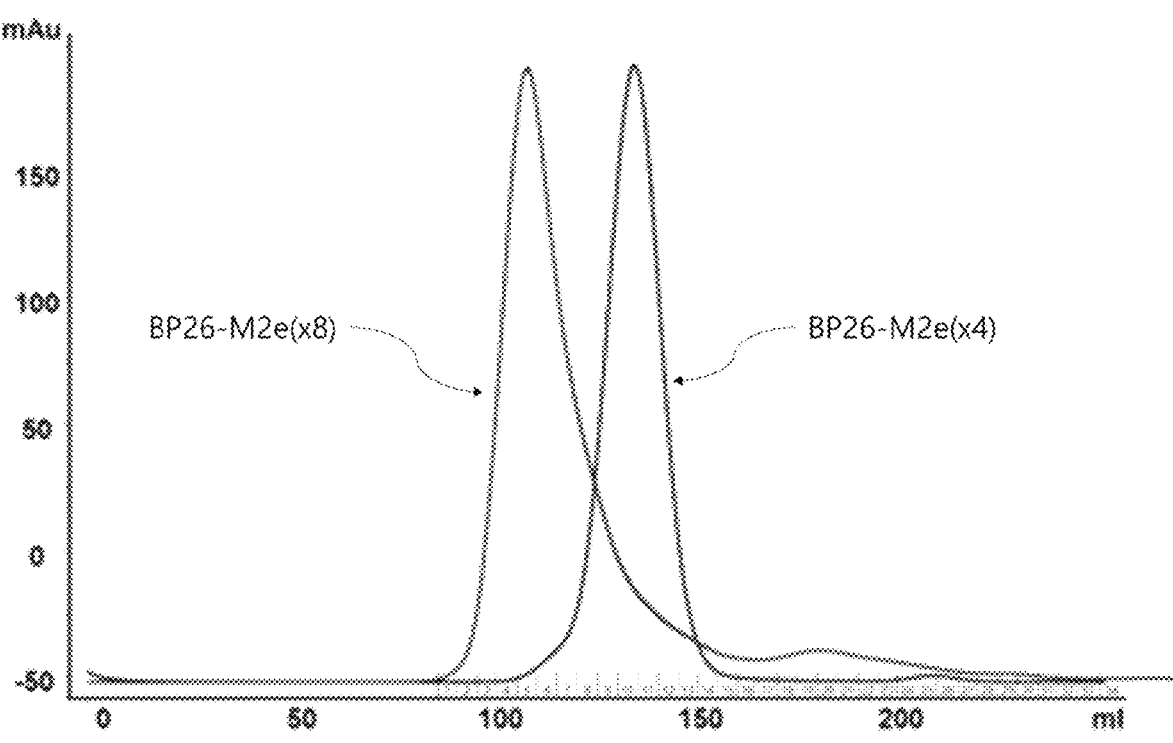
FIG. 2B shows the expression of BP26-M2e (×4) and BP26-M2e (×8) as analyzed by size exclusion chromatography.
Figure 2C:
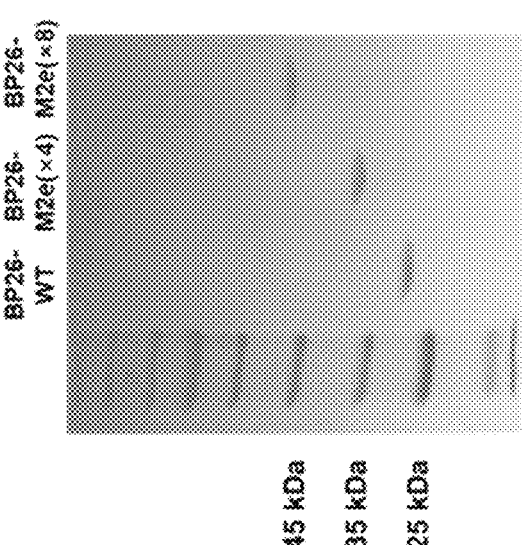
FIG. 2C shows the expression of BP26-WT, BP26-M2e (×4) and BP26-M2e (×8) as analyzed by SDS-PAGE.

Four and eight tandem repeats of M2e were genetically fused to the C-terminus of monomeric BP26 using a short flexible linker (GGGSG, SEQ ID NO: 19) to yield two fusion proteins, designated BP26-M2e (×4) and BP26-M2e (×8), respectively (FIG. 2A). Both fusion proteins were expressed in *E. coli* in high yield and subsequently purified by size-exclusion chromatography (FIG. 2B). SDS-PAGE analysis clearly distinguished the two proteins based on their molecular size (FIG. 2C).

Example 2: Characterization of BP26-M2e Nanoarchitecture 2-1. Morphology of BP26-M2e (×4) and BP26-M2e (×8) Evaluated by Transmission Electron Microscopy The morphology of BP26-M2e (×4) and BP26-M2e (×8) was evaluated by negative staining transmission electron microscopy (TEM).

Figure 2D:
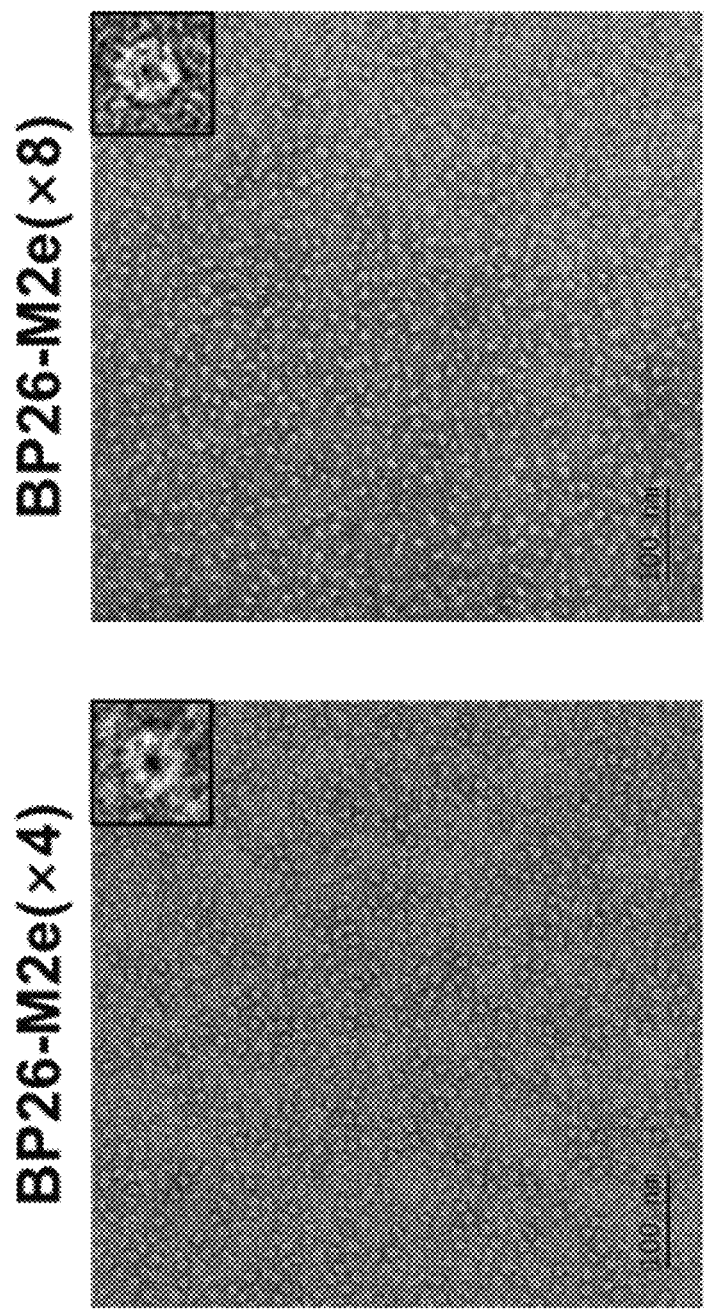
FIG. 2D shows transmission electron microscopy (TEM) images of BP26-M2e (×4) and BP26-M2e (×8) (scale bar=100 nm).

The transmission electron microscopy (TEM) analysis of the self-assembled structures of these fusion proteins revealed that both BP26-M2e (×4) and BP26-M2e (×8) formed discrete nanoparticles with mean diameters of 16.4 nm and 19.2 nm, respectively, and contained a hollow cavity (hole) at its center (FIG. 2D); the hole in the latter was smaller than that in the former, presumably because the larger M2e tandem repeats in the latter protruded around the hole. These structural observations indicate that the presence of M2e antigen does not interfere with the BP26 self-assembly process, despite the fact that the size of the M2e (×8) repeat (~23 kDa) is similar to that of a BP26 monomer (~28 kDa), suggesting that there might be no need for complicated vaccine module design and expression screening.

2-2. Hydrodynamic Size of Nanoarchitectures

The hydrodynamic size of nanobarrels was determined by dynamic light scattering (DLS) at ambient temperature using a Zetasizer Nano range system (Malvern, Worcestershire, UK).

Hydrodynamic size is defined as "the size of an imaginary solid sphere that diffuses in the same way as the particle being measured" as measured by DLS.

Figure 2E:
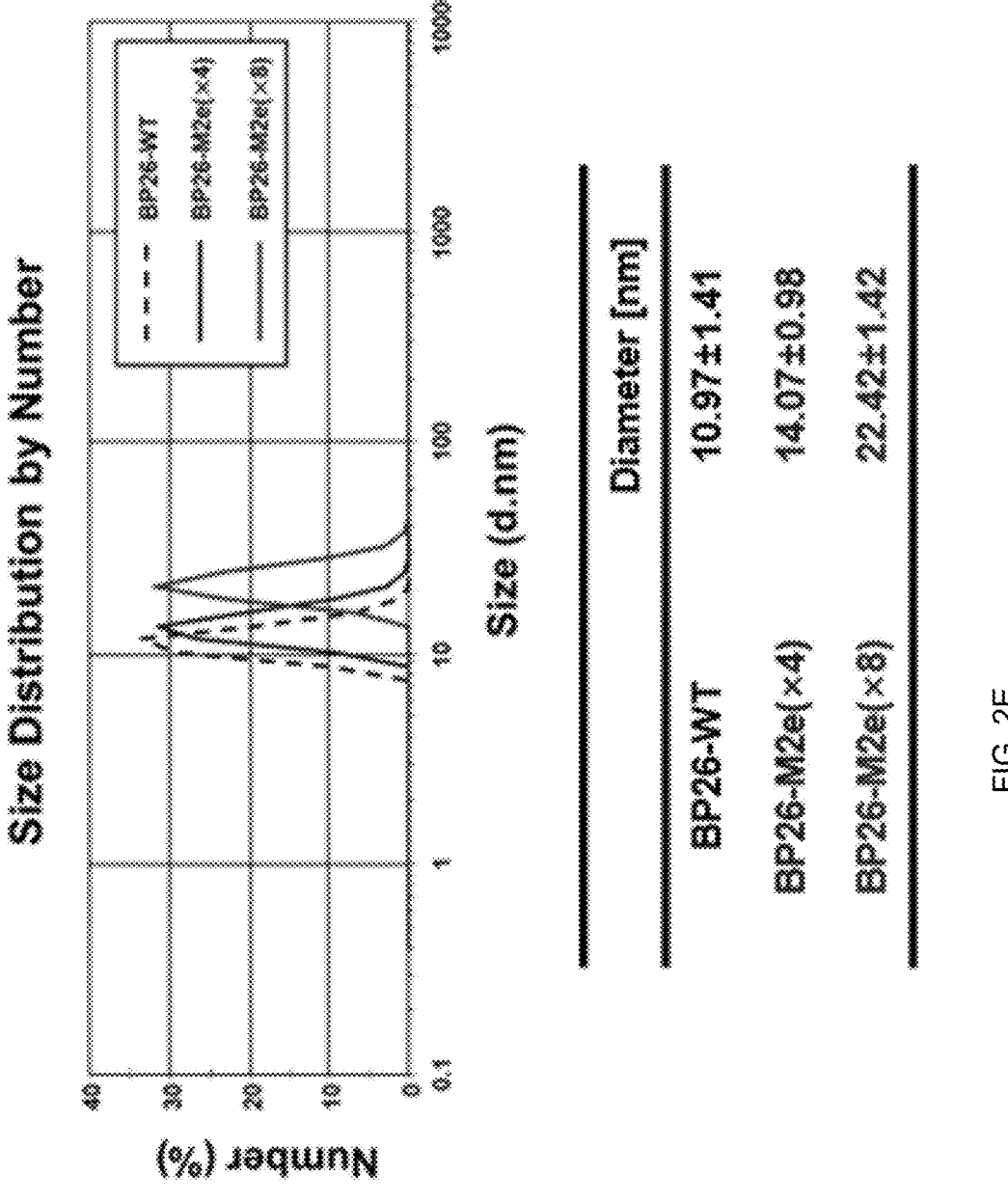
FIG. 2E shows the hydrodynamic diameter of the nanoarchitecture as measured by dynamic light scattering (DLS).

The hydrodynamic size of BP26-based nanobarrels, measured by dynamic light scattering (DLS), was ~10.97 nm for wild-type (WT) BP26 and increased to ~14.07 nm for BP26-M2e (×4) and ~22.42 nm for BP26-M2e (×8) (FIG. 2E).

2-3. Accessibility of Anti-M2e Antibody to M2e Epitope on BP26 Nanoarchitecture Surface The accessibility of the anti-M2e antibody to M2e epitopes on the surface of BP26 nanobarrel was confirmed using ELISA. BP26-WT, BP26-M2e (×4), and BP26-M2e (×8) were coated onto 96-well plates at different concentrations (M2e concentration, 0.01-1000 μmol) and incubated overnight at 4° C. The plates were then blocked with PBS with Tween-20 (PBST) containing 2% bovine serum albumin (BSA) for 1 hour at room temperature and then incubated with mouse anti-M2e IgG antibody (14C2 clone, 1:1000 dilution; Santa Cruz Biotechnology, Texas, USA) for 2 hours at room temperature. Plates were subsequently washed and incubated with horseradish peroxidase (HRP)-conjugated goat anti-mouse IgG secondary antibody (1:5000 dilution; Santa Cruz Biotechnology) for 1 hour at room temperature, after which TMB substrate solution was added to each well and changes were detected colorimetrically by measuring absorbance at 450 nm using a microplate reader (VersaMax™; Molecular Devices, California, USA).

Figure 2F:
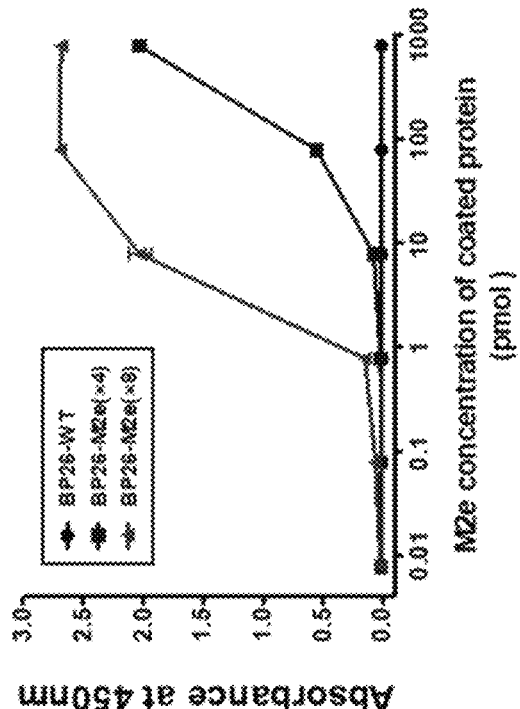
FIG. 2F shows the results of ELISA analysis to confirm the accessibility and reactivity of the anti-M2e antibody to the multi-tandem (tandem) repeat structure of the M2e epitope displayed on the surface of the BP26 nanoarchitecture.
Figure 2F:
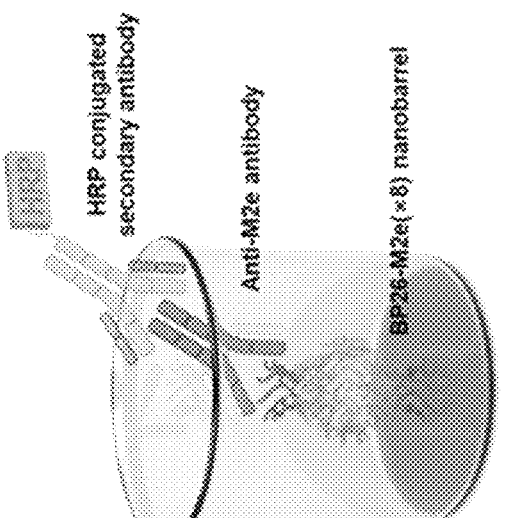

The ELISA results revealed much higher reactivity of the anti-M2e antibody against BP26-M2e (×8) than BP26-M2e (×4) (FIG. 2F), implying that increasing M2e tandem repeats may result in more efficient recognition of displayed antigen by BCR on B cells, leading to greater B cell responses.

Example 3: Confirmation of Antibody Production in Mice by Nanoarchitectures 3-1. Immunization of Mice Using Nanoarchitectures Six-week-old female BALB/c mice were immunized using a homologous prime-boost regimen. Mice were divided into five groups: PBS buffer vehicle, (BP26-WT+ M2e)/Alum (BP26-WT, 20 μg; M2e, 7.3 μg), BP26-M2e (×4) (25 μg), BP26-M2e (×8) (18 μg), and BP26-M2e (×8)/Alum (BP26-M2e: 18 μg). Mice in each group were immunized thrice at intervals of three weeks by subcutaneous injection into both footpads.

The doses were adjusted so that immunizing M2e was administered in equimolar amounts. For the groups containing alum, the antigen solution and 30% AlOH solution were mixed in equal amounts. A 30% AlOH solution was prepared by diluting an Al2O3 solution (Rehydragel HPA, Reheis, Berkeley Heights, NJ) with dH2O to adjust the pH to 7.

3-2. Determination of M2e Antibody Production by ELISA

Mice were divided into 5 treatment groups as described above and immunized three times at 3-week intervals. To determine the humoral immune response, sera were isolated from blood collected retro-orbitally into Serum Separator Tubes (BD) at four time points: day-1 (pre-immunization) and days 14, 35, and 56 (i.e., 2 weeks after each immunization). M2e-specific antibody titers were determined by ELISA.

96-well plates were coated with M2e antigen and incubated overnight at 4° C. Plates were washed and blocked with PBST containing 2% BSA for 1 hour at room temperature, and then incubated with diluted serum samples for 2 hours at room temperature. Plates were subsequently washed and incubated with HRP-conjugated goat anti-mouse IgG, IgG1 or IgG2a (1:5000 dilution; Santa Cruz Biotechnology) as secondary antibodies for 1 hour at room temperature.

Figure 3A:
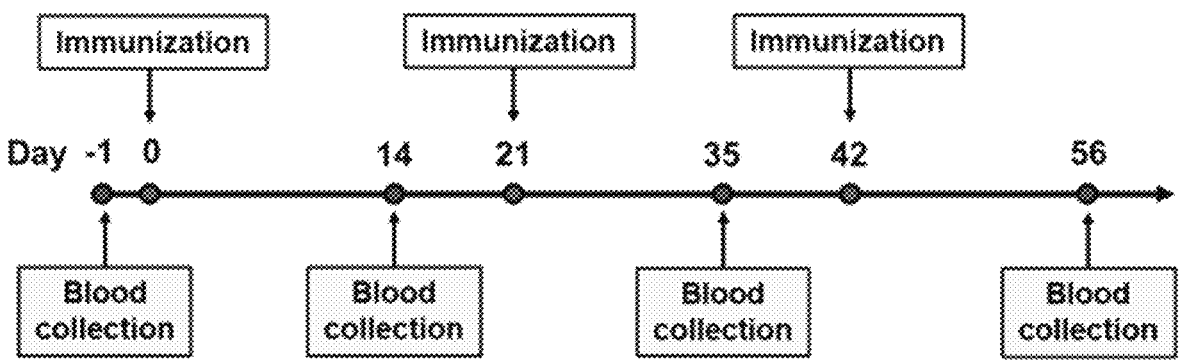
FIG. 3A shows an experimental method for confirming the antibody production in mice by the nanoarchitecture.

The immunogenicity of the BP26-M2e nanoarchitectures was evaluated in Balb/c mice immunized thrice at 3-week intervals via subcutaneous injection. Titers of anti-M2e antibody were measured in sera collected on days 14, 35 and 56 (FIG. 3A).

A physical mixture of soluble M2e and BP26-WT did not induce any detectable antibody production regardless of the number of immunization, even with the use of an alum adjuvant.

Figure 3B:
FIG. 3B shows titers of anti-M2e antibodies present in the sera after immunization with nanoarchitectures as measured by ELISA.
Figure 3B:
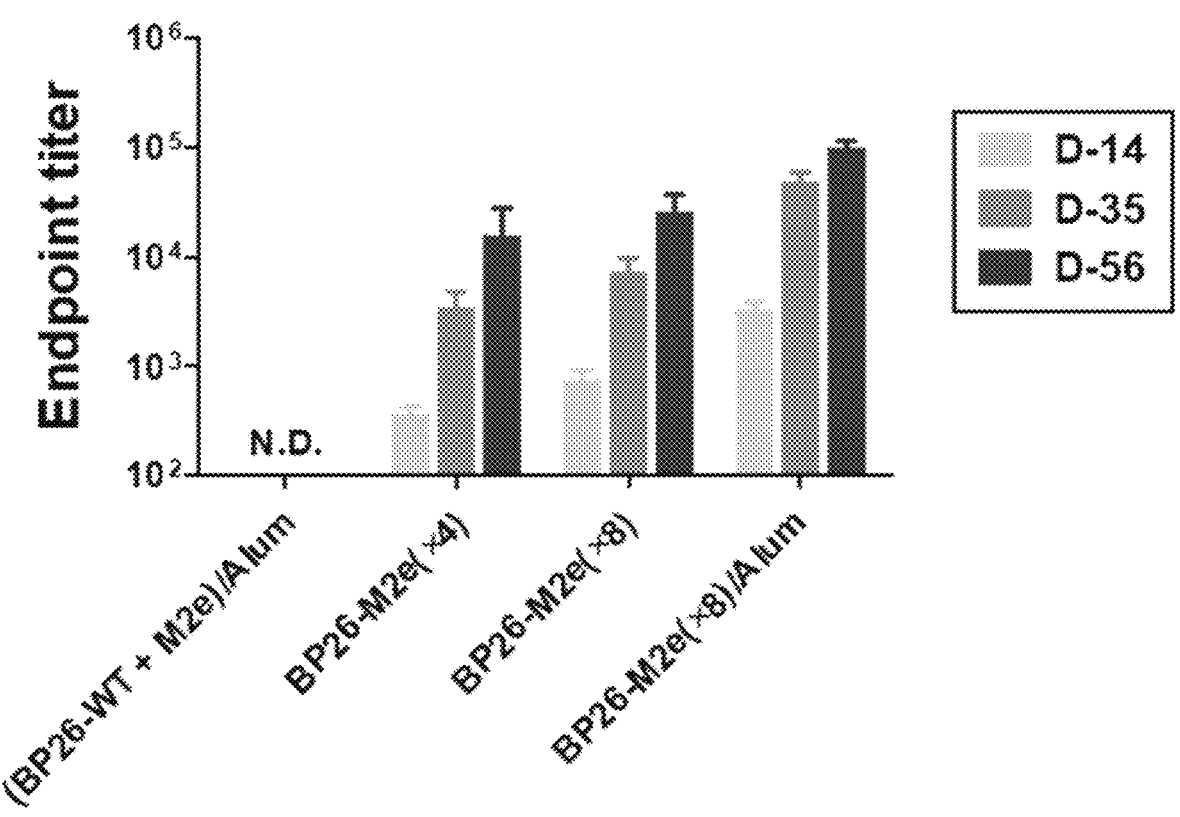
Figure 3C:
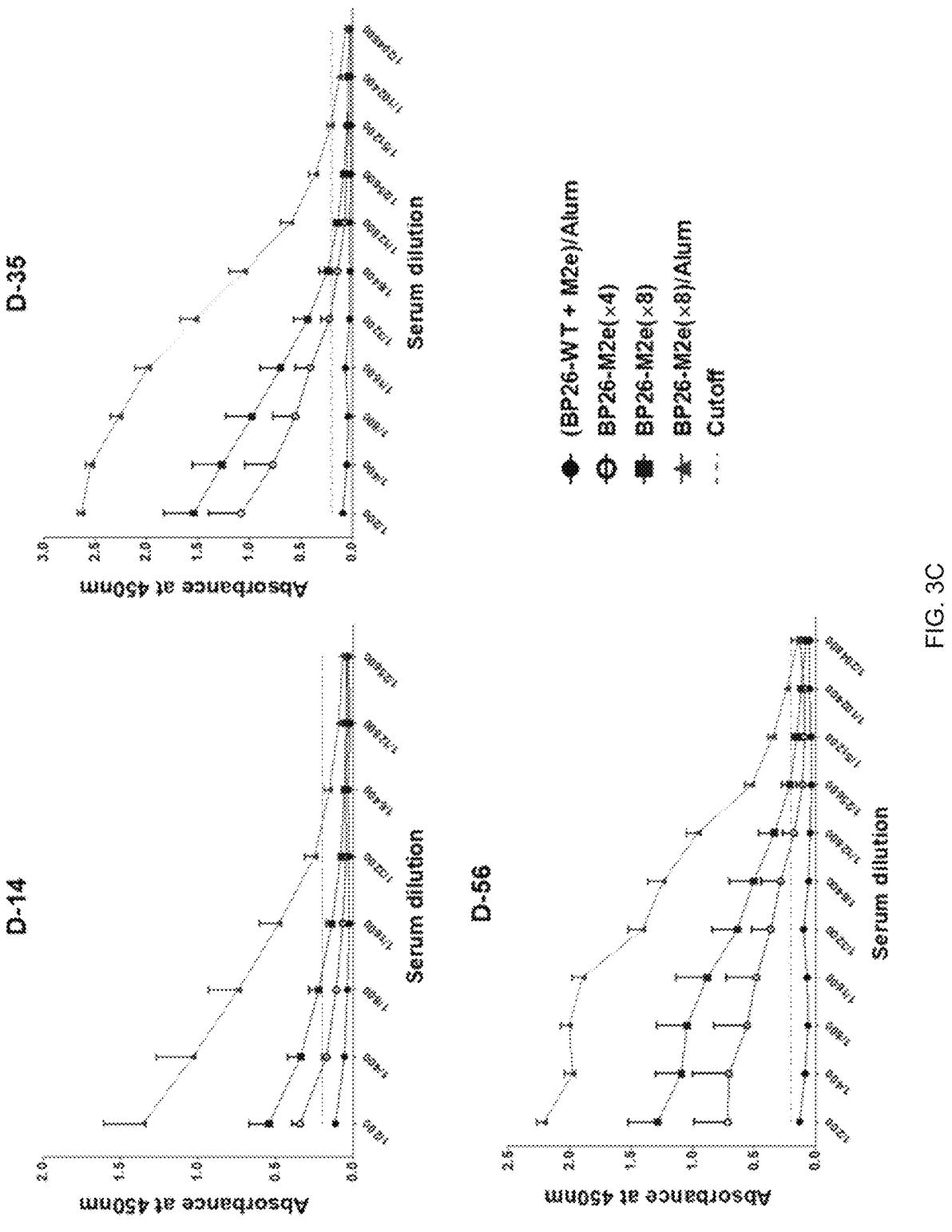
FIG. 3C shows titers of anti-M2e IgG in sera of immunized mice (days 14, 35, and 56) as measured by ELISA.

In contrast, immunization with BP26-M2e nanoarchitectures induced the production of anti-M2e IgG antibodies; notably, antibody titers increased more than 100-fold after multiple boosting immunizations. In addition, the BP26-M2e (×8)-immunized group had higher anti-M2e IgG titers than the BP26-M2e (×4)-immunized group. While nanoarchitecture-based immunization per se induced a high level of antibody production, efficiency was further enhanced by additional use of alum adjuvant (FIGS. 3B and 3C).

Figure 3D:
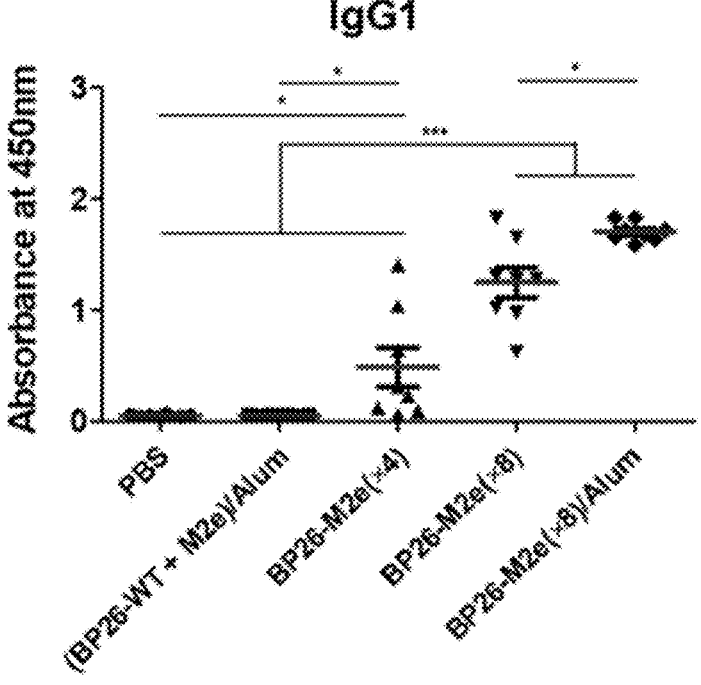
FIG. 3D shows titers of M2e-specific IgG1 and IgG2a in sera of immunized mice (day 56) as measured by ELISA.
Figure 3D:
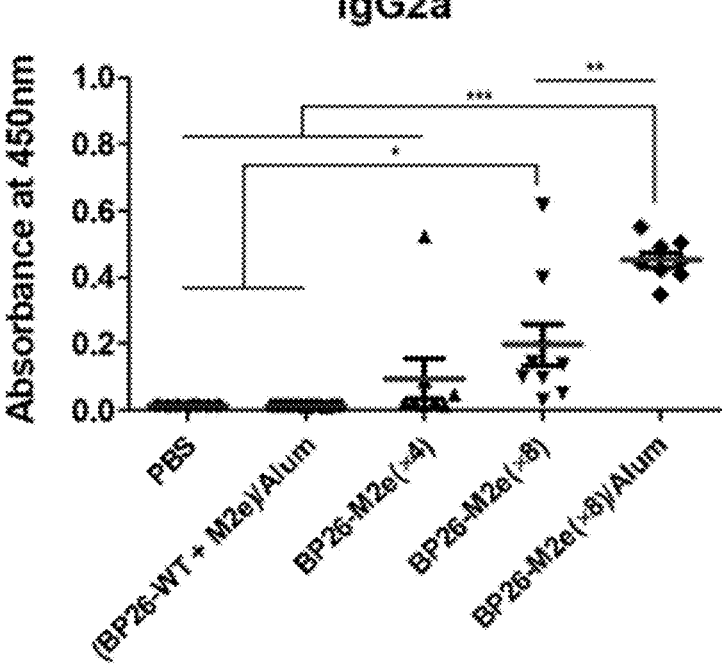

In addition, an analysis of M2e-specific antibody responses according to IgG1 and IgG2a isotypes showed that BP26-M2e (×8) induced significantly greater IgG1 and IgG2a responses than did BP26-M2e (×4) (FIG. 3D).

3-3. Determination of BP26 Antibody Production by ELISA

To evaluate the immunogenicity of the BP26 carrier, 96-well plates were coated with BP26 protein and incubated overnight at 4° C. Plates were washed, blocked, and incubated with serum samples as described supra. Plates were then washed and incubated with HRP-conjugated goat anti-mouse IgG (1:5000 dilution) as secondary antibody for 1 hour at room temperature.

Figure 3E:
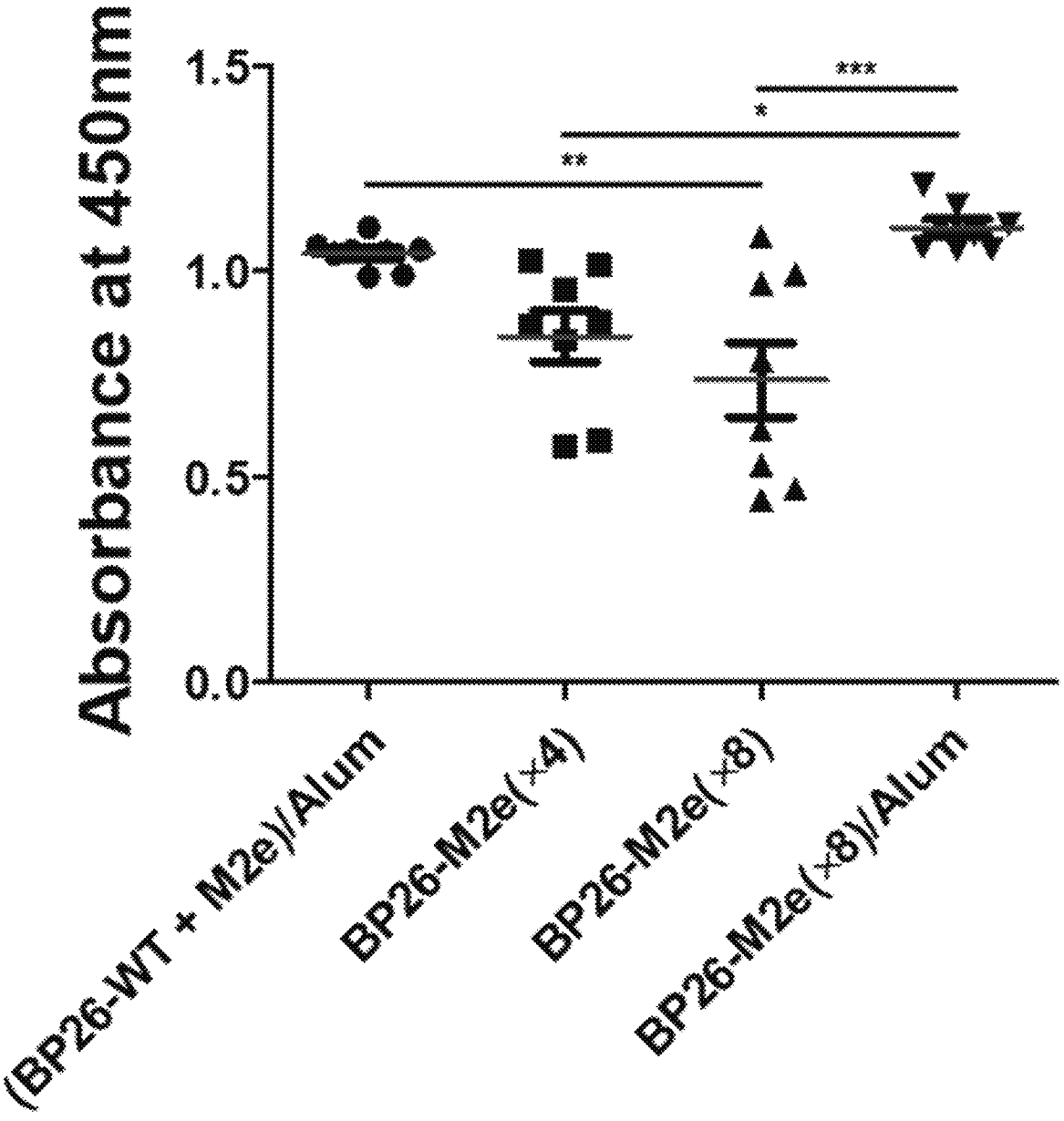
FIG. 3E shows titers of anti-BP26 IgG in sera of immunized mice (day 56) as measured by ELISA.

Since BP26 is the major immunodominant antigen of *Brucella*, antibodies specific for the BP26 carrier were generated in the immune group (FIG. 3E); However, this anti-BP26 antibody did neither interfere with the M2e-specific antibody response, nor induced complications such as autoimmune responses in immunized animals.

These results clearly indicate that genetic fusion of M2e antigen to BP26 and its self-assembled nanoarchitecture is critical for inducing robust antibody production (humoral responses) against the low-immunogenic M2e of influenza virus and rather, is most likely to protect against the zoonotic *Brucella* infection.

To verify this hypothesis we examined whether pre-existing anti-BP26 antibodies could compromise the humoral responses induced by BP26-M2e (×8) nanobarrel immunization. One group of mice was immunized with BP26-WT/Alum three weeks in advance to generate anti-BP26 antibodies, followed by BP26-M2e (×8) immunization, and the other group of mice was immunized with BP26-M2e (×8) only.

Figure 3F:
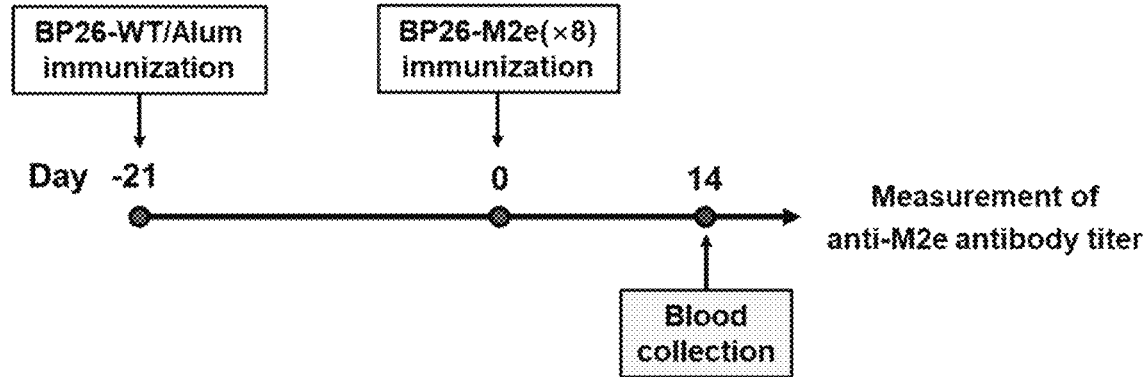
FIG. 3F shows Effect of pre-existing anti-BP26 antibodies on M2e-specific humoral responses elicited by BP26-M2e nanovaccine. (A) Immunization schedule. (B) Anti-M2e IgG titer in the sera of BP26-M2e (×8) immunized or non-immunized control mice. Titers of M2e-specific antibody were measured by ELISA. (*P<0.05, P<0.01, *P<0.001, n.s.=not significant, one-way ANOVA with post hoc Tukey's test).
Figure 3F:
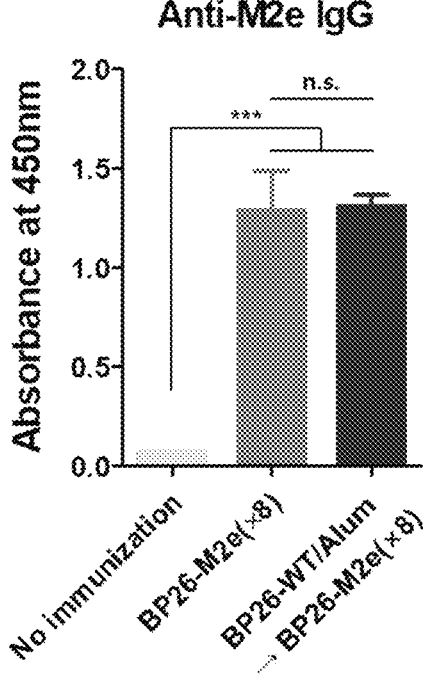

Two weeks after BP26-M2e (×8) immunization, the titer of anti-M2e antibodies in the sera of each group was measured by ELISA (FIG. 3F, A).

analysis using confocal microscopy was performed. To evaluate the binding capacity of anti-M2e antibodies, MDCK cells were seeded and grown on coverslips IN 24-well plates, grown at a density of 2×105 cells per well in 0.5 mL medium and allowed to adhere overnight. MDCK cells were then infected with influenza A virus strains (A/PR/8, A/CA/04/09 or A/Aquatic bird/Korea) in influenza infection medium (DMEM medium supplemented with MEM-vitamin, gentamicin and 4% BSA) and cultured for 20 hours. Cells were washed with PBS and fixed with 10% formalin solution for 10 min. Thereafter, cells were incubated for 2 hours at room temperature with sera containing anti-M2e IgG antibody (1:100 dilution) obtained from immunized mice. Cells were washed with PBS and fixed with 10% formalin solution for 10 min. Cells were incubated with sera containing immunized mice anti-M2e IgG antibody (1:100 dilution) at room temperature for 2 hours. The serum containing the M2e IgG antibody was obtained on day 56 from M2e (×8) immunized mice. Incubation was made with anti-M2e IgG antibody for 2 hours and then with Alexa Fluor 594-conjugated donkey anti-mouse secondary antibody (1:200 dilution; Abcam) for 1 hour at room temperature. Nuclei were stained with Hoechst 33342 (1:5000 dilution). All samples were imaged using a confocal laser scanning microscope (LSM 780; Carl Zeiss).

Because M2e, unlike the large glycoproteins hemagglutinin (HA) and neuraminidase (NA), is a small, low-abundance protein buried in the membrane of virions, the anti-M2e antibody is known to exert its antiviral effect by inducing antibody-dependent cellular cytotoxicity (ADCC) upon binding to infected cell membranes, rather than by directly neutralizing the viral infection. That is, protection from viral infection is expected to be directly related to the ability of anti-M2e antibody to bind the plasma membrane of virus-infected cells.

The virus strain and M2e amino acid sequence used in the experiment are as follows (Table 2).

TABLE 2

| Virus strain | Subtype | M2e amino acid sequence | SEQ ID NO: |
|---|---|---|---|
| A/PR/8 | H1N1 | SLLTEVETPIRNEWGCRCNDGSD | 4 |
| A/CA/04/09 | H1N1 | SLLTEVETPTRNGWECKCSDSSD | 5 |
| A/Aquatic bird/Korea | H5N2 | SLLTEVETPTRSEWECRCSDSSD | 6 |

Although a considerable level of antibodies against the immunogenic BP26 carrier was generated by BP26-WT/Alum immunization, there was little difference in the titers of anti-M2e antibodies between the two groups (FIG. 3F, B), indicating that pre-existing anti-BP26 antibody is unlikely to interfere with the M2e-specific antibody response.

Figure 4A:
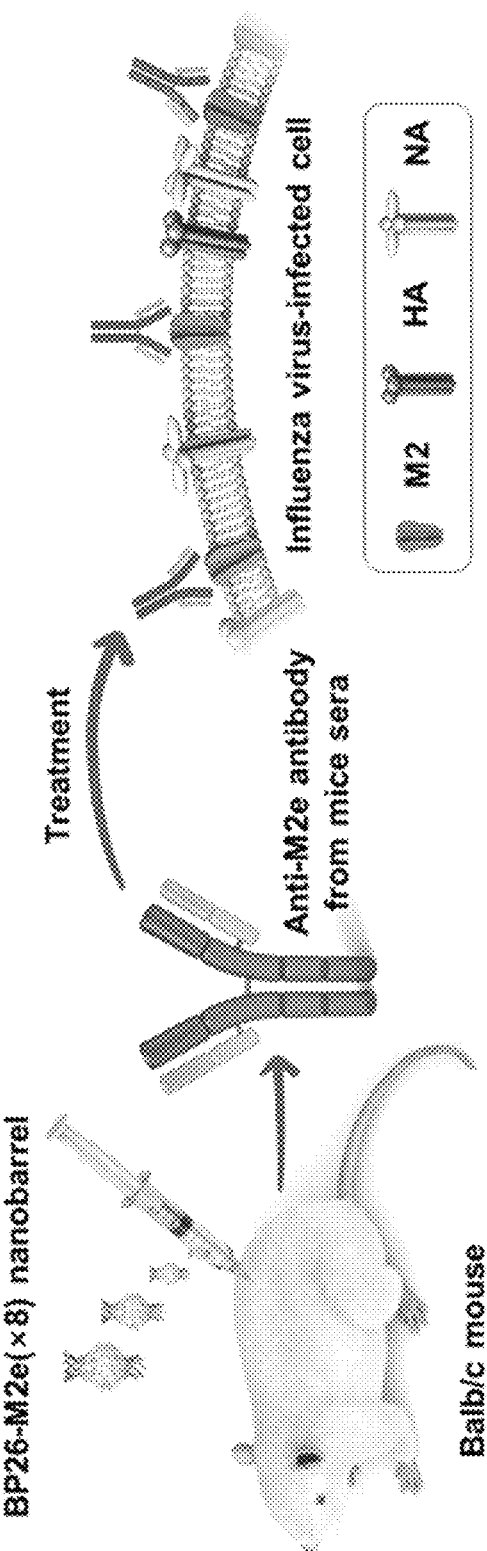
FIG. 4A shows anti-M2e antibody binding to M2e displayed on influenza virus-infected cells.

Example 4: Binding Capacity of Anti-M2e Antibody to Influenza Virus-Infected Cells Immunocytochemistry (ICC), ELISA, and Western blot were performed to determine whether the anti-M2e antibody of the immunized mouse serum could recognize influenza-infected cells expressing M2e on the plasma membrane (FIG. 4a).

Figure 4B:
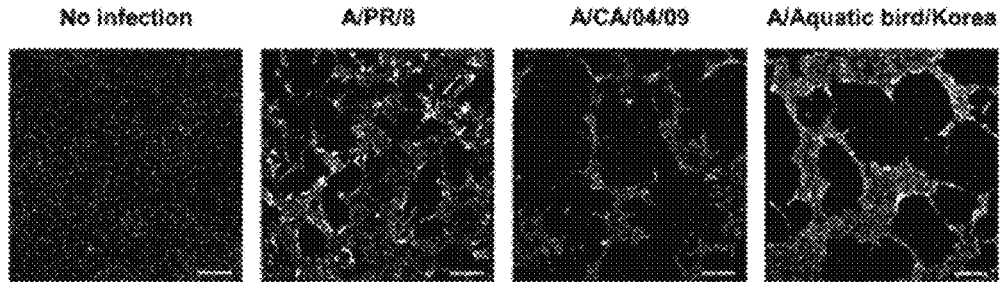
FIG. 4B shows confocal laser-scanning microscopic images accounting for the binding capability of anti-M2e antibody for influenza virus-infected MDCK cells (scale bar=100 μm).

4-1. Confirmation of Anti-M2e Antibody Binding to Influenza Virus-Infected Cells Through Immunocytochemistry In order to confirm the binding of the anti-M2e antibody to the influenza virus-infected cells, immunocytochemical Confocal laser-scanning microscopic imaging revealed that the anti-M2e antibody in immunized mouse sera exhibited marked binding to influenza virus-infected MDCK cells, regardless of virus subtype, whereas little binding was observed for non-infected MDCK cells (FIG. 4B).

4-2. Confirmation of Anti-M2e Antibody Binding to Influenza Virus-Infected Cells Through Whole-Cell ELISA Specific binding of the anti-M2e antibody was confirmed by whole-cell ELISA (FIG. 4c).

For whole-cell ELISA, MDCK cells were seeded at a density of 1×104 cells per well into 96-well plates containing 0.2 mL medium each well and allowed to adhere overnight. MDCK cells were infected with influenza virus strains (multiplicity of infection=0.1) and incubated with sera containing anti-M2e IgG antibody (1:100 dilution) from mice immunized. The sera containing the anti-M2e IgG antibody was obtained from M2e (×8) immunized mice on day 56. Cells were then incubated with HRP-conjugated goat anti-mouse IgG secondary antibody (1:5000 dilution)

for 1 hour at room temperature, and absorbance was read at 450 nm using a microplate reader.

Figure 4C:
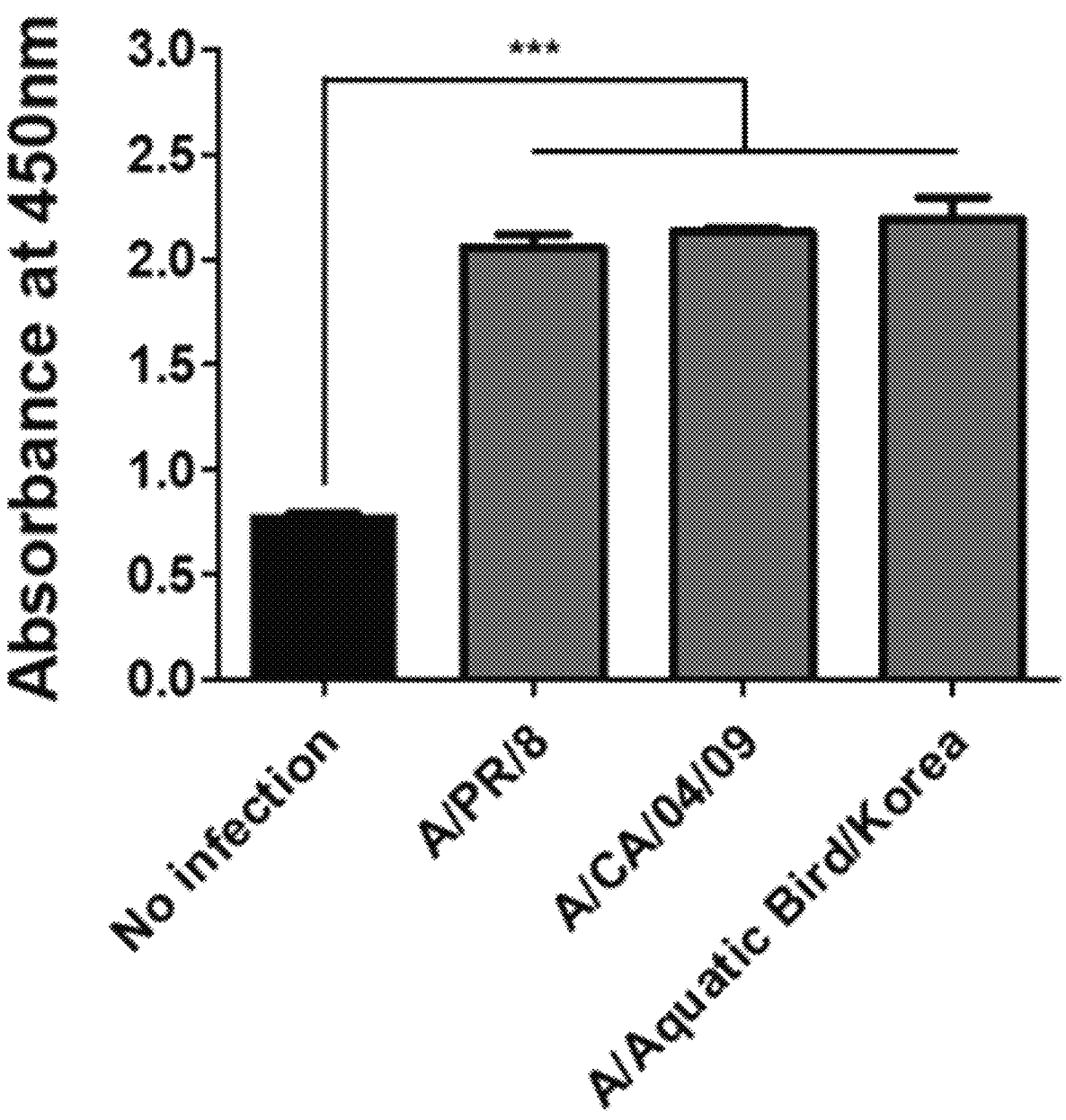
FIG. 4C shows the binding capability of anti-M2e antibody to influenza virus-infected MDCK cells as measured by whole-cell ELISA.

The ELISA data revealed that the anti-M2e antibody in immunized mouse sera exhibited binding to influenza virus-infected MDCK cells, regardless of virus subtype, whereas little binding was observed for non-infected MDCK cells (FIG. 4C).

4-3. Confirmation of Anti-M2e Antibody Binding to Influenza Virus-Infected Cells Through Western Blotting Specific binding of the anti-M2e antibody was confirmed by western blotting.

For Western blot analysis, MDCK cells were seeded at a density of 5×105 cells per well into 6-well plates containing 2 mL medium each well, incubated overnight, then infected with influenza virus strains (multiplicity of infection=1). Virus-infected cells were harvested and lysed using protein extraction solution (PRO-PREP™, iNtRON Biotechnology) according to the manufacturer's instructions, after which the protein concentration was determined by Bradford assay. Proteins in whole-cell extracts were separated by SDS-PAGE on 20% gels and then transferred to a polyvinylidene difluoride (PVDF) membrane. The membrane was blocked by incubating with 5% skim milk in TBS-T for 2 hours at room temperature and then incubated for 2 hours at room temperature with sera containing anti-M2e IgG antibody (1:200 dilution), obtained from immunized mice. The membrane was incubated with HRP-conjugated goat anti-mouse IgG secondary antibody (1:5000 dilution) for 1 hour at room temperature, after which immunoreactive proteins were imaged using a ChemiDoc XRS Imaging System (BIO-RAD, Hercules, CA).

Figure 4D:
FIG. 4D shows the binding capability of anti-M2e antibody to influenza virus-infected MDCK cells as measured by Western blot analysis.

It was revealed from the data of western blot analysis that the anti-M2e antibody in immunized mouse sera exhibited binding to influenza virus-infected MDCK cells, regardless of virus subtype, whereas little binding was observed for non-infected MDCK cells (FIG. 4D).

Collectively, these findings indicate that immunization of mice with BP26-M2e nanovaccine generates an anti-M2e antibody that can specifically bind to mammalian cells infected with various influenza viruses, thereby suggesting the possibility that BP26-M2e nanoarchitectures could be developed as a universal vaccine against influenza.

Example 5: Evaluation of Vaccine Effect Through Virus Inoculation Experiment For the virus inoculation experiment, mice were immunized in the same manner as in Example 3-1 as follows:

Mice were divided into five groups: PBS buffer vehicle, (BP26-WT+M2e)/Alum (BP26-WT, 20 μg; M2e, 7.3 μg), BP26-M2e (×4) (25 μg), BP26-M2e (×8) (18 μg), and BP26-M2e (×8)/Alum (BP26-M2e: 18 μg). Mice in each group were immunized thrice at intervals of three weeks by subcutaneous injection into both footpads.

Figure 5A:
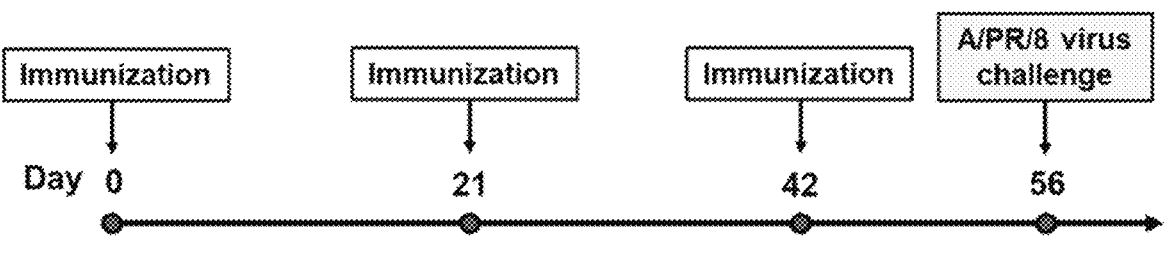
FIG. 5A shows the immunization schedule of Balb/c mice to evaluate the protective effect of the BP26-M2e nano vaccine against influenza virus.
Figure 5B:
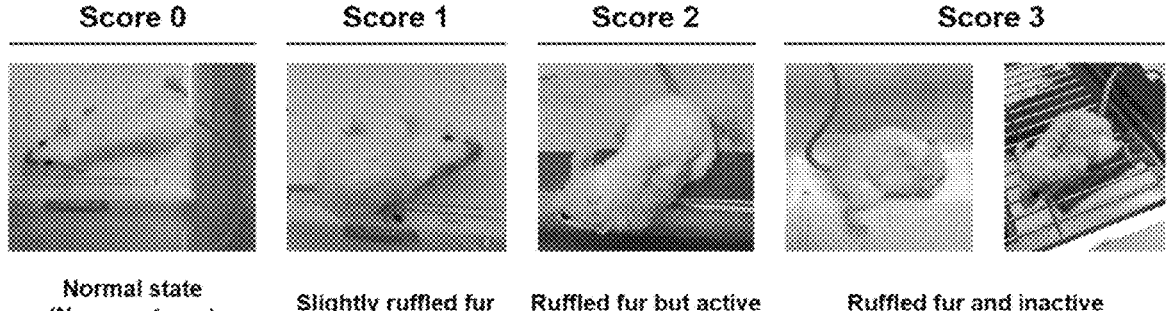
FIG. 5B shows clinical scores for influenza virus-infected mice.
Figure 5C:
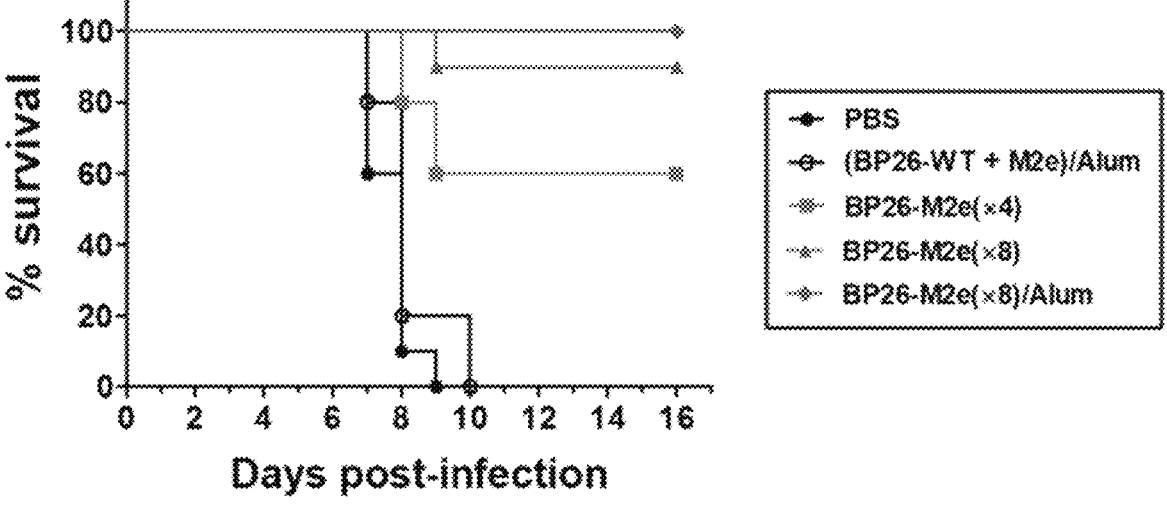
FIG. 5C shows measurements of survival rate to evaluate the protective effect of BP26-M2e nano vaccine against influenza virus.
Figure 5D:
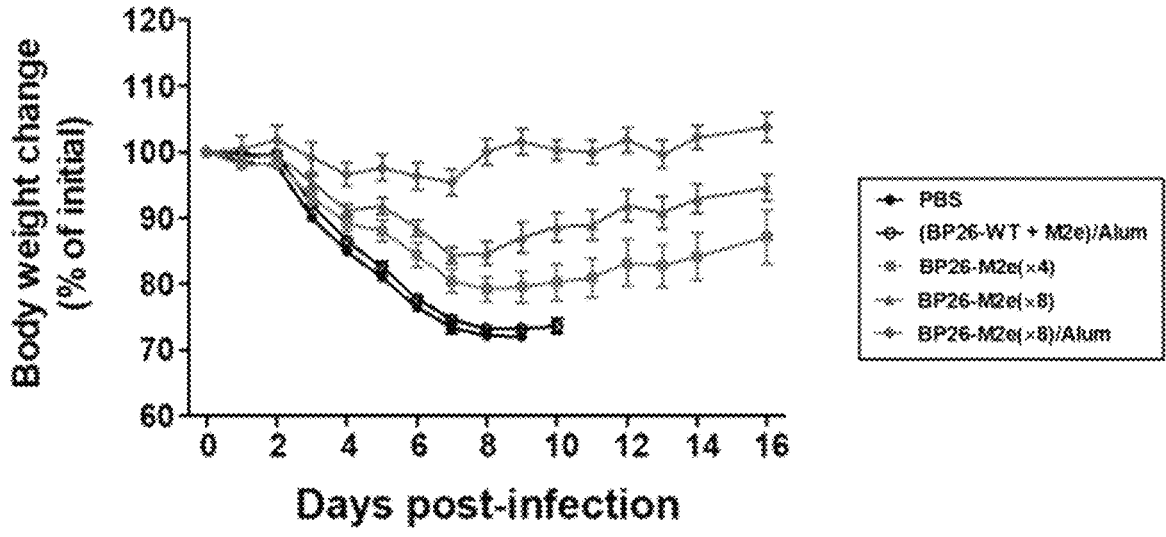
FIG. 5D shows body weight changes to evaluate the protective effect of the BP26-M2e nano vaccine against influenza virus.
Figure 5E:
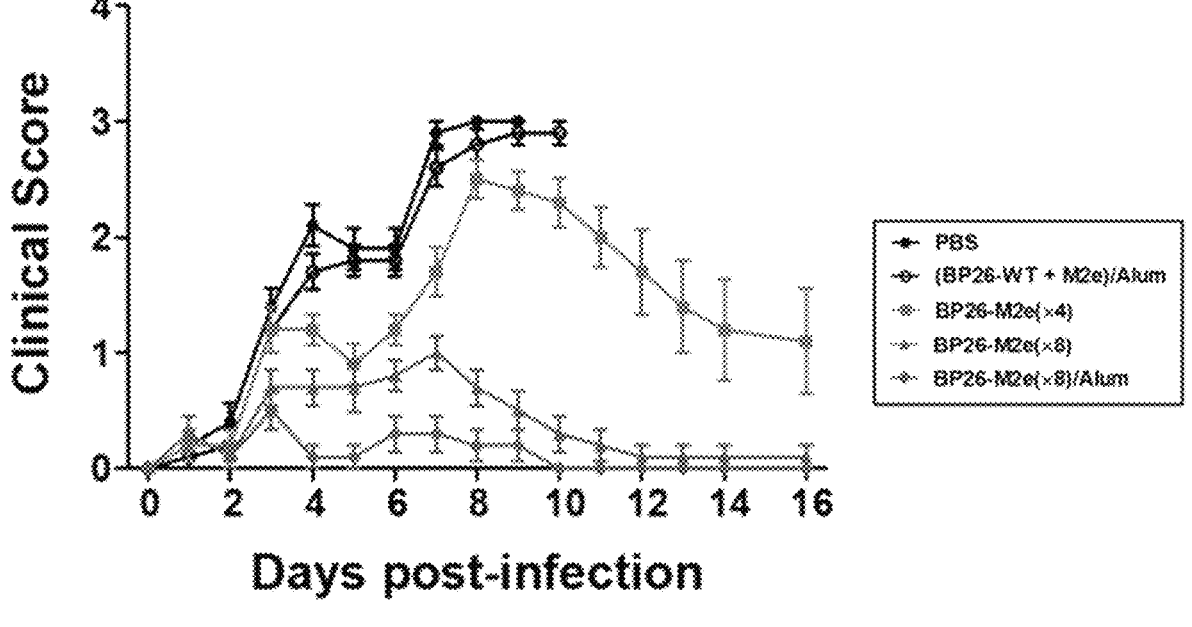
FIG. 5E shows clinical scores to evaluate the protective effect of BP26-M2e nano vaccine against influenza virus.
Figure 5F:
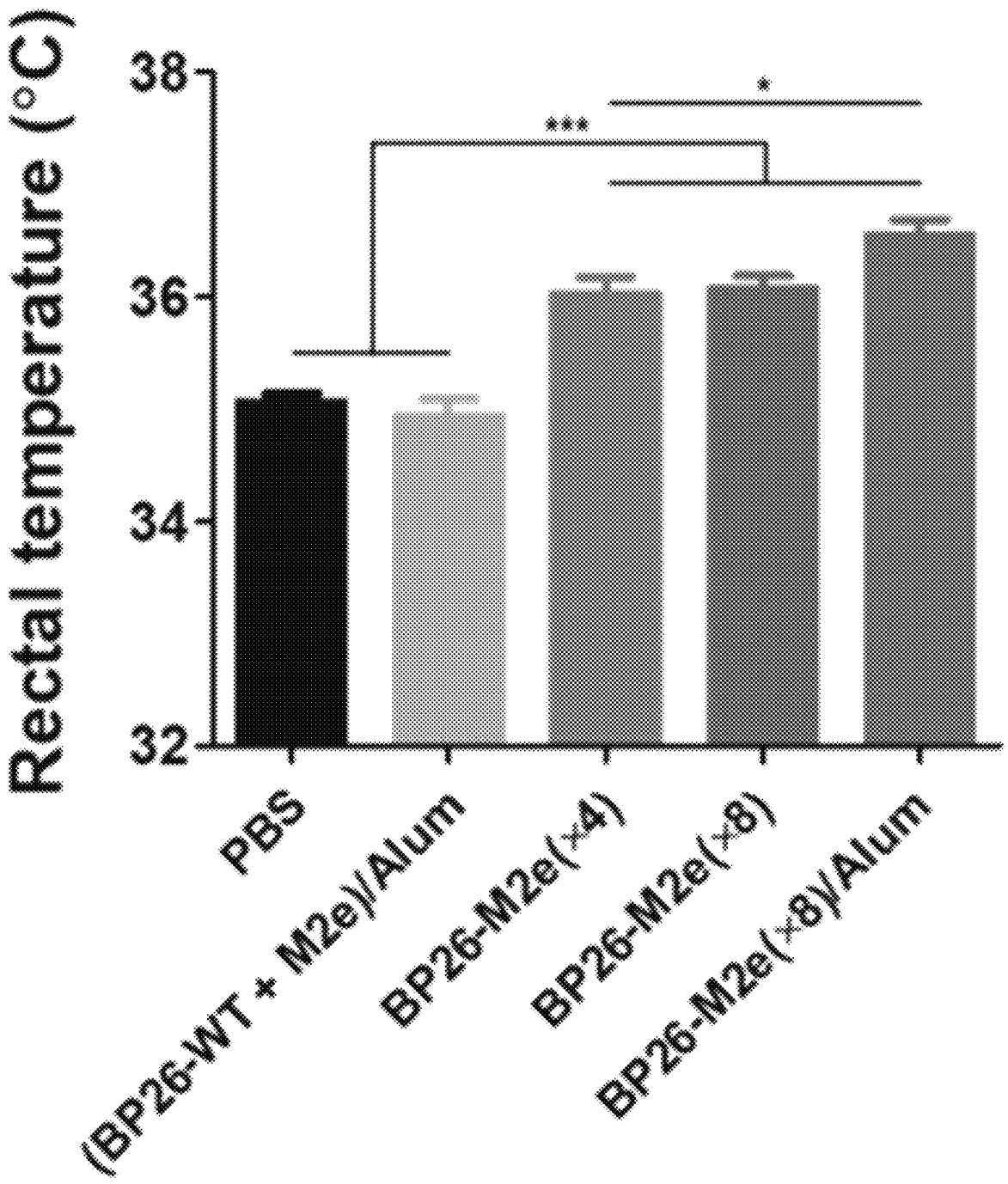
FIG. 5F shows rectal temperature measurements to evaluate the protective effect of BP26-M2e nano vaccine against influenza virus.

Mice were immunized thrice at 3-week intervals by intranasal administration of 30 μL of PBS containing a lethal dose (4×LD50) of A/PR/8 influenza virus two weeks after the last immunization (FIG. 5A). Mice were monitored every day for survival rates, body weight changes, clinical scores, and rectal temperatures for 16 days following the challenge infection. Mice that lost 25% or more of their initial body weight were euthanized humanely and included as experimental endpoints. Clinical scores were determined using the criteria described in FIG. 5B. Because influenza virus-infected mice unlike humans are reported to become hypothermic, rectal temperature was also measured.

Control influenza virus-infected mice treated with phosphate buffered saline (PBS) showed a loss in body weight by 30% or more, a sharp increase in clinical score, and drop in rectal temperature within 10 days after virus challenge.

Immunization with a physical mixture of BP26-WT and M2e together with alum adjuvant produced a trend similar to that observed in the PBS-treated group.

However, immunization with BP26-M2e (×4) increased survival rate to 60%, despite a significant loss in body weight; other symptoms gradually subsided and had abated by 8 days after the challenge infection.

Immunization with BP26-M2e (×8) further significantly increased the survival of mice to 80% while causing only mild symptoms (slightly ruffled fur) and a much lower clinical score compared with immunization with BP26-M2e (×4) which contained shorter antigen repeats.

Addition of alum adjuvant to BP26-M2e (×8) nanoarchitectures protected all mice from lethal influenza virus challenge (100% survival), together with slight body weight loss and faster recovery (FIGS. 5C to 5F).

Example 6: Measurement of Lung Viral Titer

To further confirm the protective immunity conferred by the BP26-M2e nanovaccine, lung viral titers were measured.

Mice were immunized in the same manner as in Example 3-1 as follows:

Mice were divided into five groups: PBS buffer vehicle, (BP26-WT+M2e)/Alum (BP26-WT, 20 μg; M2e, 7.3 μg), BP26-M2e (×4) (25 μg), BP26-M2e (×8) (18 μg), and BP26-M2e (×8)/Alum (BP26-M2e: 18 μg). Mice in each group were immunized thrice at intervals of three weeks by subcutaneous injection into both footpads.

Mice were immunized thrice at 3-week intervals by intranasal administration of 30 μL of PBS containing a lethal dose (4×LD50) of A/PR/8 influenza virus two weeks after the last immunization. Mice were euthanized three days after virus challenge and lung homogenate suspensions were obtained. Lung viral titers were determined in MDCK cells using a 50% tissue culture infectious dose (TCID50) assay.

Figure 5G:
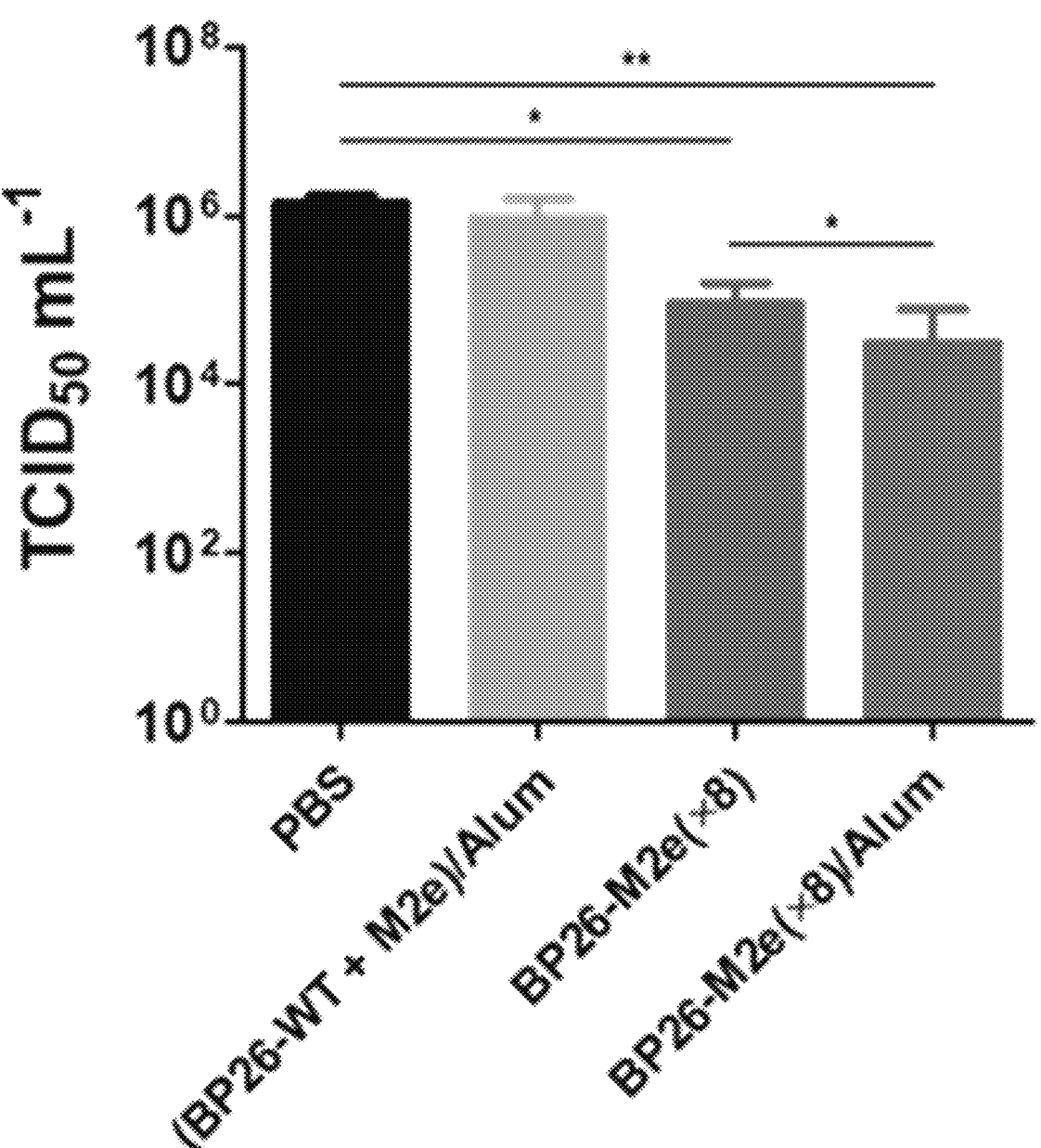
FIG. 5G shows residual lung viral titers in immunized mice measured 3 days after virus challenge.

Immunization with a physical mixture of BP26-WT+M2e and alum adjuvant failed to reduce lung viral titers, whereas immunization with either BP26-M2e (×8) alone or together with alum led to a significant reduction in lung viral titers (FIG. 5G).

Taken together, these results indicate that the BP26-M2e nanovaccine can generate strong cross-protective immunity against influenza virus infection, even without the use of a conventional adjuvant. Moreover, the protective efficacy can be tuned by controlling the length of the displayed antigen.

Figure 5H:
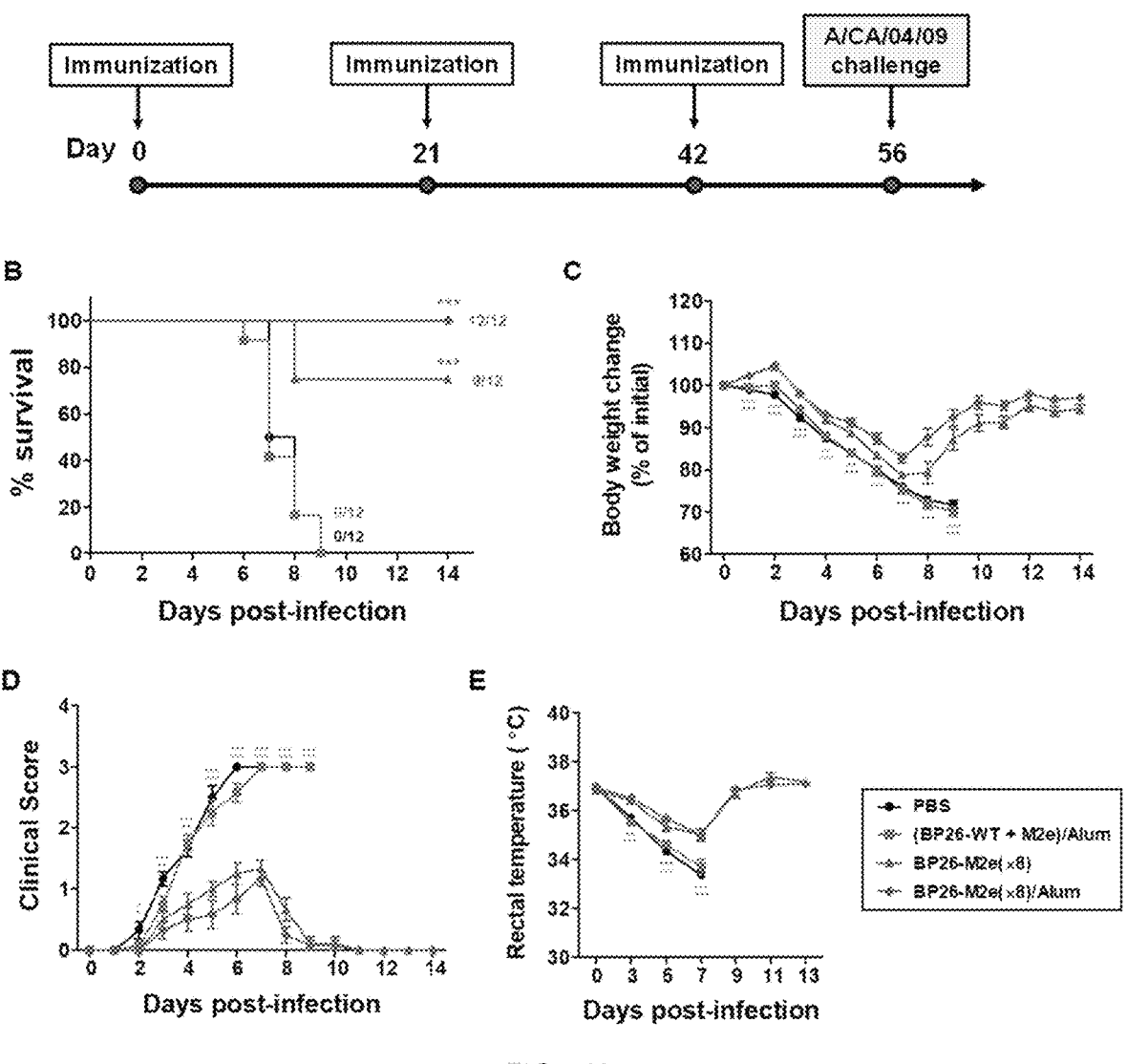
FIG. 5H shows Protective immunity of BP26-M2e nanovaccine after A/California/04/2009 (H1N1pdm09) challenge. (A) An immunization schedule for determining protective effects against influenza virus (n=12 mice per group). (B) Survival curves of A/CA/04/09-infected mice. (C) Body weight changes of influenza A virus-infected mice. (D) Clinical score of influenza A virus-infected mice. (E) Rectal temperature changes of influenza A virus-infected mice.

To examine the possibility of BP26-M2e nanobarrel as a universal vaccine against influenza virus infection, we evaluated cross-protection efficacy of the nanovaccine against another influenza A virus strain. Mice were immunized three times at 3-week intervals with PBS vehicle, (BP26-WT+M2e)/Alum, BP26-M2e (×8), or BP26-M2e (×8)/Alum. Two weeks after the final immunization, mice were challenged with a lethal dose (4×LD$_{50}$) of the 2009 pandemic strain, A/California/04/2009 (H1N1pdm09) (FIGS. 5H, A).

Protective efficacy was evaluated by measuring survival rates, body weight, clinical score and rectal temperature for 14 days post viral infection. PBS- and (BP26-WT+M2e)/Alum-immunized mice showed drastic body weight loss, a sharp increase in clinical score, and decrease of rectal temperature, thus all mice died or were euthanized within 9 days after viral infection (FIGS. 5H, B-E).

Figure 5I:
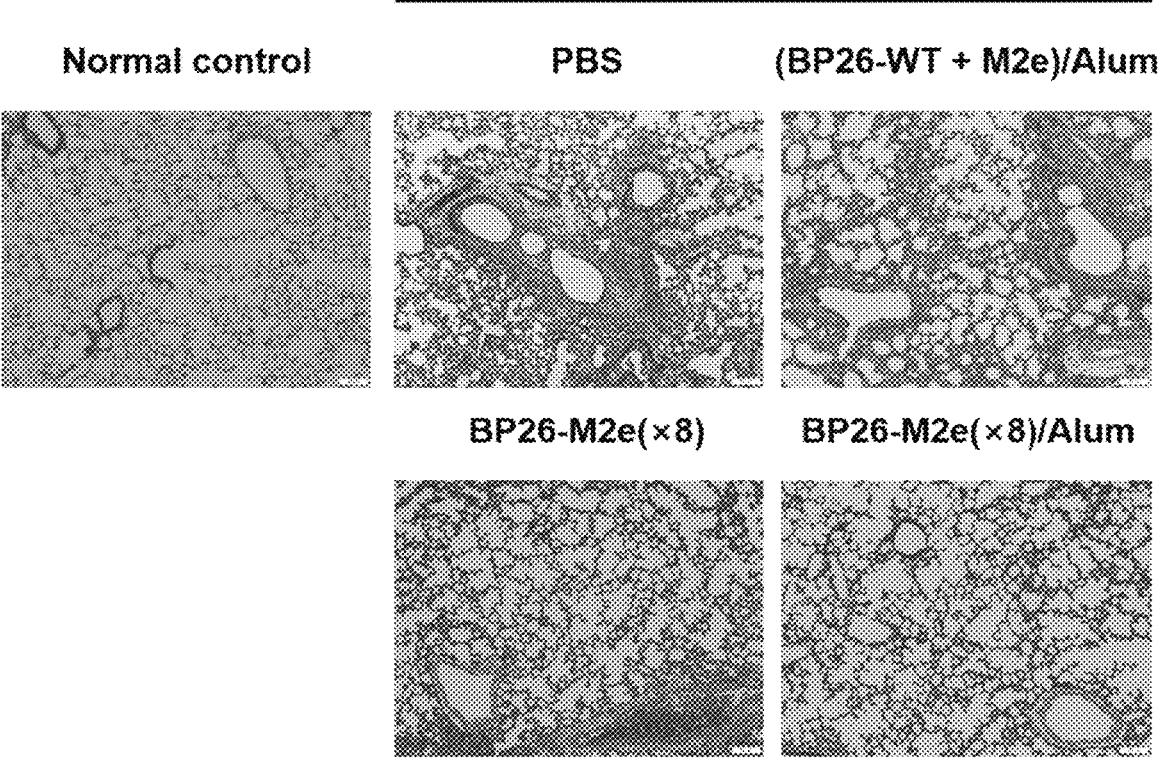
FIG. 5I shows Histology of lung tissues isolated from influenza A virus-challenged mice. Lung tissues were isolated from immunized mice with each modality at day 5 post infection with A/CA/04/09 and assessed by H&E staining. Images are representatives of each immunization group (n=3 mice per group). Scale bar=50 μm.

In contrast, immunization with BP26-M2e (×8) and BP26-M2e (×8)/Alum showed significantly increased survival rate to ~75% and 100%, respectively, and led to restoration of body weight, clinical score and rectal temperature of mice to the normal state. Histological analysis on lung tissues of the virus challenged mice revealed that both PBS- and (BP26-WT+M2e)/Alum-immunized groups developed severe pulmonary edema and peribronchiolar and perivascular inflammation, whereas such signs of inflammation were considerably reduced in the lungs of both BP26-M2e (×8) and BP26-M2e (×8)/Alum immunized mice (FIG. 5I).

From the result, the present inventors have developed a cross-protective universal vaccine platform against influenza A virus infection based on a protein nanoarchitecture formed by self-assembly of the *Brucella* outer membrane protein BP26. Genetic engineering of BP26 enabled generation of a barrel-shaped nanovaccine displaying the viral antigen M2e (BP26-M2e). Immunization of mice with BP26-M2e nanobarrel vaccines induced high-level production of anti-M2e antibodies that could specifically bind to influenza virus-infected cells and effectively protect mice from influenza infection even without the use of a conventional adjuvant.

The immune response to BP26-M2e nanobarrel vaccines can be tuned by controlling the length of tandem repeats of the M2e epitope. The BP26-based nanobarrel vaccines can be designed to display relatively large antigens as well as multiple epitopes to optimize or maximize humoral and cellular responses against various viruses. Furthermore, BP26-based vaccines can be produced in high yield through simple expression in *E. coli*, and thus have high commercialization potential for human or animal use.

The strong immune response induced by the present disclosure is due to the nanoarchitecture formed by BP26. Since there is no limitation on the polypeptide fused to BP26 by the linker, the nanoarchitecture of the present disclosure can induce immunity to various pathogens.

Therefore, it is expected that the unique features of the BP26-based nanobarrel system as a versatile vaccine platform may enable rapid development of antiviral vaccines against various bacteria and viruses, including SARS-COV-2, influenza viruses, and the like.

Figure 6:
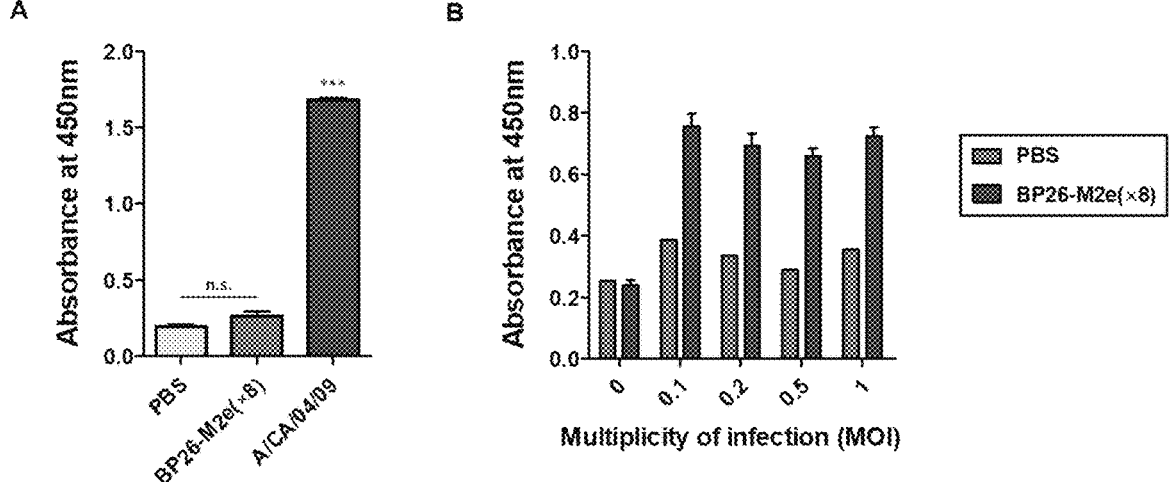
FIG. 6 shows analysis of binding modes of anti-M2e antibodies in the sera of BP26-M2e (×8) immunized mice. (A) Titer of anti-influenza A virus IgG in the sera of PBS-treated or BP26-M2e (×8) immunized mice was measured by ELISA. Sera from A/CA/04/09-infected mice were used as a positive control. Optical density of pre-immune sera on day-1 is ~0.13 (data not shown). (B) Whole-cell ELISA was conducted to examine binding of anti-M2e antibodies in the sera of PBS or BP26-M2e (×8) immunized mice to influenza A virus-infected MDCK cells.
Figure 7:
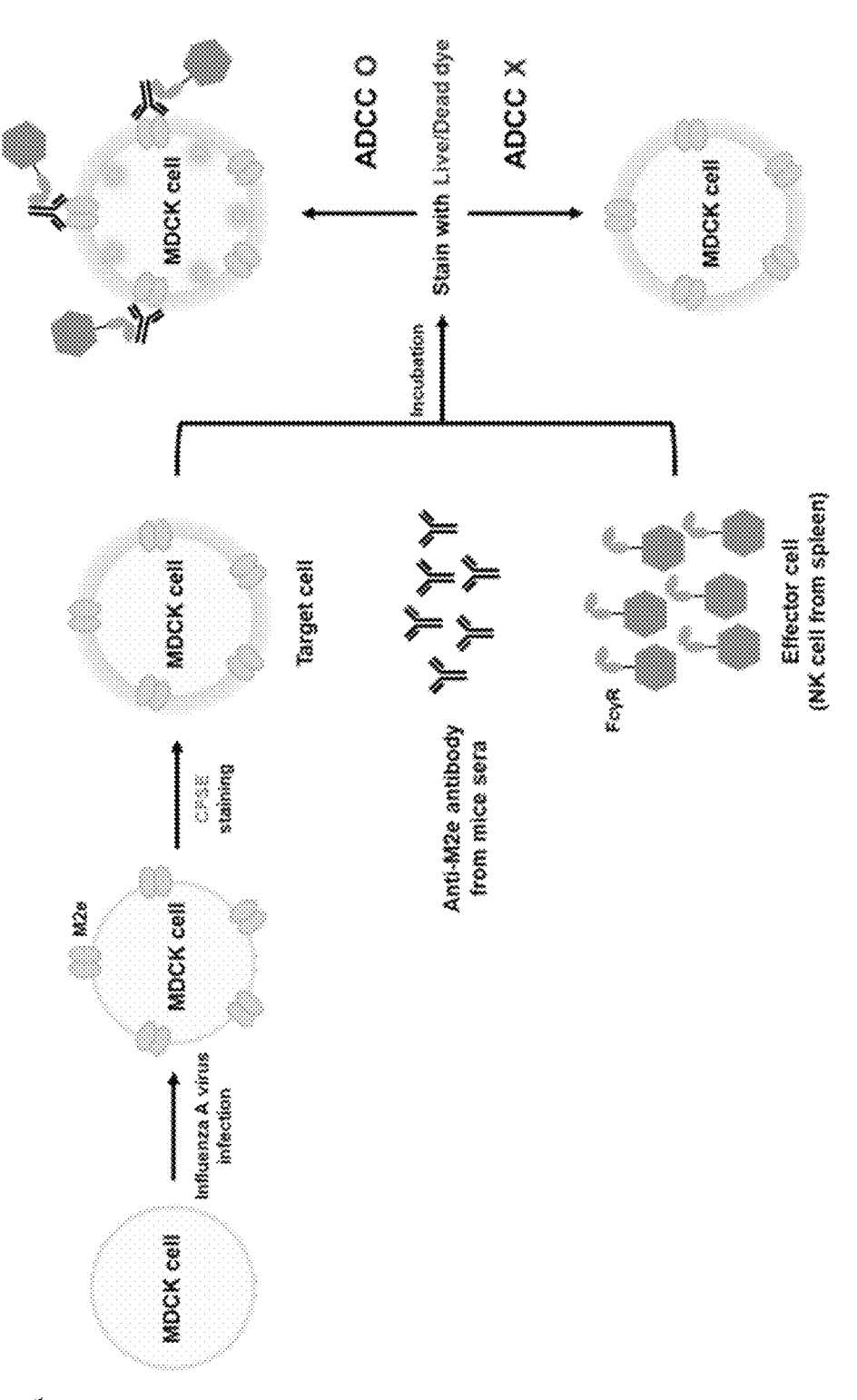
FIG. 7 shows that Anti-M2e antibodies in the sera of BP26-M2e nanovaccine-immunized mice can induce NK cell-mediated ADCC. (A) A schematic depiction of anti-M2e antibody-dependent NK cell-mediated cytotoxicity assay. Effector cells (NK cells) and target cells (influenza virus-infected MDCK cells) were co-incubated in the presence of sera from either PBS-treated mice or BP26-M2e (×8) immunized mice. (B) Representative flow cytometry results of ADCC assay. (C) Percentages of target cell-specific lysis at an E:T ratio of 2:1 or 1:2.
Figure 7:
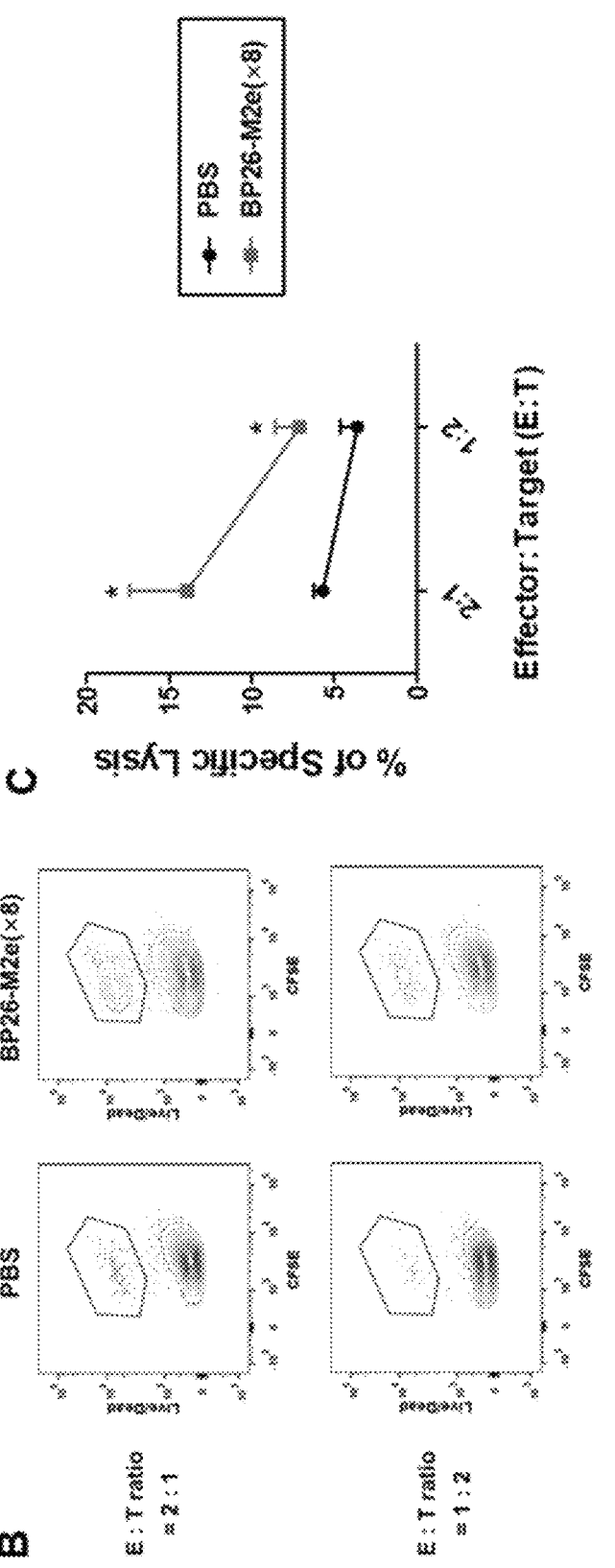

Example 7: BP26-M2e Nanovaccines Induce Both Antibody-Dependent Cellular Cytotoxicity and T Cell Responses Against Influenza Virus-Infected Cells The present inventors investigated mechanisms by which BP26-M2e nanovaccine exerts protection effects against influenza infection. We first examined whether anti-M2e antibodies in the sera of BP26-M2e (×8) immunized mice could be bound to influenza A virus directly and neutralize them. We found that the anti-M2e antibodies did not recognize the virus at all (FIGS. 6, A and B). This finding suggests that anti-M2e antibodies are not virus-neutralizing antibodies, which is in good agreement with findings reported previously. Because anti-M2e antibodies can be bound to influenza virus-infected cells as shown in FIG. 4 and FIG. 6 (B), it is expected that the antibody-dependent cellular cytotoxicity (ADCC) may be involved in immune protection of the nanobarrel vaccine. Natural killer (NK) cells are known to play a crucial role in ADCC for influenza virus-infected cells and thus, we evaluated NK cell-mediated ADCC by flow cytometry. A/PR/8 influenza virus-infected MDCK cells were stained with carboxyfluorescein succinimidyl ester (CFSE) and incubated with the sera of either PBS-treated or BP26-M2e (×8) immunized mice. NK cells (effector) isolated from mouse splenocytes were added to CFSE-labeled, virus-infected MDCK cells (target) at an effector to target (E:T) ratio of 2:1 or 1:2. Anti-M2e antibodies-dependent NK cells-mediated cytotoxicity was assessed using a live and dead assay (FIG. 7). Sera of BP26-M2e (×8) immunized mice resulted in much greater ADCC than that of PBS-treated control mice at the two-tested E:T ratios (viability of MDCK cells in the absence of NK cells was ~3.75%; data not shown) (FIG. 6B-C). These findings suggest that BP26-M2e nanovaccine induces generation of non-neutralizing M2e-specific antibodies that engage in NK cell-mediated ADCC capable of destroying M2e-exposed influenza virus-infected cells.

On the other hand, we further examined whether BP26-M2e nanovaccine can also induce T cell responses.[36-38] For evaluation of M2e antigen-specific T cell responses, mice were immunized three times at 3-week interval with PBS, a physical mixture of (BP26-WT+M2e)/Alum, BP26-M2e (×8), or BP26-M2e (×8)/Alum and sacrificed three weeks after the last immunization. Splenocytes were isolated from the immunized mice and restimulated with M2e antigen peptide. Intracellular cytokine staining (ICS) was performed to measure IFN-γ producing CD8+ and CD4+ T cells using flow cytometry. While both PBS control and the physical mixture of (BP26-WT+M2e)/Alum failed to induce M2e-specific T cell responses, BP26-M2e (×8) nanovaccine led to appreciable increase in the population of IFN-γ secreting CD8+ and CD4+ T cells; as expected, addition of alum adjuvant to BP26-M2e (×8) nanovaccine further enhanced the antigen-specific T cell responses. Taken together, these results of mechanism studies suggest that BP26-M2e nanovaccine may exert its immune protection efficacy against influenza virus by engaging in anti-M2e antibodies-mediated ADCC as well as by inducing M2e-specific T cell responses.

Example 8: Preparation of BP26-Containing Cancer Vaccine

The present inventors tried to prepare a cancer vaccine composition using a nanoarchitecture containing BP26. Specifically, the present inventors prepared a protein complex having a structure as shown in FIG. 6.

Figure 8:
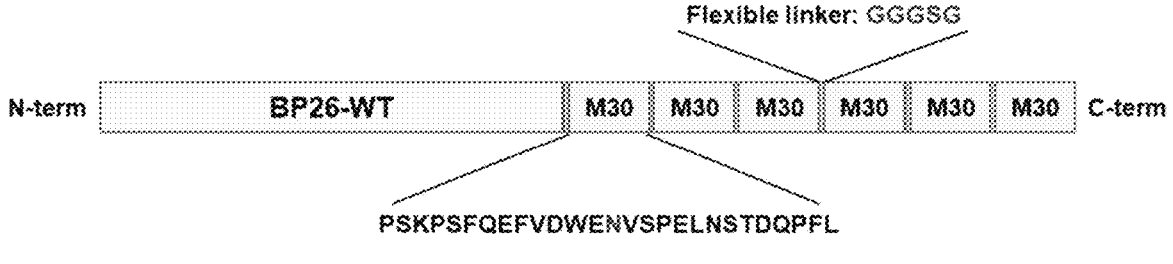
FIG. 8 is a schematic diagram of a protein complex constructed to confirm the use of BP26 of the present disclosure as a cancer vaccine.

As shown in FIG. 8, a fusion protein was designed that displays M30 (27 amino acids), an MHC class II neoantigen peptide of mouse melanoma cell line B16-F10, in 6 tandem repeats on the C-term side of the BP26 protein.

The amino acid sequence of M30 peptide and the nucleotide sequence encoding therefor are shown in Table 3.

TABLE 3

| Category | Sequence | SEQ ID NO: |
|---|---|---|
| Amino acid sequence of M30 | PSKPSFQEFVDWENVSPELNSTDQPFL | 8 |
| Nucleotide sequence of M30 (1) | CCGAGCAAACCGAGCTTCCAAGAGTTTGTGGACTGGG AAAACGTTAGCCCGGAGCTGAACAGCACCGATCAACC GTTCCTG | 9 |

TABLE 3-continued

| Category | Sequence | SEQ ID NO: |
|---|---|---|
| Nucleotide sequence of M30 (2) | CCGAGCAAGCCGAGCTTCCAAGAATTTGTGGACTGGG AGAACGTTAGCCCGGAACTGAACAGCACCGACCAACC GTTTCTG | 10 |
| Nucleotide sequence of M30 (3) | CCTTCTAAGCCGAGCTTCCAGGAGTTTGTGGACTGGG AGAATGTCTCTCCTGAGCTGAACAGCACTGACCAACC GTTCCTG | 11 |
| Nucleotide sequence of M30 (4) | CCTTCTAAACCGAGCTTCCAGGAATTTGTGGACTGGGA AAATGTGTCTCCTGAACTGAACAGCACTGATCAACCGT TTCTG | 12 |
| Nucleotide sequence of M30 (5) | CCTTCCAAACCGAGCTTCCAGGAGTTTGTGGACTGGG AAAACGTATCTCCCGAGCTGAACAGCACAGACCAACC GTTCCTG | 13 |
| Nucleotide sequence of M30 (6) | CCTTCAAAGCCGAGCTTCCAAGAGTTTGTGGACTGGG AGAATGTGAGCCCGGAGCTGAATAGCACCGACCAACC GTTCCTG | 14 |

There was a connection via the flexible linker between BP26 and M30 and between M30 and M30. In particular, since the M30 peptide can act as an MHC class II epitope to induce M30 antigen-specific CD4+ T cell response, development trend has been shifted from conventional anticancer vaccines focusing on the induction of CD8+ T cell-based antitumor immune responses toward anticancer vaccines capable of inducing CD4+ T cell responses.

Example 9: Efficacy Evaluation of BP26-Bearing Cancer Vaccine 9-1. Inoculation of Cancer Vaccine Inoculation and Efficacy on Tumor Growth Inhibition FIG. 9 is a diagram showing an immunization schedule for evaluating the efficacy of the BP26-bearing cancer vaccine of the present disclosure.

Figure 9:
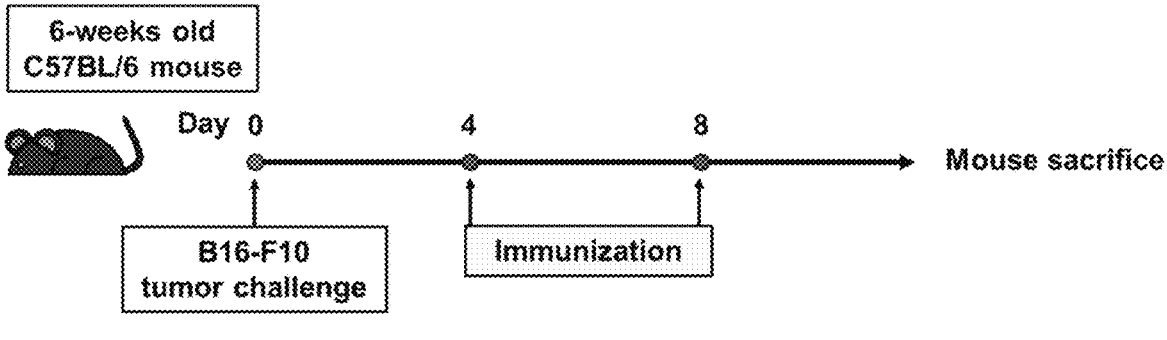
FIG. 9 a diagram of an immunization schedule for evaluating the efficacy of the BP26-containing cancer vaccine of the present disclosure.

As shown in FIG. 9, the present inventors inoculated the cells through subcutaneous injection of B16-F10 cancer cells (day 0). Then, immunization was conducted by administering the cancer vaccine composition (BP26 and M30 tandem repeat fusion protein, BP26-M30) prepared in Example 8 of the present disclosure at a dose of 46.8 μg/head a total of 2 times (day 4 and day 8) at intervals of four days from day 4 after inoculation of tumor cells. Five days after the last immunization, the mice were sacrificed, the spleen was excised, and splenocytes were isolated. For other experimental groups, an aqueous mixture (BP26-WT+M30) of BP26-WT (25.3 μg/head) and M30 peptide (20 μg/head) and a mixture of the cancer vaccine of the present disclosure and a vaccine adjuvant, CpG ODN (BP26-M30, 46.8 μg/head+CpG, 10 μg/head) were administered, respectively. The CpG ODN is an oligonucleotide composed of the nucleotide sequence of SEQ ID NO: 15 (5'-TCC ATG ACG TTC CTG ACG TT-3') and having a phosphorothioate backbone and was purchased from Genotech (Daejeon, Korea). As a control, PBS was administered (Control). In addition, the tumor volume was measured every 2 days after tumor cell inoculation until sacrifice.

Figure 10:
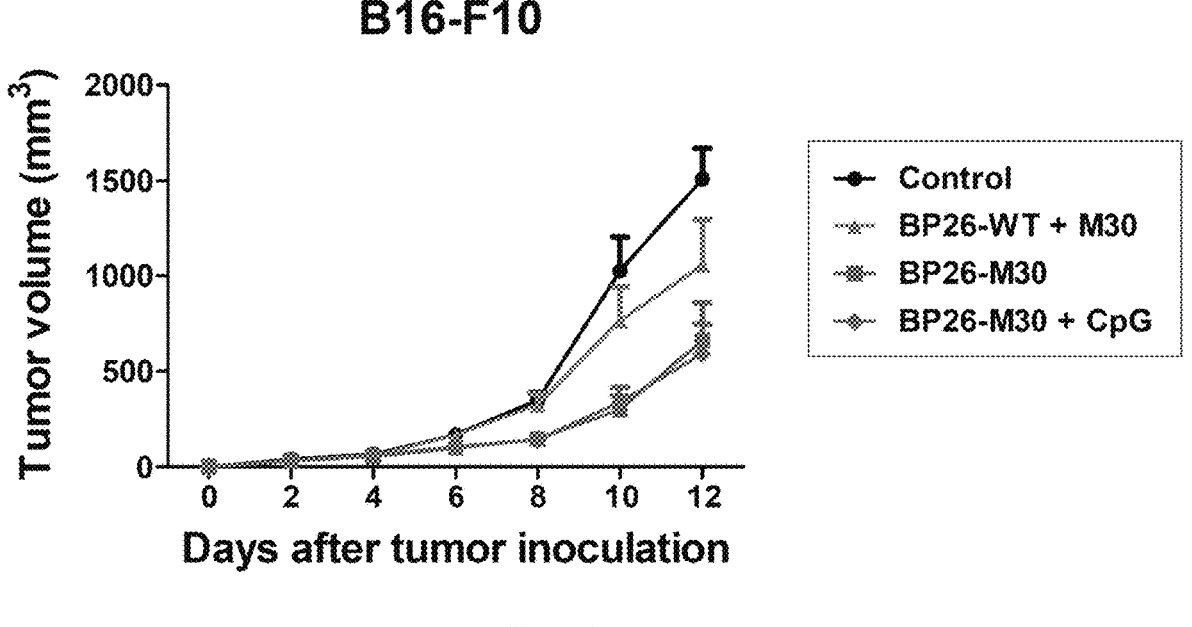
FIG. 10 is a plot of volumes of B16F10 tumor cells and shows degrees of growth of tumor cells.

The results are shown in FIG. 10.

FIG. 10 shows volumes of B16F10 tumor cells, accounting for degrees of growth of the tumor cells. As shown in FIG. 10, immunization of mice with the cancer vaccine composition (BP26-M30) of the present disclosure was observed to suppress tumor growth, compared to the other experimental group, i.e., the aqueous mixture of BP26-WT and M30 peptide (BP26-WT+M30). In addition, it was found that the cancer vaccine composition of the present disclosure suppressed tumor growth similarly to the mouse group (BP26-M30+CpG) to which the vaccine adjuvant CpG ODN was additionally administered.

9-2. Inoculation of Cancer Vaccine and Activation of Cellular Immune Response

The present inventors checked the percent of CD4+ T cells secreting IFN-γ to examine whether the M30 antigen-specific T cell immune response was induced, that is, to confirm the immunogenicity of the cancer vaccine.

Antigen-specific T cell responses were determined by ex vivo restimulation of splenocytes with M30 peptide (10 μg/ml), and INF-γ produced by CD4+ T cells was quantified as determined by intracellular cytokine staining (ICS).

In brief, GolgiStop™ or GolgiPlug™ (BD Biosciences) was added to each tube to inhibit intracellular transport of cytokines. The cells were then incubated for 5 hours. The cells were immunostained with Fixable Viability Dye eFluor450™ (eBioscience, San Diego, CA, USA) for 20 min at 4° C. to distinguish dead cells and then with anti-CD3 PE/Cy7 and anti-CD4 FITC antibodies for 20 min at 4° C. For intracellular cytokine staining, cells were permeabilized using a Cytofix/Cytoperm™ solution (BD Biosciences) and incubated with PE-conjugated anti-IFN-γ antibody. The samples were then washed and analyzed using flow cytometry.

Figure 11:
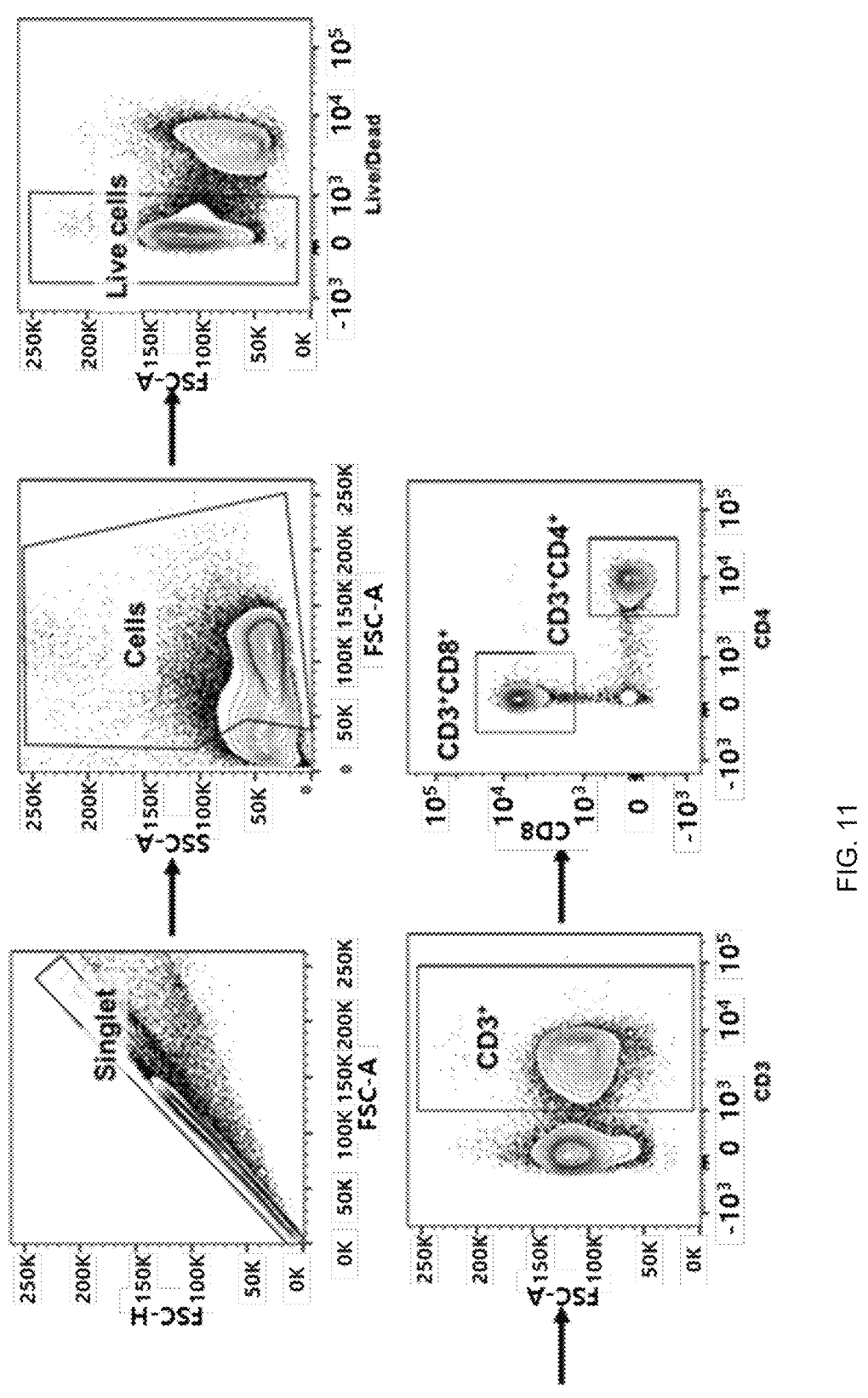
FIG. 11 shows a flow cytometry gating strategy of the present disclosure.

FIG. 11 shows a flow cytometry gating strategy for confirming proportions of IFN-γ-producing CD4+ T cells through flow cytometry for splenocytes. FSC×SSC gating was used to obtain single cells based on size and granularity, and dead cells were excluded to analyze only live cells. CD3, CD4 and CD8 were used as T cell markers. Finally, INF-γ secretion from CD3+CD4+ T cells was confirmed.

Figure 12:
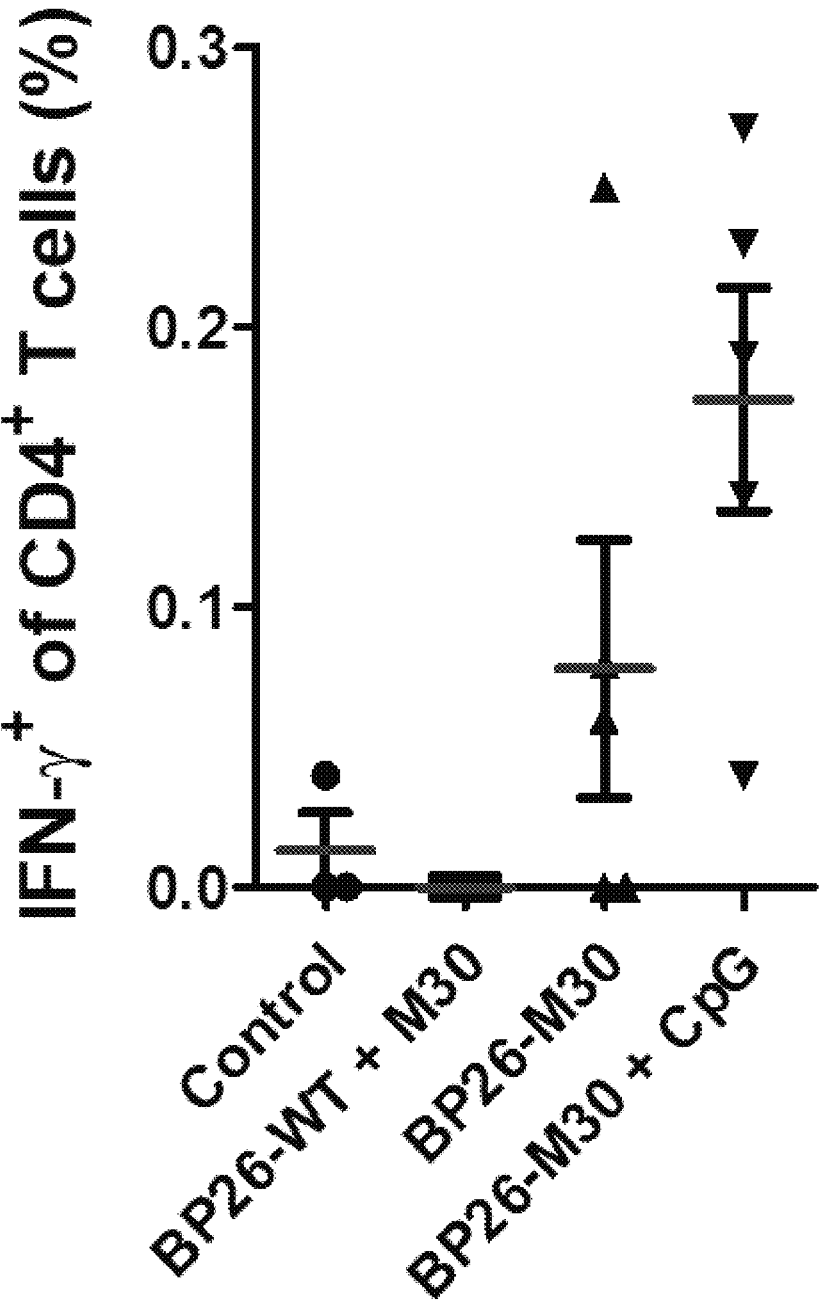
FIG. 12 is a plot of the % of CD4+ T cells secreting IFN-γ after immunization with the cancer vaccine containing BP26 of the present disclosure.

FIG. 12 is a plot of the % of CD4+ T cells secreting IFN-γ after immunization with the cancer vaccine containing BP26 of the present disclosure.

As shown in FIG. 12, the BP26-M30 cancer vaccine of the present disclosure was found to induce M30 antigen-specific CD4+ T cell response, compared to the control group and the BP26-WT+M30 aqueous mixture-administered group. In addition, when BP26-M30 and CpG ODN adjuvant were co-administered, the % of CD4+ T cells secreting IFN-γ was further improved, indicating that antigen-specific cellular immune response could be more effectively induced.

Taken together, the data obtained above exhibited that the BP26 platform of the present disclosure can effectively induce antigen-specific cellular immune responses when displaying cancer neoantigen peptide as well as M2e peptide of influenza virus, implying the possibility that the BP26 platform can be used not only as an influenza vaccine but also as a cancer vaccine.

Example 10. Optimization of Cancer Vaccine

The present inventors tried to optimize the design of the cancer vaccine prepared in Example 8.

Figure 13:
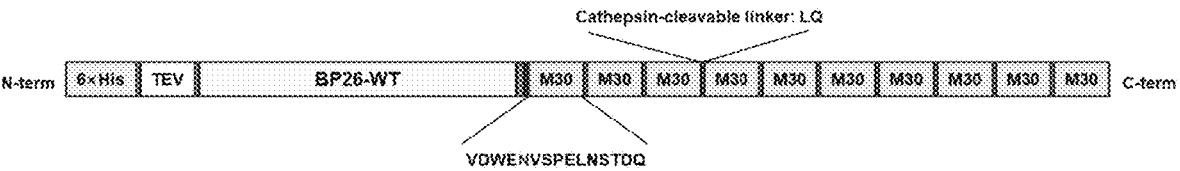
FIG. 13 shows a fusion protein displaying 10 tandem repeats of MHC class II neoantigen peptide M30 (15 amino acids, VDWENVSPELNSTDQ, SEQ ID NO: 16) from mouse melanoma cell line B16-F10 at the C-term of BP26 protein.

The present inventors designed a fusion protein displaying 10 tandem repeats of MHC class II neoantigen peptide M30 (15 amino acids, VDWENVSPELNSTDQ) from mouse melanoma cell line B16-F10 at the C-term of BP26 protein (FIG. 13). Between BP26 and M30 and between M30 and M30 were linked through LQ, a cathepsin cleavage linker. M30 peptide can induce M30 antigen-specific CD4+ T cell response by acting as an MHC class II epitope. Conventional anticancer vaccines have focused on CD8+ T cell-based antitumor immune responses. Therefore, the present inventors tried to develop an anticancer vaccine capable of inducing CD4+ T cell response as well as CD8+ T cell-based antitumor immune response.

Figure 14:
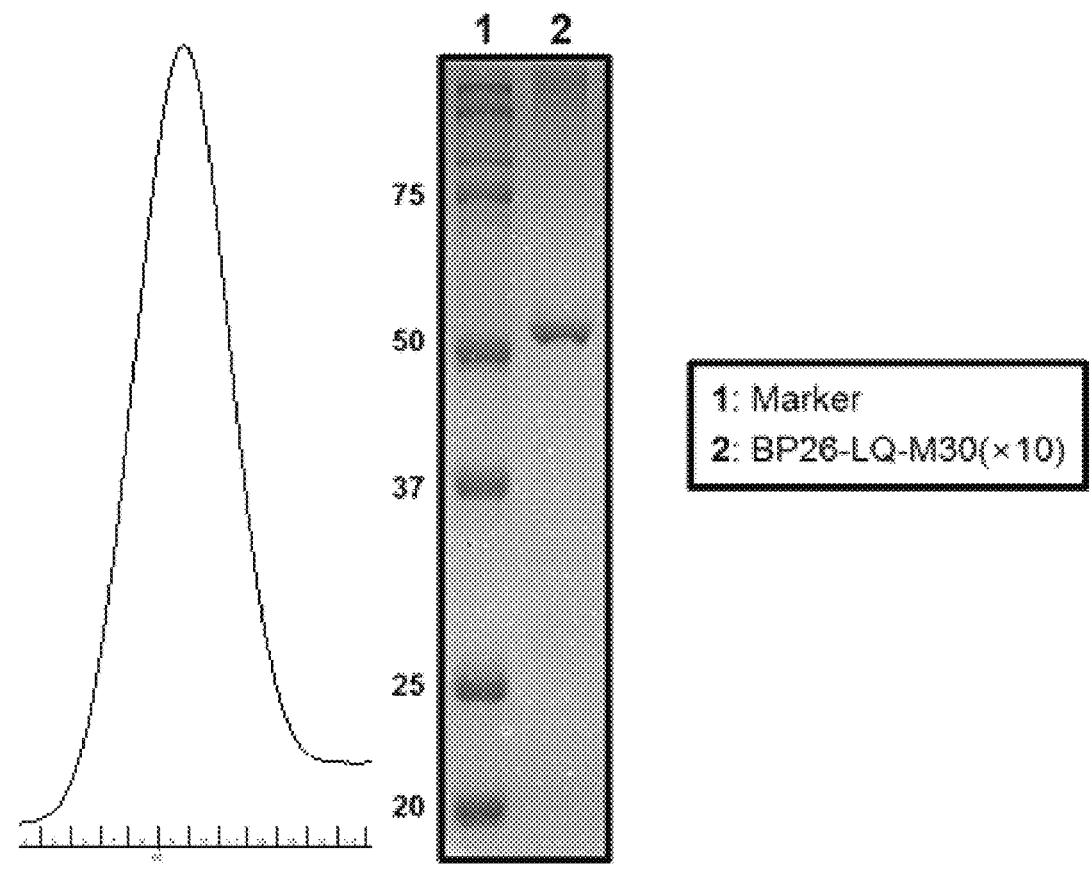
FIG. 14 is data on the purification and expression of the BP26-LQ-M30 (×10) fusion protein.

FIG. 14 is data on the purification and expression of the BP26-LQ-M30 (×10) fusion protein. As shown in FIG. 14, the BP26-LQ-M30 (×10) fusion protein was successfully expressed and purified. Purification was performed via FPLC, and SDS-PAGE showed that only the fusion protein was isolated.

Figure 15:
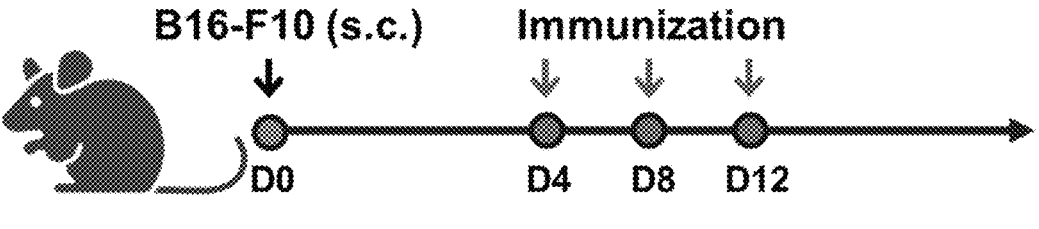
FIG. 15 shows the Vaccine immunization schedule.

FIG. 15 shows the Vaccine immunization schedule. As shown in FIG. 15, immunization was performed 3 times at intervals of 4 days from the 4th day after cell inoculation through subcutaneous injection of B16-F10 cancer cells.

Figure 16:
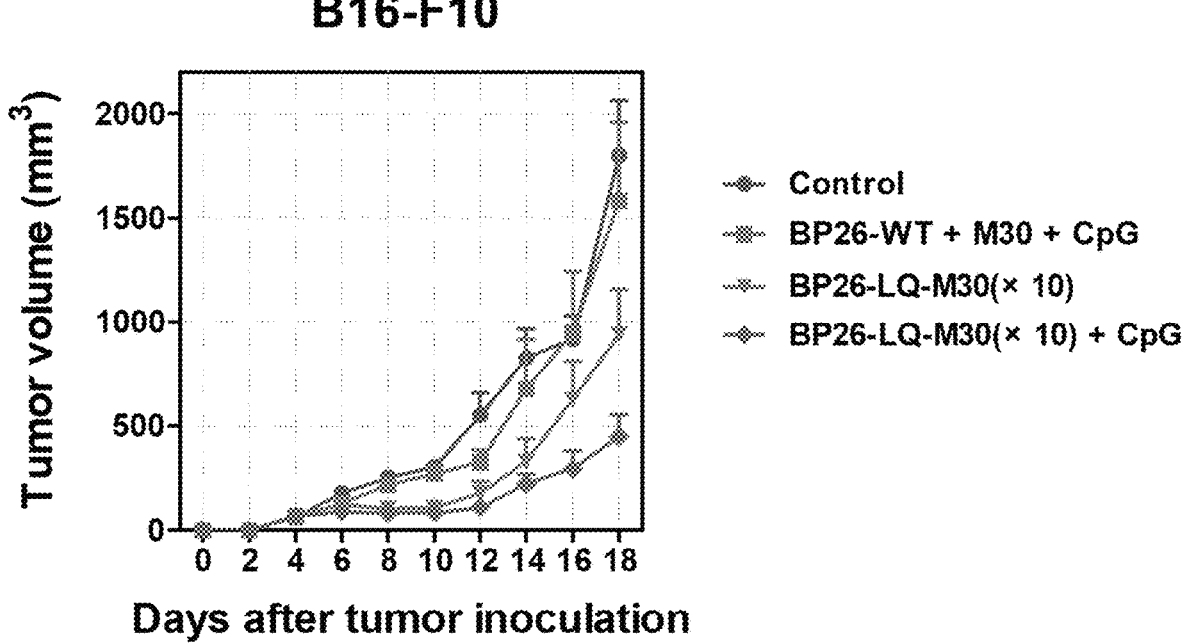
FIG. 16 shows the B16F10 tumor growth curve after inoculation with the BP26-LQ-M30 (×10) fusion protein.

FIG. 16 shows the B16F10 tumor growth curve after inoculation with the BP26-LQ-M30 (×10) fusion protein.

As shown in FIG. 16, when the fusion protein of BP26 and M30 tandem repeat (i.e., BP26-LQ-M30 (×10)) was immunized to mice, tumor growth was inhibited compared to a soluble mixture of BP26-WT and M30 peptides. In addition, tumor growth was further suppressed when the vaccine adjuvant CpG ODN group was added.

FIG. 17 shows the B16F10 tumor volume on the 18th day after tumor inoculation.

FIG. 18 shows the antigen-specific T cell immune response by inoculation with the BP26-LQ-M30 (×10) fusion protein.

Seven days after the final immunization on D12, the mice were sacrificed, and immune cells, splenocytes, were isolated from the spleen. After giving M30 peptide ex vivo restimulation to the isolated splenocytes, the CD4+ T cell population secreting interferon-gamma (IFN-γ) was analyzed by intracellular cytokine staining (ICS). As a positive control, PMA/Ionomycin ex vivo stimulation was additionally performed.

When M30 stimulation was performed, it was confirmed that the M30-antigen-specific CD4 T cell immune response was induced only in the BP26-LQ-M30 (×10)+CpG group (data on the left). When PMA/Ionomycin stimulation was given, no difference could be confirmed in all groups. from the above result From the results, it was confirmed that an antigen-specific T cell immune response was induced by inoculation with the BP26-LQ-M30 (×10) fusion protein.

Example 11. Optimization of Cancer Vaccine Immunization

In Example 10, the antitumor efficacy of the BP26-LQ-M30 (×10) fusion protein was verified. In this example, tests for optimizing vaccine administration were performed. Specifically, an experiment was conducted to find an optimal adjuvant capable of maximizing the antitumor efficacy of the BP26-LQ-M30 (×10) fusion protein.

The antitumor efficacy was confirmed when CpG ODN, a conventional adjuvant, and poly(I:C), an adjuvant mainly used in neoantigen vaccines, were used together. Results are shown in FIG. 19.

As shown in FIG. 19, when the adjuvant was administered together with the BP26-LQ-M30 (×10) fusion protein, the antitumor efficacy was improved, and the efficacy was particularly excellent when used together with CpG ODN.

FIG. 20 shows the efficacy of administration of the BP26-LQ-M30 (×10) fusion protein compared to the positive control group.

As a positive control group, the tumor volumes of the groups (M30pep+CpG and M30pep+poly(I:C)) administered with 5 times the dose of antigen and immunostimulant were compared. In the case of the positive control group, the administered dose was 5 times, but it showed antitumor efficacy similar to that of the BP26-LQ-M30 (×10) fusion protein+immune enhancer administration group.

FIG. 21 shows the B16F10 individual tumor growth curve of each group shown in FIG. 20.

INDUSTRIAL APPLICABILITY

The present disclosure relates to a fusion protein comprising BP26 and an antigenic polypeptide.

---

SEQUENCE LISTING

```
Sequence total quantity: 19
SEQ ID NO: 1              moltype = AA  length = 222
FEATURE                   Location/Qualifiers
REGION                    1..222
                          note = BP26
source                    1..222
                          mol_type = protein
                          organism = synthetic construct
SEQUENCE: 1
QENQMTTQPA RIAVTGEGMM TASPDMAILN LSVLRQAKTA REAMTANNEA MTKVLDAMKK  60
AGIEDRDLQT GGIDIQPIYV YPDDKNNLKE PTITGYSVST SLTVRVRELA NVGKILDESV  120
TLGVNQGGDL NLVNDNPSAV INEARKRAVA NAIAKAKTLA DAAGVGLGRV VEISELSRPP  180
MPMPIARGQF RTMLAAAPDN SVPIAAGENS YNVSVNVVFE IK                     222
```

-continued

```
SEQ ID NO: 2              moltype = AA  length = 264
FEATURE                   Location/Qualifiers
REGION                    1..264
                          note = BP26 comprising His tag and TEV cleavage site
source                    1..264
                          mol_type = protein
                          organism = synthetic construct
SEQUENCE: 2
MGSSHHHHHH SSGLVPRGSH MASMTGGQQM GRGSENLYFQ GSQENQMTTQ PARIAVTGEG  60
MMTASPDMAI LNLSVLRQAK TAREAMTANN EAMTKVLDAM KKAGIEDRDL QTGGIDIQPI  120
YVYPDDKNNL KEPTITGYSV STSLTVRVRE LANVGKILDE SVTLGVNQGG DLNLVNDNPS  180
AVINEARKRA VANAIAKAKT LADAAGVGLG RVVEISELSR PPMPMPIARG QFRTMLAAAP  240
DNSVPIAAGE NSYNVSVNVV FEIK                                        264

SEQ ID NO: 3              moltype = AA  length = 23
FEATURE                   Location/Qualifiers
REGION                    1..23
                          note = M2e
source                    1..23
                          mol_type = protein
                          organism = synthetic construct
SEQUENCE: 3
SLLTEVETPI RNEWGSRSND SSD                                          23

SEQ ID NO: 4              moltype = AA  length = 23
FEATURE                   Location/Qualifiers
REGION                    1..23
                          note = M2e(A/PR/8)
source                    1..23
                          mol_type = protein
                          organism = synthetic construct
SEQUENCE: 4
SLLTEVETPI RNEWGCRCND GSD                                          23

SEQ ID NO: 5              moltype = AA  length = 23
FEATURE                   Location/Qualifiers
REGION                    1..23
                          note = M2e(A/CA/04/09)
source                    1..23
                          mol_type = protein
                          organism = synthetic construct
SEQUENCE: 5
SLLTEVETPT RNGWECKCSD SSD                                          23

SEQ ID NO: 6              moltype = AA  length = 23
FEATURE                   Location/Qualifiers
REGION                    1..23
                          note = M2e(A/Aquatic bird/Korea)
source                    1..23
                          mol_type = protein
                          organism = synthetic construct
SEQUENCE: 6
SLLTEVETPT RSEWECRCSD SSD                                          23

SEQ ID NO: 7              moltype = DNA  length = 69
FEATURE                   Location/Qualifiers
misc_feature              1..69
                          note = M2e
source                    1..69
                          mol_type = other DNA
                          organism = synthetic construct
SEQUENCE: 7
agcctgctga ccgaagtcga gactccgatc cgtaatgaat ggggctctcg ttctaacgac  60
tcgtcggat                                                         69

SEQ ID NO: 8              moltype = AA  length = 27
FEATURE                   Location/Qualifiers
REGION                    1..27
                          note = Amino acid sequence of M30
source                    1..27
                          mol_type = protein
                          organism = synthetic construct
SEQUENCE: 8
PSKPSFQEFV DWENVSPELN STDQPFL                                      27

SEQ ID NO: 9              moltype = DNA  length = 81
FEATURE                   Location/Qualifiers
misc_feature              1..81
```

```
                          note = Nucleotide sequence of M30 (1)
source                    1..81
                          mol_type = other DNA
                          organism = synthetic construct
SEQUENCE: 9
ccgagcaaac cgagcttcca agagtttgtg gactgggaaa acgttagccc ggagctgaac    60
agcaccgatc aaccgttcct g                                              81

SEQ ID NO: 10             moltype = DNA   length = 81
FEATURE                   Location/Qualifiers
misc_feature              1..81
                          note = Nucleotide sequence of M30 (2)
source                    1..81
                          mol_type = other DNA
                          organism = synthetic construct
SEQUENCE: 10
ccgagcaagc cgagcttcca agaatttgtg gactgggaga acgttagccc ggaactgaac    60
agcaccgacc aaccgtttct g                                              81

SEQ ID NO: 11             moltype = DNA   length = 81
FEATURE                   Location/Qualifiers
misc_feature              1..81
                          note = Nucleotide sequence of M30 (3)
source                    1..81
                          mol_type = other DNA
                          organism = synthetic construct
SEQUENCE: 11
ccttctaagc cgagcttcca ggagtttgtg gactgggaga atgtctctcc tgagctgaac    60
agcactgacc aaccgttcct g                                              81

SEQ ID NO: 12             moltype = DNA   length = 81
FEATURE                   Location/Qualifiers
misc_feature              1..81
                          note = Nucleotide sequence of M30 (4)
source                    1..81
                          mol_type = other DNA
                          organism = synthetic construct
SEQUENCE: 12
ccttctaaac cgagcttcca ggaatttgtg gactgggaaa atgtgtctcc tgaactgaac    60
agcactgatc aaccgtttct g                                              81

SEQ ID NO: 13             moltype = DNA   length = 81
FEATURE                   Location/Qualifiers
misc_feature              1..81
                          note = Nucleotide sequence of M30 (5)
source                    1..81
                          mol_type = other DNA
                          organism = synthetic construct
SEQUENCE: 13
ccttccaaac cgagcttcca ggagtttgtg gactgggaaa acgtatctcc cgagctgaac    60
agcacagacc aaccgttcct g                                              81

SEQ ID NO: 14             moltype = DNA   length = 81
FEATURE                   Location/Qualifiers
misc_feature              1..81
                          note = Nucleotide sequence of M30 (6)
source                    1..81
                          mol_type = other DNA
                          organism = synthetic construct
SEQUENCE: 14
ccttcaaagc cgagcttcca agagtttgtg gactgggaga atgtgagccc ggagctgaat    60
agcaccgacc aaccgttcct g                                              81

SEQ ID NO: 15             moltype = DNA   length = 20
FEATURE                   Location/Qualifiers
misc_feature              1..20
                          note = CpG oligodeoxynucleotide
source                    1..20
                          mol_type = other DNA
                          organism = synthetic construct
SEQUENCE: 15
tccatgacgt tcctgacgtt                                                20

SEQ ID NO: 16             moltype = AA   length = 15
FEATURE                   Location/Qualifiers
source                    1..15
                          mol_type = protein
                          organism = synthetic construct
SEQUENCE: 16
```

-continued

```
VDWENVSPEL NSTDQ                                                       15

SEQ ID NO: 17          moltype = AA   length = 5
FEATURE                Location/Qualifiers
source                 1..5
                       mol_type = protein
                       organism = synthetic construct
SEQUENCE: 17
GGGGS                                                                  5

SEQ ID NO: 18          moltype = AA   length = 4
FEATURE                Location/Qualifiers
source                 1..4
                       mol_type = protein
                       organism = synthetic construct
SEQUENCE: 18
GGGG                                                                   4

SEQ ID NO: 19          moltype = AA   length = 5
FEATURE                Location/Qualifiers
source                 1..5
                       mol_type = protein
                       organism = synthetic construct
SEQUENCE: 19
GGGSG                                                                  5
```

What is claimed is:

1. A nanoarchitecture comprising a fusion protein comprising BP26 and an antigenic polypeptide,
   wherein the antigenic polypeptide is linked to the C-terminus of the BP26, and no antigenic polypeptide is linked to the N-terminus of the BP26; and
   wherein the nanoarchitecture comprises 8 or 16 copies of the fusion protein.

2. A vaccine composition comprising the nanoarchitecture of claim 1.

3. The vaccine composition of claim 2, wherein the vaccine composition is for preventing infection from an infectious pathogen.

4. The vaccine composition of claim 2, wherein the vaccine composition is for a cancer vaccine.

5. The vaccine composition of claim 2, wherein the vaccine composition further comprises an adjuvant.

6. The nanoarchitecture of claim 1, wherein the BP26 comprises the amino acid sequence of SEQ ID NO: 1 or 2.

7. The nanoarchitecture of claim 1, wherein the antigen is a pathogen-derived antigen or a tumor-derived antigen.

8. The nanoarchitecture of claim 7, wherein the pathogen is selected from the group consisting of a virus, a bacterium, a *Rickettsia*, a fungus, and a protozoa.

9. The nanoarchitecture of claim 7, wherein the pathogen-derived antigenic polypeptide is M2e.

10. The nanoarchitecture of claim 9, wherein the M2e comprises the amino acid sequence of SEQ ID NO: 3, 4, 5, or 6.

11. The nanoarchitecture of claim 1, wherein the fusion protein comprises at least one copy of the antigenic polypeptide.

12. The nanoarchitecture of claim 1, wherein the antigenic polypeptides are continuously or discontinuously linked in the fusion protein.

* * * * *